(12) United States Patent
Kim et al.

(10) Patent No.: US 6,310,246 B1
(45) Date of Patent: Oct. 30, 2001

(54) FLUOROVINLOXYACETAMIDES, PROCESS FOR PREPARING SAME AND HERBICIDAL COMPOSITION COMPRISING SAME

(75) Inventors: Bum-Tae Kim; No-Kyun Park; Kyung-Sik Hong, all of Daejeon; Jae-Eup Park, Seoul; Yong-Woong Kwon, Kwacheon-shi, all of (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/638,852

(22) Filed: Aug. 14, 2000

Related U.S. Application Data

(63) Continuation of application No. PCT/KR99/00116, filed on Mar. 15, 1999.

(30) Foreign Application Priority Data

Mar. 16, 1998 (KR) .................................... 98-8750
Mar. 16, 1998 (KR) .................................... 98-8751
Feb. 24, 1999 (KR) .................................... 99-6035

(51) Int. Cl.[7] ...................... C07C 233/05; A01N 37/18
(52) U.S. Cl. ...................... 564/170; 504/220; 504/249; 504/289; 504/336; 540/607; 546/197; 546/226; 549/77; 564/182
(58) Field of Search .................. 504/336, 289, 504/249, 220; 540/607; 546/197, 226; 549/77; 564/170, 182

(56) References Cited

FOREIGN PATENT DOCUMENTS

56123956 * 9/1981 (JP) .
9708160 * 3/1997 (WO) .

* cited by examiner

Primary Examiner—Shailendra Kumar
(74) Attorney, Agent, or Firm—Roseman & Colin, LLP.

(57) ABSTRACT

Herbicidal fluorovinyloxyacetamide compounds of formula (I) are useful for protecting crops from weeds:

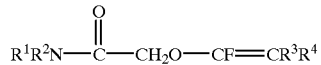

wherein:
- $R^1$ is a phenyl group optionally having one or more substituents selected from the group consisting of $C_{1-6}$ alkyl, halogen-substituted $C_{1-6}$ alkyl, $C_{1-6}$ alkoxy and halogen;
- $R^2$ is a $C_{1-6}$ alkyl; or
- $R^1$ and $R^2$ together with the nitrogen atom to which they are bound form a 5-, 6- or 7-membered nitrogen heterocycle optionally having one or more ring oxygen atoms, double bonds and $C_{1-6}$ alkyl substituents;
- $R^3$ is a phenyl or thiophen-2-yl group optionally having one or more substituents selected from the group consisting of $C_{1-6}$ alkyl, halogen-substituted $C_{1-6}$ alkyl, $C_{1-6}$ alkoxy, methylenedioxy and halogen; and
- $R^4$ is a perfluoro $C_{1-6}$ alkyl group.

7 Claims, No Drawings

FLUOROVINLOXYACETAMIDES, PROCESS FOR PREPARING SAME AND HERBICIDAL COMPOSITION COMPRISING SAME

CROSS REFERENCE TO RELATED APPLICATION

This application is a continuation of international application number PCT/KR99/00116, filed on Mar. 15, 1999, which is pending.

FIELD OF THE INVENTION

The present invention relates to novel fluorovinyloxyacetamides, a process for preparing same and a highly selective and effective herbicidal composition comprising same.

DESCRIPTION OF THE PRIOR ART

Due to the perpetual emergence of weeds resistant to the herbicide in use, there always exists a need to develop a new class of effective herbicides that can protect crops without harming the environment. For example, the sulfonylurea-based herbicides that have been widely used in controlling rice-field weeds for the last two decades have now become less effective, particularly in controlling annual weeds. Accordingly, many attempts have been made to develop new rice-field herbicides of different chemical classes, including those based on amides and carbamates.

There has recently been reported a new class of herbicides based on heteroaryloxyacetamide derivatives (DE Patent No. 2903966; DE Patent No. 3038636; DE Patent No. 3323334; DE Patent No. 3344236; DE Patent No. 3418167; DE Patent No. 3422861; DE Patent No. 440596; WO 95/34560; WO 96/08488; WO 96/11575; WO 96/28434; and WO 97/08160). However, these heteroaryloxyacetamides have limited herbicidal activity against a narrow spectrum of weeds.

SUMMARY OF THE INVENTION

Accordingly, it is a primary object of the present invention to provide a novel compound having superior herbicidal activity against a wide spectrum of weeds.

It is another object of the present invention to provide a process for the preparation of said compound.

It is a further object of the present invention-to provide a herbicidal composition comprising said compound.

In accordance with one aspect of the present invention, there is provided a novel fluorovinyloxyacetamide compound of formula (I):

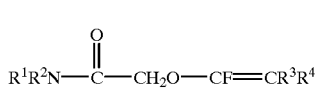

(I)

wherein:
- $R^1$ is a phenyl group optionally having one or more substituents selected from the group consisting of $C_{1-6}$ alkyl, halogen-substituted $C_{1-6}$ alkyl, $C_{1-6}$ alkoxy and halogen;
- $R^2$ is a $C_{1-6}$ alkyl group; or
- $R^1$ and $R^2$ together with the nitrogen atom to which they are bound form a 5-, 6- or 7-membered nitrogen heterocycle optionally having one or more ring oxygen atoms, double bonds and $C_{1-6}$ alkyl substituents;
- $R^3$ is a phenyl or thiophen-2-yl group optionally having one or more substituents selected from the group consisting of $C_{1-6}$ alkyl, halogen-substituted $C_{1-6}$ alkyl, $C_{1-6}$ alkoxy, methylenedioxy and halogen; and
- $R^4$ is a perfluoro $C_{1-6}$ alkyl group.

DETAILED DESCRIPTION OF THE INVENTION

The compound of formula (I) of the present invention may be in the form of the E isomer of formula (I-a), the Z isomer of formula (I-b), or a mixture thereof:

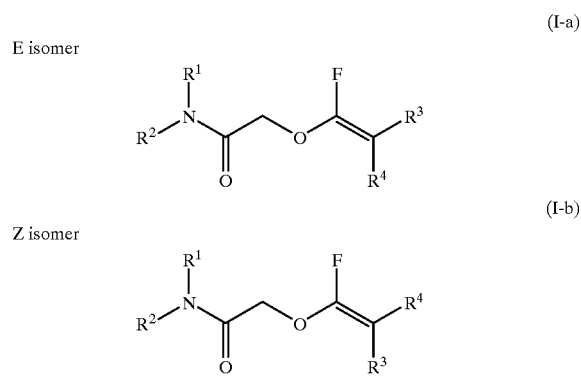

wherein $R^1$, $R^2$, $R^3$ and $R^4$ have the same meanings as defined in formula (I) above. The two stereoisomers, E and X isomers, are defined according to the terminology of the Cahn-Ingold-Prelog system(J. March, *Advanced organic Chemistry*, 3rd Ed., Wiley-Interscience) which is incorporated herein by way of reference.

Among the compounds of the present invention, preferred are: those wherein $R^1$ is a phenyl group optionally having a halogen, methyl or methoxy substituent, $R^2$ is a methyl or ipropyl group, $R^3$ is a phenyl group optionally substituted with a halogen or methoxy group and $R^4$ is $CF_3$ or $CF_2CF_3$; and those wherein $R^1$ and $R^2$ together with the nitrogen atom to which they are bound form a piperidino, hexamethyleneimino, morphorino or 1,2,3,6-tetrahydropyridino ring optionally having one or two $C_{1-2}$ alkyl substituents, $R^3$ is a phenyl group optionally substituted with a halogen or methoxy group and $R^4$ is $CF_3$.

The compound of the present invention may be prepared by reacting an alcoholic compound of formula (II) with a fluorovinyl compound of formula (III) in the presence of a base, as shown in Reaction Scheme A:

Reaction Scheme A

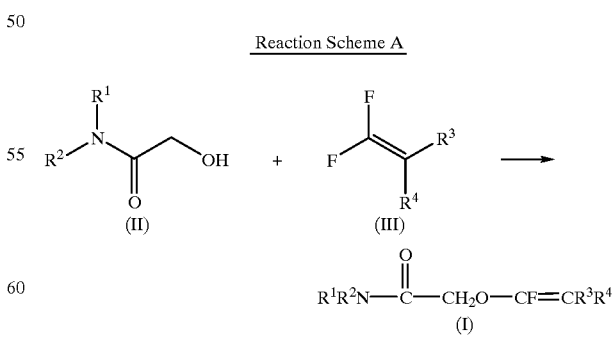

wherein $R^1$, $R^2$, $R^3$ and $R^4$ have the same meanings as defined in formula (I) above.

An alcoholic compound of formula (II) may be prepared by substitution, acetylation and hydrolysis of an amine of formula (VI) according to a conventional method(Hamm, P. C., *J. Amer. Chem. Soc.*, 78, 2556 (1956); Hartman, W. W. et al., *Org. Syn., Coll.*, 3, 650 (1955); and Brasen, W. R. et al., *Org. Syn. Coll.*, 4, 582 (1963)), as shown in Reaction Scheme B:

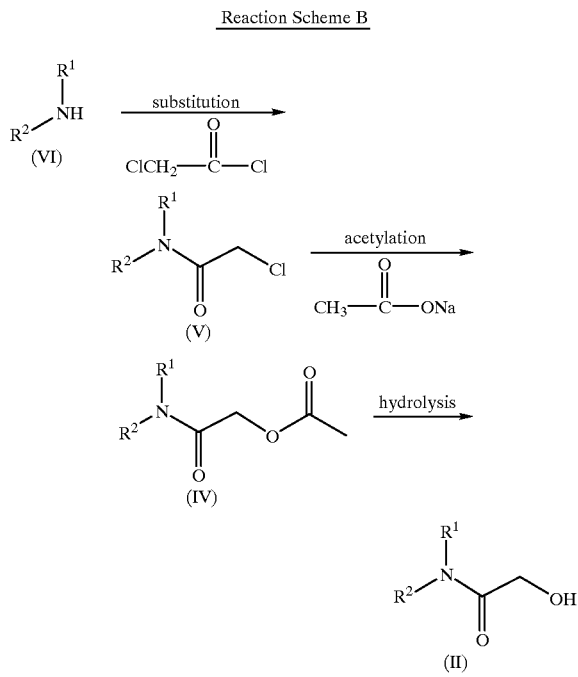

wherein $R^1$ and $R^2$ have the same meanings as defined in formula (I) above.

A difluorovinyl compound of formula (III) may be prepared form a halogen compound of formula (VIII) by Grignard and Wittig reactions(Herkes, F. E. et al., *J. Org. Chem.*, 32, 1311 (1967); and Wheaton, G. A. et al., *J. Org. Chem.*, 48, 917 (1983)), as shown in Reaction Scheme C:

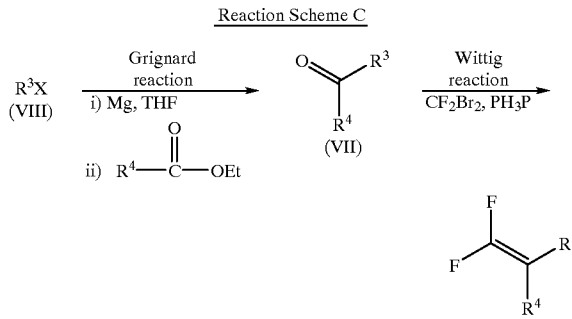

wherein X is Br or Cl; and $R^3$ and $R^4$ have the same meanings as defined in formula (I) above.

As shown in Reaction Scheme A, the fluorovinyloxyacetamide compound of the present invention may be prepared by reacting an alcoholic compound of formula (II) with a fluorovinyl compound of formula (III) in the presence of a base. Each of compounds of formula (II) and (III) may be used in equimolar amounts and the base may be used in one to two equivalent amounts. The base may be an inorganic base, e.g., sodium hydride, potassium hydride, potassium t-butoxide, sodium hydroxide, potassium hydroxide, sodium carbonate or potassium carbonate; or an organic base, e.g., triethylamine or pyridine. The solvent which may be used in the reaction is benzene, toluene, tetrahydrofuran, acetone, acetonitrile, dichloromethane, dimethylformamideor dimethylsulfoxide, individually or combined with water. The reaction may be conducted at a temperature ranging from room temperature to 100° C. The progress of the reaction is conveniently followed by measuring the disappearance of the compound of formula (II) with thin layer chromatography(TLC).

The compound of the present invention is obtained as a mixture of two isomers, i.e., the E and Z isomers.

For example, in the case of the compound of the present invention wherein $R^1$ is phenyl, $R^2$ is methyl, $R^3$ is phenyl and $R^4$ is $CF_3$(Compound 1), a 2:1 mixture of the Z and F isomers is obtained, the isomer ratio being determined on the basis of both $^1$H-NMR and $^{19}$F-NMR analysis of the product. Namely, the peak area ratio of the $^1$H-NMR peak for the methylene group of the Z isomer(a singlet at 4.30 ppm relative to $CHCl_3$) to that of E isomer(a singlet at 4.49 ppm) is about 2:1; and $^{19}$F-NMR analysis(reference compound: $CFCl_3$) shows a peak area ratio of about 2:1 when the peaks for the fluorine and $CF_3$ substituents of the Z isomer(a quartet having a coupling constant of 24.08 Hz at −84.99 ppm and a doublet having a coupling constant of 25.07 Hz at −57.36 ppm, respectively) are compared with those of the E isomer(a quartet having a coupling constant of 12.43 Hz at −83.40 ppm and a doublet having a coupling constant of 12.66 Hz at −57.95 ppm, respectively).

Likewise, the preparation of the compound of the present invention wherein $R^1$ and $R^2$ together with the nitrogen atom to which they are attached form a piperidino group, $R^3$ is phenyl and $R^4$ is $CF_3$(Compound 221) leads to a 2:1 mixture of the Z and E isomers. Namely, the peak area ratio of the 1H-NMR peak for the methylene group of the Z isomer(a singlet at 4.67 ppm) to that of the E isomer(a singlet 4.79 ppm) is about 2:1; and the $^{19}$F-NMR analysis(reference compound: $CFCl_3$) shows a peak area ratio of 2:1 when the peaks for the fluorine and $CF_3$ substituent of the Z isomer(a quartet having a coupling constant of 25.15 Hz at −84.28 ppm and a doublet having a coupling constant of 24.85 Hz at −57.38 ppm, respectively) are compared with those of the E isomer(a quartet having a coupling constant of 12.46 Hz at −82.24 ppm and a doublet having a coupling constant of 12.32 Hz at −57.83 ppm, respectively).

The compound of the present invention has herbicidal activity against a broad spectrum of weeds, in particular, against those belonging to the Gramineae family, e.g., rice(*Oryza sativa* L.), barnyardgrass(*Echinochlora crusgalli* 8P. BEAUV. var. oryzicola OHWI), bulrush(*Scirpus juncoides* ROXB), umbrellaplant(*Cyperus difformis* L.), flatsedge(*Cyperus serotinus* ROTTB), dayflower(*Aneilema keisak* HASSK), monochoria(*Monochoria vaginalis* PRESL), toothcup(*Rotala indica* KOEHE) and arrow head (*Sagittaria pygmaea* MIQ).

Accordingly, the present invention also includes within its scope a herbicidal composition comprising one or more of the compounds of formula (I) as an active ingredient, in association with herbicidally acceptable carriers.

The herbicidal composition of the invention may be formulated in various forms such as an emulsion, aqueous dispersion, powder and granules which may contain herbicidally acceptable carriers and additives. The compound of the formula (I) may be used in an amount of 10 to 90% on the basis of the weight of an emulsion or aqueous dispersion, 0.1 to 10% on the basis of the weight of powder, 1 to 30 % on the basis of the weight of granules.

Herbicidally acceptable carrier that may be used in the composition of the present invention is a liquid carrier, e.g., water, an alcohol(ethanol, ethylene glycol, glycerine), ketone(acetone, methylethylketone), ether(dioxane, tetrahydrofuran, cellosolve), aliphatic hydrocarbon (gasoline, Kerosene), halogenated hydrocarbon(chloroform, carbon tetrachloride), amide(dimethylformamide), ester (ethyl acetate, butyl acetate, fatty glycerine ester) and acetonitrile; and a solid carrier, e.g., mineral particle(Kaoline, clay, bentonite, dolomite, talc, silica, sand) and vegetable powder(shrubs).

The additive that may be used in the herbicidal composition of the present invention includes an emulsifier, adhesive, dispersion agent or permeating agent, e.g., nonionic, anionic or cationic interface active agent(fatty acid sodium salt, polyoxy alkyl ester, alkyl sulfonate ester). Further, an agrochemically active ingredient, e.g., an insecticide, fungicide, plant growth regulator, germicide, and fertilizer, may be added in the composition of the present invention.

The following Preparations and Examples are given for the purpose of illustration only and are not intended to limit the scope of the invention.

PREPARATION 1

Preparation of L-Methyl-2-hydroxyacetanilide(II)
Step 1: Preparation of N-Methyl-2-chloroacetanilide(V)

10.7 g(0.1 mol) of N-methylaniline(VI) was dissolved in 150 ml of dichloromethane containing 10.12 g(0.1 mol) of triethylamine, and 13.55 g(0.12 mol) of chloroacetylchloride was added dropwise thereto while cooling. The resulting solution was stirred at room temperature for 1 hour, and washed three times with water. The organic layer was dried and recrystallized in n-hexane to obtain 17.6 g(yield 96%) of the title compound as a yellowish brown solid.

$^1$H-NMR (CDCl$_3$, TMS) δ: 7.68–7.12(m, 5H), 3.92(s, 2H), 3.45(s, 3H); MS (m/e): 183(M$^+$, 37), 134(51), 106 (100), 90(52), 51(59). m.p.: 61–62° C.

Step 2 : Preparation of N-Methyl-2-acetoxyacetanilide(IV)

18.3 g(0.1 mol) of the compound obtained in Step 1 was added to 50 ml of dry dimethylformamide(DMF), and 9.8 g(0.12 mol) of sodium acetate was added thereto. The resulting solution was heated for 1 hour, cooled and 50 ml of water was added thereto. The resulting solution was extracted three times with ethyl acetate and the organic layer was dried. After removing the solvent, the residue was subjected to column chromatography using a mixture of n-hexane and ethyl acetate(9:1) as an eluent to obtain 19 g(yield 92%) of the title compound as a liquid.

$^1$H-NMR (CDCl$_3$, TMS) δ: 7.78–7.21(m, 5H), 4.48(s, 2H), 3.36(s, 3H), 2.21(s, 3H); MS (m/e): 207(M$^+$, 8), 107(61), 77(30), 43(100).

Step 3: Preparation of N-Methyl-2-hydroxyacetanilide(II)

20.7 g(0.1 mol) of the compound obtained in Step 2 was added to 100 ml of methanol, and 4.8 g(0.12 mol) of sodium hydroxide was added slowly thereto. The resulting solution was refluxed with heating for 1 hour. The solvent was removed under a reduced pressure and 50 ml of water was added thereto. The resulting solution was extracted three times with ethyl acetate. The organic layer was dried, the solvent was removed and the residue was recrystallized in n-hexane to obtain 14 g(yield 85%) of the title compound as a white solid.

$^1$H-NMR (CDCl$_3$, TMS) δ: 7.54–7.15(m, 5H), 3.82(d, 2H), 3.38(t, 1H), 3.32(s, 3H); MS (m/e): 165(M$^+$, 34), 134(41), 106(100), 77(81); m.p.: 41–42° C.

PREPARATIONS 2 to 31

The procedure of Preparation 1 was repeated to obtain compounds of formula (II) having various R$^1$ and R$^2$ groups, as in Table 1. The $^1$H-NMR and MS analysis data and melting points of these compounds are also shown in Table 1. L in Table 1 represents liquid.

TABLE 1

(II)

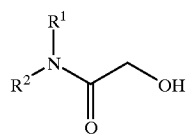

| Prep. No. | R$^1$ | R$^2$ | state(° C.) | NMR (CDCl$_3$, TMS) δ (ppm) | MS (m/e) |
|---|---|---|---|---|---|
| 1 | C$_6$H$_5$ | CH$_3$ | 41~42 | 7.54~7.15(m, 5H), 3.82(d, 2H), 3.38(t, 1H), 3.32(s, 3H) | 165(34), 134(41), 106(100), 77(81) |
| 2 | 4-CH$_3$O—C$_6$H$_4$ | CH$_3$ | 78~79 | 7.38~6.88(m, 4H), 3.85(s, 3H), 3.81(d, 2H), 3.40(t, 1H), 3.35(s, 3H) | 195(42), 136(100), 122(58) |
| 3 | 4-F—C$_6$H$_4$ | CH$_3$ | 105~106 | 7.36~7.04(m, 4H), 3.80(d, 2H), 3.40(t, 1H), 3.31(s, 3H) | 183(31), 152(45), 125(100), 95(28) |
| 4 | 4-Cl-C$_6$H$_4$ | CH$_3$ | 80~81 | 7.54~7.05(m, 4H), 3.84(d, 2H), 3.37(t, 1H), 3.34(s, 3H) | 199(41), 168(39), 140(100), 45(54) |
| 5 | 2, 4-F$_2$—C$_6$H$_3$ | CH$_3$ | 117~118 | 7.12~6.78(m, 3H), 4.35(b, 1H), 3.82(s, 2H), 3.29(s, 3H) | 201(46), 170(42), 142(100), 59(82) |
| 6 | 2, 4-Cl$_2$—C$_6$H$_3$ | CH$_3$ | 58~59 | 7.67~7.08(m, 3H), 3.81(d, 2H), 3.39(t, 1H), 3.38(s, 3H) | 233(23), 198(100), 174(79) |
| 7 | C$_6$H$_5$ | C$_2$H$_5$ | 38~39 | 7.56~7.02(m, 5H), 3.88(q, 2H), 3.83(d, 2H), 3.42(t, 1H), 1.20(t, 3H) | 179(21), 120(100), 106(73), 77(87) |
| 8 | 4-CH$_3$-C$_6$H$_4$ | C$_2$H$_5$ | 63~64 | 7.28~6.96(m, 4H), 3.78(q, 2H), 3.72(d, 2H), 3.42(t, 1H), 2.36(s, 3H), 1.12(t, 3H) | 193(47), 162(37), 134(100), 120(68), 91(50) |
| 9 | 4-CH$_3$O-C$_6$H$_4$ | C$_2$H$_5$ | 53~54 | 7.38~6.78(m, 4H), 3.86(s, 3H), 3.84(q, 2H), 3.83(d, 2H), 3.50(t, 1H), 1.18(t, 3H) | 209(77), 150(100), 136(78) |
| 10 | 3-CF$_3$-C$_6$H$_4$ | C$_2$H$_5$ | L | 7.95~7.20(m, 4H), 3.95(q, 2H), 3.80(d, 2H), 3.51(t, 1H), 1.18(t, 3H) | 247(31), 188(100), 174(92), 145(47) |
| 11 | 2-Cl-C$_6$H$_4$ | C$_2$H$_5$ | 47~48 | 7.75~7.05(m, 4H), 4.13(m, 1H), 3.82(m, 1H), 3.76(d, 2H), 3.48(t, 1H), 1.20(t, 3H) | 213(26), 178(100), 154(42), 140(42) |
| 12 | 3-Cl-C$_6$H$_4$ | C$_2$H$_5$ | L | 7.51~6.95(m, 4H), 3.86(q, 2H), 3.83(d, 2H), 3.53(t, 1H), 1.20(t, 3H) | 213(38), 182(57), 154(100), 140(79) |
| 13 | 4-Cl—C$_6$H$_4$ | C$_2$H$_5$ | 111~112 | 7.62~7.00(m, 4H), 3.86(q, 2H), 3.84(d, 2H), 3.55(t, 1H), | 213(36), 154(100), 140(84) |

TABLE 1-continued

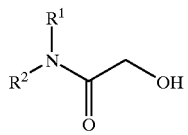

(II)

| Prep. No. | R¹ | R² | state(° C.) | NMR (CDCl₃, TMS) δ (ppm) | MS (m/e) |
|---|---|---|---|---|---|
| 14 | $C_6H_5$ | $n\text{-}C_3H_7$ | 58~59 | 7.62~6.98(m, 5H), 3.86(t, 2H), 3.80(d, 2H), 3.45(t, 1H), 1.85~1.20(m, 2H), 1.20(t, 3H) 1.23(t, 3H) | 193(23), 151(44), 106(100), 77(53) |
| 15 | $4\text{-}CH_3O\text{—}C_6H_4$ | $n\text{-}C_3H_7$ | 40~41 | 7.16~6.85(m, 4H), 3.84(s, 3H), 3.71(d, 2H), 3.65(t, 2H), 3.46(t, 1H), 1.63–1.46(m, 2H), 0.90(t, 3H) | 223(63), 150(40), 136(100), 43(47) |
| 16 | $C_6H_5$ | $i\text{-}C_3H_7$ | 42~43 | 7.48~6.88(m, 5H), 5.05~4.65(m, 1H), 3.64(d, 2H), 3.52(t, 1H), 1.02(d, 6H) | 193(24), 120(100), 77(52), 43(100) |
| 17 | $2\text{-}CH_3\text{—}C_6H_4$ | $i\text{-}C_3H_7$ | L | 7.48~6.98(m, 4H), 5.12~4.64(m, 1H), 3.62(d, 2H), 3.34(t, 1H), 2.37(s, 3H), 1.28(d, 3H), 1.00(d, 3H) | 207(47), 134(100), 45(89) |
| 18 | $3\text{-}CH_3\text{—}C_6H_4$ | $i\text{-}C_3H_7$ | 51~52 | 7.49~6.85(m, 4H), 5.15~4.72(m, 1H), 3.72(d, 2H), 3.55(t, 1H), 2.48(s, 3H), 1.08(d, 6H) | 207(48), 134(94), 91(72), 45(100) |
| 19 | $3\text{-}CH_3O\text{—}C_6H_4$ | $i\text{-}C_3H_7$ | L | 7.41~6.61(m, 4H), 5.08~4.84(m, 1H), 3.84(s, 3H), 3.69(d, 2H), 3.57(t, 1H), 1.08(d, 6H) | 223(18), 150(100), 84(26), 45(38) |
| 20 | $4\text{-}CH_3O\text{—}C_6H_4$ | $i\text{-}C_3H_7$ | 96~97 | 7.32~6.78(m, 4H), 5.25~4.76(m, 1H), 3.86(s, 3H), 3.68(d, 2H), 3.51(t, 1H), 1.10(d, 6H) | 223(27), 181(47), 150(100), 123(79), 107(65), 45(54) |
| 21 | $3\text{-}CF_3\text{—}C_6H_4$ | $i\text{-}C_3H_7$ | 48~49 | 7.87~7.21(m, 4H), 5.18~4.86(m, 1H), 3.76(d, 2H), 3.51(t, 1H), 1.08(d, 6H) | 261(26), 188(63), 43(100) |
| 22 | $4\text{-}F\text{—}C_6H_4$ | $i\text{-}C_3H_7$ | 52~53 | 7.21~7.03(m, 4H), 5.08~4.86(m, 1H), 3.61(d, 2H), 3.45(t, 1H), 1.07(d, 6H) | 211(20), 138(100), 95(33), 43(86) |
| 23 | $2\text{-}Cl\text{—}C_6H_4$ | $i\text{-}C_3H_7$ | 67~68 | 7.78~7.23(m, 4H), 5.16~4.85(m, 1H), 3.78(d, 2H), 3.50(t, 1H), 1.35(d, 3H), 1.20(d, 3H) | 227(8), 192(69), 154(83), 45(100) |
| 24 | $3\text{-}Cl\text{—}C_6H_4$ | $i\text{-}C_3H_7$ | 62~63 | 7.58~6.95(m, 4H), 5.15~4.85(m, 1H), 3.80(d, 2H), 3.54(t, 1H), 1.08(d, 6H) | 227(27), 154(100), 43(76) |
| 25 | $2\text{-}Cl\text{-}4\text{-}F\text{—}C_6H_3$ | $i\text{-}C_3H_7$ | 51~52 | 7.51~7.15(m, 3H), 5.14~4.87(m, 1H), 3.78(d, 2H), 3.48(t, 1H), 1.32(d, 3H), 1.15(d, 3H) | 245(19), 210(24), 172(28), 43(100) |
| 26 | $3,4\text{-}Cl_2\text{—}C_6H_3$ | $i\text{-}C_3H_7$ | 67~68 | 7.72~6.97(m, 3H), 5.12~4.84(m, 1H), 3.75(d, 2H), 3.46(t, 1H), 1.16(d, 6H) | 261(36), 188(28), 45(100) |
| 27 | $3\text{-}CH_3\text{—}C_6H_4$ | $CH_3$ | L | 7.42~6.84(m, 4H), 3.82(d, 2H), 3.41(t, 1H), 3.32(s, 3H), 2.37(s, 3H) | 179(61), 120(100), 59(67) |
| 28 | $4\text{-}CH_3\text{—}C_6H_4$ | $CH_3$ | 58 | 7.38~6.87(m, 4H), 3.81(d, 2H), 3.38(t, 1H), 3.31(s, 3H), 2.35(s, 3H) | 179(47), 120(100), 59(86) |
| 29 | $3,4\text{-}(CH_3)_2\text{—}C_6H_3$ | $CH_3$ | 80 | 7.37~6.84(m, 3H), 3.82(d, 2H), 3.36(t, 1H), 3.33(s, 3H), 2.25(s, 6H) | 193(57), 134(100) |
| 30 | $3\text{-}Cl\text{—}C_6H_4$ | $CH_3$ | 66 | 7.67~7.01(m, 4H), 3.84(d, 2H), 3.53(t, 1H), 3.36(s, 3H) | 199(58), 140(100), 75(82) |
| 31 | $3,4\text{-}(CH_3)_2\text{—}C_6H_3$ | $i\text{-}C_3H_7$ | L | 7.43~6.85(m, 3H), 5.32~4.84(m, 1H), 3.70(d, 2H), 3.31(t, 1H), 2.34(s, 6H), 1.18(d, 6H) | 221(61), 162(100), 59(48) |

PREPARATION 32

Preparation of N-2-Hydroxyacetylpiperidine(II)

Step 1: Preparation of N-2-Chloroacetylpiperidine(V)

The procedure of Step 1 of Preparation 1 was repeated except that 8.5 g of piperidine was used in place of N-methylaniline and that column chromatography using a mixture of n-hexane and ethyl acetate(4:1) as an eluent was conducted in place of recrystallization to obtain 14.8 g(yield 92%) of the title compound as a yellowish brown liquid.

¹H-NMR (CDCl₃, TMS) δ: 4.08(s, 2H), 3.76–3.18(m, 4H), 1.98–1.21(m, 6H); MS (m/e): 161(M⁺, 26), 126(100), 69(37), 41(68).

Step 2: Preparation of N-2-Acetoxyacetylpiperidine(IV)

The procedure of Step 2 of Preparation 1 was repeated except that 16.1 g(0.1 mol) of the compound obtained in Step 1 was used and that column chromatography was conducted using a 4:1 mixture of n-hexane and ethyl acetate as an eluent to obtain 16.5 g(yield 89%) of the title compound as a liquid.

¹H-NMR (CDCl₃, TMS) δ: 4.67(s, 2H), 3.68–3.10(m, 4H), 2.12(s, 3H), 1.68–1.38(m, 6H); MS (m/e): 185(M⁺, 21), 112(51), 69(73), 43(100).

Step 3: Preparation of N-2-Hydroxyacetylpiperidine(II)

The procedure of Step 3 of Preparation 1 was repeated except that 18.5 g of the compound obtained in Step 2 was used and that column chromatography using a 2:1 mixture of n-hexane and ethyl acetate as an eluent was conducted in place of recrystallization to obtain 11.7 g(yield 82%) of the title compound.

¹H-NMR (CDCl₃, TMS) δ: 4.08(d, 2H), 3.97(t, 1H), 3.67–3.02(m, 4H), 1.75–1.15(m, 6H), MS (m/e): 143(M⁺, 35), 112(86), 69(77), 43(100).

PREPARATIONS 33 to 48

The procedure of Preparation 32 was repeated to obtain compounds of formula (II) having various R¹ and R² groups, as in Table 2. The ¹H-NMR and MS analysis data and melting points of these compounds are also shown in Table 2. L in Table 2 represents liquid.

TABLE 2

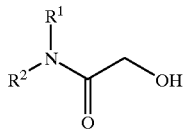

(II)

| Prep. No. | R¹ | R² | state (° C.) | NMR (CDCl₃, TMS) δ (ppm) | MS (m/e) |
|---|---|---|---|---|---|
| 32 | —(CH₂)₅— | | L | 4.08(d, 2H), 3.97(t, 1H), 3.67~3.02(m, 4H), 1.75~1.15(m, 6H) | 143(35), 112(86), 69(77), 43(100) |
| 33 | —CH(CH₃)(CH₂)₄— | | L | 4.12(d, 2H), 3.85(t, 1H), 3.46~2.67(m, 3H), 1.94~1.46(m, 6H), 1.23(d, 3H) | 157(37), 126(72), 84(100), 55(66) |
| 34 | —CH(CH₃CH₂)(CH₂)₄— | | L | 4.13(d, 2H), 4.08(t, 1H), 3.45~2.64(m, 3H), 1.85~1.38(m, 8H), 0.86(t, 3H) | 171(16), 142(38), 84(100), 55(48) |
| 35 | —CH(CH₃)(CH₂)₃CH(CH₃)— | | L | 4.71(b, 1H), 4.15(d, 2H), 3.98~3.54(m, 2H), 1.97~1.46(m, 6H), 1.25(d, 6H) | 171(28), 98(97), 55(99), 41(100) |
| 36 | —(CH₂)₂CH=CHCH₂— | | 77~78 | 5.86~5.69(m, 2H), 4.16(d, 2H), 4.15(t, 1H), 3.75~3.64(m, 2H), 3.30(t, 2H), 2.27~2.05(m, 2H) | 141(39), 82(57), 67(86), 54(83), 41(100) |
| 37 | —(CH₂)₂O(CH₂)₂— | | 52~53 | 4.13(d, 2H), 3.80~3.48(m, 8H), 3.41(1, 1H) | 145(75), 100(67), 86(55), 42(100) |
| 38 | —(CH₂)₃C(C₄H₄)C— | | 78~79 | 7.28~7.03(m, 4H), 4.18(d, 2H), 3.80(t, 1H), 3.78~3.54(m, 2H), 2.75(t, 2H), 1.98(t, 2H) | 191(36), 132(100), 117(30), 77(49) |
| 39 | —(CH₂)₆— | | L | 4.15(d, 2H), 3.84(t, 1H), 3.78~3.12(m, 4H), 1.98~1.28(m, 5H) | 157(11), 126(72), 84(100), 47(79) |
| 40 | C₂H₅ | C₂H₅ | L | 4.05(d, 2H), 3.78(t, 1H), 3.48(q, 2H), 3.23(q, 2H), 1.15(t, 6H) | 131(25), 100(71), 72(100), 44(86) |
| 41 | n-C₃H₇ | n-C₃H₇ | L | 4.06(d, 2H), 3.80(t, 1H), 3.42(q, 2H), 3.15(q, 2H), 1.85~1.15(m, 4H), 0.97(t, 6H) | 159(23), 86(29), 72(100), 43(94) |
| 42 | i-C₃H₇ | i-C₃H₇ | 63~64 | 4.08(d, 2H), 3.95(t, 1H), 3.84~3.35(m, 2H), 1.42(d, 6H), 1.28(d, 6H) | 159(45), 128(36), 86(94), 43(100) |
| 43 | CH₂=CHCH₂ | CH₂=CHCH₂ | L | 6.12~5.02(m, 6H), 4.12(d, 2H), 4.01~3.94(m, 4H), 3.65(t, 1H) | 155(36), 124(27), 56(37), 41(100) |
| 44 | n-C₄H₉ | n-C₄H₉ | L | 4.14(d, 2H), 3.72(t, 1H), 3.36(t, 4H), 1.64~1.19(m, 8H), 0.96(t, 6H) | 187(21), 86(57), 57(100), 44(58) |
| 45 | i-C₄H₉ | i-C₄H₉ | L | 4.12(d, 2H), 3.74(t, 1H), 3.24(d, 4H), 2.13~1.78(m, 2H), 0.87(d, 12H) | 187(44), 144(31), 86(100), 57(69) |
| 46 | C₂H₅ | i-C₃H₇ | L | 4.14(d, 2H), 3.81(t, 1H), 3.75~3.56(m, 1H), 3.27(q, 2H), 1.18(d, 6H), 1.15(t, 3H) | 145(11), 86(38), 72(97), 43(100) |
| 47 | CH₃ | n-C₄H₉ | L | 4.08(d, 2H), 3.79(t, 1H), 3.45(t, 2H), 2.85(s, 3H), 1.78~1.08(m, 4H), 0.98(t, 3H) | 145(12), 114(21), 57(41), 44(100) |
| 48 | CH₃ | C₆H₅CH₂ | L | 7.25~7.09(m, 5H), 5.45(t, 1H), 4.58(s, 2H), 4.38(d, 2H), 2.98(s, 3H) | 179(48), 120(87), 59(100) |

PREPARATION 49

Preparation of 2,2-Difluoro-1-trifluoromethyl-4'-methoxy styrene(III)

Step 1: Preparation of 2,2,2-Trifluoromethyl-4'-methoxyphenylketone(VII)

5.1 g(0.21 g atom) of magnesium was placed in 300 ml of dry diethyl ether and 37.4 g(0.2 mol) of p-bromoanisole was added dropwise thereto under a nitrogen atmosphere to prepare a Grignard reagent. The Grignard reagent solution was cooled to −78° C. and 28.4 g(0.2 mol) of ethyl trifluoroacetate was added dropwise thereto. The resulting solution was stirred for 30 to 60 minutes, mixed with crushed ice, acidified with concentrated hydrochloric acid and then extracted three times with diethyl ether. The organic layer was dried over magnesium sulfate and the solvent was removed under a reduced pressure to obtain a residue. The residue was distilled at 72 to 73° C./20 mmHg to obtain 35.09 g (yield 86%) of the title compound as a colorless oil.

¹H-NMR (CDCl₃, TMS) δ: 7.62–6.81(m, 4H), 3.86(s, 3H); MS (m/e): 204(M⁺, 56), 135(100), 107(86), 92(66), 77(92).

Step 2: Preparation of 2,2-Difluoro-1-trifluoromethyl-4'-methoxy Styrene(III)

26.2 g(0.1 mol) of triphenylphosphine was dissolved in 250 ml of dry THF and 25.2 g(0.12 mol) of dibromodifluoromethane was added dropwise thereto under a nitrogen atmosphere at a temperature below 10° C. The resulting solution was stirred for thirty minutes and 10.2 g(0.05 mol) of the compound obtained in Step 1 was added thereto. The resultant solution was refluxed for 12 hours, cooled and distilled under a reduced pressure. The product was redistilled at 72 to 74° C. at 10 mmHg to obtain 9.36 g(yield 78.7%) of the title compound as a colorless liquid.

¹H-NMR (CDCl₃, TMS) δ: 7.48–6.79(m, 4H), 3.79(s, 3H); MS (m/e): 238(M⁺, 69), 195(14), 145(35), 74(33), 59(100).

PREPARATIONS 50 to 65

The procedure of Preparation 49 was repeated to obtain compounds of formulas (VII) and (III) having various R³ and R⁴ groups, as in Tables 3a and 3b, respectively. The ¹H-NMR and MS analysis data and melting points of these compounds are also shown in respective tables.

PREPARATION 66

Preparation of 2,2-Difluoro-1-pentafluoroethyl styrene(III)

The procedure of Preparation 49 was repeated except that bromobenzene and ethyl pentafluoropropionate were used in place of bromoanisole and ethyl trifluoroacetate, respectively, to obtain the title compound. The ¹H-NMR and MS analysis data and melting points of the compounds of formulas (VII) and (III) are also shown in Tables 3a and 3b, respectively.

TABLE 3a

(VII)

Prep. Nos. 49–65: $R^4 = CF_3$
Prep. No. 66: $R^4 = CF_2CF_3$

| Prep. No. | $R^3$ | $^1$H-NMR(CDCl$_3$, TMS) δ (ppm) | MS (m/e) | yield (%) | b.p. (mmHg) |
|---|---|---|---|---|---|
| 49 | 4-CH$_3$O—C$_6$H$_4$— | 7.62~6.81(m, 4H), 3.86(s, 3H) | 204(56), 135(100), 107(86), 92(66), 77(92) | 86 | 72~73 (20) |
| 50 | 3-CH$_3$—C$_6$H$_4$— | 7.52~6.92(m, 4H), 2.25(s, 3H) | 188(16), 135(45), 119(96), 91(100), 65(45) | 61 | 70~71 (20) |
| 51 | 4-CH$_3$—C$_6$H$_4$— | 7.42~6.92(m, 4H), 2.25(s, 3H) | 188(12), 119(100), 91(96), 65(45) | 68 | 65~66 (8) |
| 52 | 4-C$_2$H$_3$—C$_6$H$_4$— | 7.46~7.19(m, 4H), 2.68(q, 2H), 1.23(t, 3H) | 202(40), 133(91), 105(100), 76(64) | 62 | column |
| 53 | 3,4-(CH$_3$)$_2$—C$_6$H$_3$— | 7.52~6.69(m, 3H), 2.23(s, 3H), 2.20(s, 3H) | 202(43), 133(98), 69(100) | 71 | column |
| 54 | 3,5-(CH$_3$)$_2$—C$_6$H$_3$— | 7.31~7.01(m, 3H), 2.25(s, 6H) | 202(24), 133(100), 69(24) | 69 | column |
| 55 | 3-CH$_3$O—C$_6$H$_4$— | 7.41~6.79(m, 4H), 3.79(s, 3H) | 204(36), 135(100), 107(56), 77(94) | 78 | 64~65 (33) |
| 56 | C$_6$H$_5$— | 7.52~7.12(m, 5H) | 174(21), 105(100), 77(82), 69(54) | 71 | 64~65 (33) |
| 57 | 4-C$_2$H$_5$O—C$_6$H$_4$— | 7.54~6.76(m, 4H), 4.09(q, 2H), 1.32(t, 3H) | 218(16), 149(88), 121(62), 76(100) | 69 | column |
| 58 | 3,4-OCH$_2$O—C$_6$H$_4$— | 7.92~7.43(m, 3H), 6.25~6.01(s, 2H) | 218(42), 149(100), 65(49) | 73 | column |
| 59 | 3-CF$_3$—C$_6$H$_4$— | 8.60~7.61(m, 4H) | 242(10), 173(68), 145(100), 76(62) | 67 | column |
| 60 | 3-F—C$_6$H$_4$— | 7.56~6.89(m, 4H) | 192(25), 123(100), 95(78), 75(31) | 54 | 59~60 (30) |
| 61 | 4-F—C$_6$H$_4$— | 7.76~6.92(m, 4H) | 192(16), 169(54), 123(100), 95(91), 75(76) | 59 | 66~67 (34) |
| 62 | 3-Cl—C$_6$H$_4$— | 8.38~7.45(m, 4H) | 208(10), 139(93), 111(100), 75(64) | 70 | 58~59 (10) |
| 63 | 4-Cl—C$_6$H$_4$— | 7.51~7.41(m, 4H) | 208(100), 173(92), 97(54), 69(24) | 61 | 83~84 (24) |
| 64 | 3,5-Cl$_2$—C$_6$H$_3$— | 8.12~7.86(m, 3H) | 242(55), 173(100), 145(64), 109(32) | 45 | 75~76 (4) |
| 65 | C$_4$H$_3$S-2-yl- | 8.28~7.28(m, 3H) | 180(23), 111(45), 84(100) | 76 | column |
| 66 | C$_6$H$_5$ | 7.48~7.02(m, 5H) | 224(48), 205(100), 119(75) | 68 | 62~63(22) |

TABLE 3b

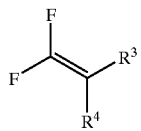

(III)

Prep. Nos. 49–65: $R^4 = CF_3$
Prep. No. 66: $R^4 = CF_2CF_3$

| Prep. No. | $R^3$ | $^1$H-NMR(CDCl$_3$, TMS) δ (ppm) | MS (m/e) | yield (%) | b.p. (mmHg) |
|---|---|---|---|---|---|
| 49 | 4-CH$_3$O—C$_6$H$_4$— | 7.48~6.79(m, 4H), 3.79(s, 3H) | 238(69), 195(14), 145(35), 74(33), 59(100) | 79 | 72~74 (10) |
| 50 | 3-CH$_3$—C$_6$H$_4$— | 7.46~6.98(m, 4H), 2.43(s, 3H) | 222(20), 203(70), 134(100) | 45 | column |
| 51 | 4-CH$_3$—C$_6$H$_4$— | 7.32~7.18(m, 4H), 2.45(s, 3H) | 222(64), 203(23), 134(100) | 62 | column |
| 52 | 4-C$_2$H$_3$—C$_6$H$_4$— | 7.38~7.25(m, 4H), 2.68(q, 2H), 1.19(t, 3H) | 236(20), 145(100), 90(54) | 62 | column |
| 53 | 3,4-(CH$_3$)$_2$—C$_6$H$_4$— | 7.28~7.02(m, 3H), 2.38(s, 3H), 2.32(s, 3H) | 236(18), 84(33), 45(100) | 78 | column |
| 54 | 3,5-(CH$_3$)$_2$—C$_6$H$_4$— | 7.32~7.12(m, 3H), 2.41(s, 6H) | 236(29), 217(65), 148(100), 45(92) | 63 | column |
| 55 | 3-CH$_3$O—C$_6$H$_4$— | 7.48~6.87(m, 4H), 3.81(s, 3H) | 238(42), 207(45), 188(37), 139(100), 69(94) | 54 | 75 (10) |
| 56 | C$_6$H$_5$— | 7.59~7.31(m, 5H) | 208(48), 84(83), 43(100) | 67 | column |
| 57 | 4-C$_2$H$_5$O—C$_6$H$_4$— | 7.51~6.85(m, 4H), 4.12(q, 2H), 1.29(t, 3H) | 252(47), 233(100), 84(64) | 73 | column |
| 58 | 3,4-OCH$_2$O—C$_6$H$_4$— | 7.01~6.79(m, 3H), 6.01(s, 2H) | 252(46), 233(63), 164(82), 69(100) | 72 | column |
| 59 | 3-CF$_3$—C$_6$H$_4$— | 7.82~7.18(m, 4H) | 276(52), 257(92), 188(100) | 52 | column |
| 60 | 3-F—C$_6$H$_4$— | 7.53~6.96(m, 4H) | 226(52), 207(25), 54(100) | 54 | column |
| 61 | 4-F—C$_6$H$_4$— | 7.52~6.83(m, 4H) | 226(20), 84(100) | 63 | column |
| 62 | 3-Cl—C$_6$H$_4$— | 7.54~7.23(m, 4H) | 242(26), 223(72), 188(49), 169(100) | 63 | column |
| 63 | 4-Cl—C$_6$H$_4$— | 7.56~7.21(m, 4H) | 242(35), 207(25), 174(70), 139(100), 60(79) | 45 | 58 (10) |
| 64 | 3,5-Cl$_2$—C$_6$H$_5$— | 7.57~7.19(m, 3H) | 276(100), 241(45) | 84 | 85 (10) |
| 65 | C$_4$H$_3$S-2-yl- | 7.67~6.92(m, 3H) | 214(42), 195(92), 126(100), 47(86) | 63 | column |
| 66 | C$_6$H$_5$ | 7.57~6.89(m, 5H) | 246(67), 227(57), 127(100), 119(35) | 48 | 138~139(737) |

EXAMPLE 1

Preparation of N-Methyl-(2'-fluoro-1'-trifluoromethylstyryl-2'-oxy)acetanilide (Compound 1)

330 mg(2 mmol) of N-methyl-2-hydroxyacetanilide obtained in Preparation 1 was added to 10 ml of acetone and 0.22 ml of 10M sodium hydroxide solution(2.2 mmol) was added thereto. The resulting solution was stirred for 30 minutes and 416 mg(2 mmol) of 2,2-difluoro-1-trifluoromethyl styrene obtained in Preparation 56 was added slowly thereto. The resultant solution was stirred for 1 to 2 hours. Acetone was removed under a reduced pressure and the resulting solution was mixed with water and extracted with ethyl acetate. The organic layer was dried over magnesium sulfate and the solvent was removed under a reduced pressure. The residue was subjected to silica gel column chromatography using a mixture of n-hexane and ethyl acetate (9:1) as an eluent to obtain 655 mg(yield 92.8%) of the title compound having two isomers as a colorless liquid. 1H-NMR (CDCl$_3$TMS) δ: 7.52–6.91(m, 10H), 4.49(E isomer) 4.30(Z isomer)(s, 2H), 3.30(s, 3H)

MS (m/e): 353(M$^+$, 12), 177(42), 120(100), 91(72), 77(96) $^{19}$F-NMR (CDCl$_3$, CFCl$_3$) δ: −57.36(Z isomer) −57.95(E isomer)(d, 3F), −83.40(E, isomer) −84.99(Z isomer)(q, 1F)

EXAMPLE 2

Preparation of (E)-N-Methyl-(2'-fluoro-1'-trifluoromethylstyryl-2'-oxy)acetanilide (Compound 2)

The compound obtained in Example 1 was subjected to column chromatography using a mixture of n-hexane and ethyl acetate(9:1) as an eluent to isolate a pure form of the E isomer as a colorless solid.

E isomer; $^1$H-NMR (CDCl$_3$, TMS) δ: 7.54–6.90(m, 10H), 4.49(s, 2H), 3.31(s, 3H); MS (m/e): 353(M$^+$, 43), 177(48), 120(100), 91(68), 7(82); $^{19}$F-NMR (CDCl$_3$, CFCl$_3$) δ: −57.95(d, 3F), −83.40(q, 1F) m.p.: 91–92° C.

EXAMPLE 3

Preparation of (Z)-N-Methyl-(2'-fluoro-1'-trifluoromethylstyryl-2'-oxy)acetanilide (Compound 3)

The compound obtained in Example 1 was subjected to column chromatography using a mixture of n-hexane and ethyl acetate(9:1) as an eluent to isolate a pure form of the Z isomer as a colorless oil.

Z isomer; $^1$H-NMR (CDCl$_3$, TMS) δ: 7.51–7.11(m, 10H), 4.30(s, 2H), 3.30(s, 3H); MS (m/e): 353(M$^+$, 57), 177(40), 120(100), 91(70), 77(97); $^{19}$F-NMR (CDCl$_3$, CFCl$_3$) δ: −57.36(d, 3F), −84.99(q, 1F).

EXAMPLES 4 to 220

Using each of the alcoholic compounds obtained in Preparations 1 to 31 and each of the fluorovinyl compounds obtained in Preparations 49 to 66, the procedure of Example 1 was repeated to obtain 217 compounds(Compounds 4 to 220) of formula (I) of the present invention having various R$^1$, R$^2$, R$^3$ and R$^4$ groups listed in Table 4. The $^1$H-NMR and MS data and melting points of these compounds are also shown in Table 4. L in Table 4 represents liquid.

TABLE 4

$$\underset{R^2}{\overset{R^1}{N}}\underset{\underset{O}{\parallel}}{C}CH_2O-\underset{F}{C}=\underset{R^4}{C}\underset{R^3}{\overset{R^3}{}}\quad R^4=CF_3 \quad (I)$$

| Comp. No. | R¹ | R² | R³ | state (° C.) | NMR (CDCl₃, TMS) δ (ppm) | MS (m/e) |
|---|---|---|---|---|---|---|
| 1 | C₆H₅ | CH₃ | C₆H₅ | L | 7.52~6.91(m, 10H), 4.49(E) 4.30(Z) (s, 2H), 3.30(s, 3H) | 353(12), 177(42), 120(100), 91(72), 77(96) |
| 2 | C₆H₅ | CH₃ | C₆H₅ | 91–92 | 7.54~6.90(m, 10H), 4.49(s, 2H), 3.31(s, 3H) | 353(43), 177(48), 120(100), 91(68), 77(82) |
| 3 | C₆H₅ | CH₃ | C₆H₅ | L | 7.51~7.11(m, 10H), 4.30(s, 2H), 3.30(s, 3H) | 353(57), 177(40), 120(100), 91(70), 77(97) |
| 4 | C₆H₅ | CH₃ | 3-CH₃—C₆H₄ | L | 7.51~6.98(m, 9H), 4.48(E) 4.31(Z) (s, 2H), 3.31(s, 3H), 2.35(s, 3H) | 367(45), 148(100), 120(54), 91(37) |
| 5 | C₆H₅ | CH₃ | 4-CH₃—C₆H₄ | L | 7.54~6.89(m, 9H), 4.49(E) 4.31(Z) (s, 2H), 3.32(s, 3H), 2.34(s, 3H) | 367(28), 148(100), 120(68), 92(52) |
| 6 | C₆H₅ | CH₃ | 4-C₂H₅—C₆H₄ | L | 7.57~7.01(m, 9H), 4.48(E) 4.30(Z) (s, 2H), 3.30(s, 3H), 2.64(q, 2H), 1.21(t, 3H) | 381(68), 148(100), 120(75), 91(74), 77(76) |
| 7 | C₆H₅ | CH₃ | 3,4-(CH₃)₂—C₆H₃ | L | 7.51~7.02(m, 8H), 4.49(E) 4.31(Z) (s, 2H), 3.31(s, 3H), 2.30(s, 6H) | 381(25), 148(92), 120(100), 91(46), 77(59) |
| 8 | C₆H₅ | CH₃ | 3,5-(CH₃)₂—C₆H₃ | L | 7.58~6.85(m, 8H), 4.48(E) 4.29(Z) (s, 2H), 3.32(s, 3H), 2.31(s, 6H) | 381(25), 148(100), 120(59), 92(28) |
| 9 | C₆H₅ | CH₃ | 3-CH₃O—C₆H₄ | L | 7.65~6.79(m, 9H), 4.30(E) 4.31(Z) (s, 2H), 3.86(s, 3H), 3.33(s, 3H) | 383(46), 364(28), 148(100), 120(99) |
| 10 | C₆H₅ | CH₃ | 4-CH₃O—C₆H₄ | L | 7.66~6.81(m, 9H), 4.49(E) 4.31(Z) (s, 2H), 3.86(s, 3H), 3.32(s, 3H) | 383(51), 207(55), 148(100), 120(59) |
| 11 | C₆H₅ | CH₃ | 4-C₂H₅O—C₆H₄ | L | 7.42~6.80(m, 9H), 4.48(E) 4.30(Z) (s, 2H), 3.98(q, 2H), 3.32(s, 3H), 1.39(t, 3H) | 397(49), 249(30), 148(100), 120(81) |
| 12 | C₆H₅ | CH₃ | 3,4-OCH₂O—C₆H₃ | L | 7.68~6.82(m, 8H), 5.92(s, 2H), 4.49(E) 4.30(Z) (s, 2H), 3.33(s, 3H) | 397(35), 148(100), 120(70), 77(43) |
| 13 | C₆H₅ | CH₃ | 3-CF₃—C₆H₄ | L | 7.68~6.91(m, 9H), 4.48(E) 4.31(Z) (s, 2H), 3.31(s, 3H) | 421(35), 402(19), 148(100), 120(99), 91(54) |
| 14 | C₆H₅ | CH₃ | 3-F—C₆H₄ | L | 7.62~6.99(m, 9H), 4.49(E) 4.31(Z) (s, 2H), 3.32(s, 3H) | 371(40), 148(100), 120(91), 96(41), 77(37) |
| 15 | C₆H₅ | CH₃ | 4-F—C₆H₄ | L | 7.68~6.98(m, 9H), 4.48(E) 4.30(Z) (s, 2H), 3.33(s, 3H) | 371(30), 148(100), 120(78), 77(42) |
| 16 | C₆H₅ | CH₃ | 3-Cl—C₆H₄ | L | 7.72~7.01(m, 9H), 4.49(E) 4.30(Z) (s, 2H), 3.34(s, 3H) | 387(62), 148(100), 120(45), 77(47) |
| 17 | C₆H₅ | CH₃ | 4-Cl—C₆H₄ | L | 7.65~6.98(m, 9H), 4.48(E) 4.31(Z) (s, 2H), 3.35(s, 3H) | 387(59), 148(100), 120(95), 91(46) |
| 18 | C₆H₅ | CH₃ | 3,5-Cl₂—C₆H₃ | L | 7.52~7.09(m, 8H), 4.49(E) 4.32(Z) (s, 2H), 3.31(s, 3H) | 421(25), 148(100), 120(84), 77(48) |
| 19 | C₆H₅ | CH₃ | C₄H₃S-2-yl | L | 7.62~6.95(m, 8H), 4.49(E) 4.32(Z) (s, 2H), 3.32(s, 3H) | 359(10), 148(100), 120(58), 77(15) |
| 20 | 4-CH₃O—C₆H₄ | CH₃ | C₆H₅ | L | 7.52~6.87(m, 9H), 4.49(E) 4.31(Z) (s, 2H), 3.85(s, 3H) | 383(12), 178(100), 144(81) |

TABLE 4-continued structure: R¹R²N-C(=O)-CH₂-O-C(F)=C(R³)(R⁴), R⁴ = CF₃ (I)

| Comp. No. | R¹ | R² | R₃ | state (° C.) | NMR (CDCl₃, TMS) δ (ppm) | MS (m/e) |
|---|---|---|---|---|---|---|
| 21 | 4-CH₃O—C₆H₄ | CH₃ | 3-CH₃—C₆H₄ | L | 7.43~6.76(m, 8H), 4.48(E) 4.29(Z) (s, 2H), 3.85(s, 3H) 3.31(s, 3H), 2.35(s, 3H) 3.32(s, 3H) | 397(47), 178(100), 147(40) 121(48) |
| 22 | 4-CH₃O—C₆H₄ | CH₃ | 4-CH₃—C₆H₄ | L | 7.49~6.79(m, 8H), 4.48(E) 4.28(Z) (s, 2H), 3.84(s, 3H) 3.31(s, 3H), 2.35(s, 3H) | 397(100), 372(33), 178(98), 150(53) |
| 23 | 4-CH₃O—C₆H₄ | CH₃ | 3,4-(CH₃)₂—C₆H₃ | 81~82 | 7.55~6.79(m, 7H), 4.49(E) 4.29(Z) (s, 2H), 3.85(s, 3H) 3.33(s, 3H), 2.31(s, 6H) | 411(40), 178(100), 147(69) |
| 24 | 4-CH₃O—C₆H₄ | CH₃ | 3,5-(CH₃)₂—C₆H₃ | L | 7.62~6.78(m, 7H), 4.49(E) 4.30(Z) (s, 2H), 3.86(s, 3H) 3.32(s, 3H), 2.30(s, 6H) | 411(51), 178(100), 147(47), 121(36) |
| 25 | 4-CH₃O—C₆H₄ | CH₃ | 3-CH₃—C₆H₄ | L | 7.56~6.72(m, 8H), 4.49(E) 4.32(Z) (s, 2H), 3.87(s, 3H) 3.85(s, 3H), 2.30(s, 3H) | 413(24), 178(100), 147(37) |
| 26 | 4-CH₃O—C₆H₄ | CH₃ | 3,4-OCH₂O—C₆H₃ | L | 7.59~6.52(m, 7H), 5.94(s, 2H), 4.49(E) 4.31(Z) (s, 2H), 3.86(s, 3H), 3.31(s, 3H) | 427(41), 178(100), 147(25), 121(24) |
| 27 | 4-CH₃O—C₆H₄ | CH₃ | 3,5-Cl—C₆H₄ | L | 7.56~6.85(m, 8H), 4.49(E) 4.30(Z) (s, 2H), 3.86(s, 3H) 3.34(s, 3H) | 417(18), 178(100), 147(46), 121(41) |
| 28 | 4-CH₃O—C₆H₄ | CH₃ | 4-Cl—C₆H₄ | 82~83 | 7.49~6.87(m, 8H), 4.48(E) 4.30(Z) (s, 2H), 3.85(s, 3H) 3.42(s, 3H) | 417(20), 178(100), 147(88), 121(58) |
| 29 | 4-CH₃O—C₆H₄ | CH₃ | 3,5-Cl—C₆H₃ | L | 7.71~6.98(m, 7H), 4.49(E) 4.31(Z) (s, 2H), 3.85(s, 3H) 3.32(s, 3H) | 451(35), 178(100), 147(82), 121(70) |
| 30 | 4-F—C₆H₄ | CH₃ | C₆H₅ | L | 7.54~7.03(m, 9H), 4.49(E) 4.31(Z) (s, 2H), 3.53(s, 3H) | 371(41), 166(100), 138(84), 109(78) |
| 31 | 4-F—C₆H₄ | CH₃ | 3-CH₃—C₆H₄ | L | 7.32~7.02(m, 8H), 4.49(E) 4.30(Z) (s, 2H), 3.30(s, 3H) 2.35(s, 3H) | 385(43), 166(100), 138(82), 109(79), 95(30) |
| 32 | 4-F—C₆H₄ | CH₃ | 4-CH₃—C₆H₄ | L | 7.36~7.00(m, 8H), 4.49(E) 4.31(Z) (s, 2H), 3.32(s, 3H) 2.33(s, 3H) | 385(21), 166(100), 138(94), 109(80) |
| 33 | 4-F—C₆H₄ | CH₃ | 3,5-(CH₃)₂—C₆H₃ | L | 7.30~6.93(m, 7H), 4.49(E) 4.30(Z) (s, 2H), 3.31(s, 3H) 2.32(s, 6H) | 399(50), 166(100), 138(76), 109(69) |
| 34 | 4-F—C₆H₄ | CH₃ | 3-CH₃O—C₆H₄ | L | 7.31~6.83(m, 8H), 4.48(E) 4.30(Z) (s, 2H), 3.86(s, 3H) 3.32(s, 3H) | 401(57), 166(100), 138(67), 109(45) |
| 35 | 4-F—C₆H₄ | CH₃ | 4-CH₃O—C₆H₄ | L | 7.35~6.78(m, 8H), 4.49(E) 4.30(Z) (s, 2H), 3.84(s, 3H) 3.33(s, 3H) | 401(42), 166(100), 138(52), 109(44) |
| 36 | 4-F—C₆H₄ | CH₃ | 3-F—C₆H₄ | L | 7.39~6.94(m, 8H), 4.48(E) 4.31(Z) (s, 2H), 3.31(s, 3H) | 389(41), 166(89), 138(100), 109(80), 95(30) |
| 37 | 4-F—C₆H₄ | CH₃ | 4-F—C₆H₄ | L | 7.46~6.94(m, 8H), 4.49(E) 4.31(Z) (s, 2H), 3.32(s, 3H) | 389(56), 166(100), 138(91), 109(76), 95(29) |
| 38 | 4-F—C₆H₄ | CH₃ | 3-Cl—C₆H₄ | L | 7.48~6.95(m, 8H), 4.49(E) 4.32(Z) (s, 2H), 3.33(s, 3H) | 405(26), 166(60), 138(42), 109(39), 43(100) |
| 39 | 4-F—C₆H₄ | CH₃ | 4-Cl—C₆H₄ | L | 7.45~7.05(m, 8H), 4.48(E) 4.30(Z) (s, 2H), 3.32(s, 3H) | 405(41), 166(100), 138(84), 109(73), 95(35) |
| 40 | 4-F—C₆H₄ | CH₃ | 3,5-Cl₂—C₆H₃ | L | 7.34~7.08(m, 7H), 4.49(E) 4.31(Z) (s, 2H), 3.30(s, 3H) | 439(46), 166(100), 138(89) |

TABLE 4-continued

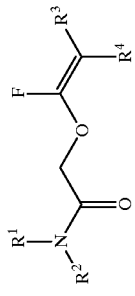

R⁴ = CF₃ (I)

| Comp. No. | R¹ | R² | R³ | state (° C.) | NMR (CDCl₃, TMS) δ (ppm) | MS (m/e) |
|---|---|---|---|---|---|---|
| 41 | 4-Cl—C₆H₄ | CH₃ | 3,5-Cl₂—C₆H₃ | 136–137 | 7.50~7.05(m, 7H), 4.48(E) 4.30(Z) (s, 2H), 3.31(s, 3H) | 109(90), 95(38) 455(31), 182(56), 147(100), 118(35), 77(24) |
| 42 | 2,4-F₂—C₆H₃ | CH₃ | 3-Cl—C₆H₄ | L | 7.45~6.85(m, 7H), 4.49(E) 4.31(Z) (s, 2H), 3.32(s, 3H) | 423(21), 184(34), 156(24), 127(100) |
| 43 | 2,4-Cl₂—C₆H₃ | CH₃ | 4-F—C₆H₄ | L | 7.79~6.87(m, 7H), 4.48(E) 4.31(Z) (s, 2H), 3.33(s, 3H) | 439(34), 216(57), 181(100), 145(50) |
| 44 | C₆H₅ | C₂H₅ | C₆H₅ | L | 7.65~7.09(m, 10H), 4.41(E) 4.28(Z) (s, 2H), 3.75(q, 2H), 1.13(t, 3H) | 367(12), 162(100), 134(79), 106(57), 91(55) |
| 45 | C₆H₅ | C₂H₅ | 3-CH₃—C₆H₄ | L | 7.49~7.01(m, 9H), 4.42(E) 4.29(Z) (s, 2H), 3.76(q, 2H), 2.39(s, 3H), 1.14(t, 3H) | 381(100), 363(10), 162(56), 134(64) |
| 46 | C₆H₅ | C₂H₅ | 3-CH₃O—C₆H₄ | L | 7.62~6.81(m, 9H), 4.43(E) 4.28(Z) (s, 2H), 3.85(s, 3H), 3.74(q, 2H), 1.14(t, 3H) | 397(29), 378(16), 162(99), 134(100), 106(78) |
| 47 | C₆H₅ | C₂H₅ | 4-C₂H₅O—C₆H₄ | L | 7.42~6.75(m, 9H), 4.28(E) 4.28(Z) (s, 2H), 3.94(q, 2H), 3.72(q, 2H), 1.34(t, 3H), 1.13(t, 3H) | 411(25), 221(54), 162(100), 134(72) |
| 48 | C₆H₅ | C₂H₅ | 3-CF₃—C₆H₄ | L | 7.82~7.02(m, 9H), 4.42(E) 4.29(Z) (s, 2H), 3.74(q, 2H), 1.13(t, 3H) | 435(16), 162(100), 134(89), 106(46) |
| 49 | C₆H₅ | C₂H₅ | 3-F—C₆H₄ | L | 7.49~6.90(m, 9H), 4.28(E) 4.29(Z) (s, 2H), 3.75(q, 2H), 1.13(t, 3H) | 385(30), 162(100), 134(71), 106(43) |
| 50 | C₆H₅ | C₂H₅ | 4-F—C₆H₄ | L | 7.62~6.92(m, 9H), 4.41(E) 4.29(Z) (s, 2H), 3.76(q, 2H), 1.14(t, 3H) | 385(39), 162(100), 133(80), 91(53) |
| 51 | C₆H₅ | C₂H₅ | 4-Cl—C₆H₄ | L | 7.57~6.98(m, 9H), 4.42(E) 4.29(Z) (s, 2H), 3.76(q, 2H), 1.14(t, 3H) | 401(40), 162(100), 134(56) |
| 52 | C₆H₅ | C₂H₅ | C₄H₃S-2-yl | L | 7.68~6.93(m, 8H), 4.42(E) 4.29(Z) (s, 2H), 3.75(q, 2H), 1.16(t, 3H) | 373(31), 162(100), 134(32) |
| 53 | 4-CH₃—C₆H₄ | C₂H₅ | C₆H₅ | L | 7.49~6.94(m, 9H), 4.43(E) 4.29(Z) (s, 2H), 3.74(q, 2H), 2.39(s, 3H), 1.13(t, 3H) | 381(55), 176(100, 105(44) |
| 54 | 4-CH₃—C₆H₄ | C₂H₅ | 4-F—C₆H₄ | L | 7.63~6.89(m, 8H), 4.42(E) 4.29(Z) (s, 2H), 3.74(q, 2H), 2.38(s, 3H), 1.12(t, 3H) | 399(55), 176(100), 148(55) |
| 55 | 4-CH₃O—C₆H₄ | C₂H₅ | C₆H₅ | L | 7.49~6.85(m, 9H), 4.41(E) 4.27(Z) (s, 2H), 3.81(s, 3H), 3.72(q, 2H), 1.13(t, 3H) | 397(23), 378(12), 193(100), 165(36) |
| 56 | 4-CH₃O—C₆H₄ | C₂H₅ | 4-F—C₆H₄ | L | 7.48~6.84(m, 8H), 4.42(E) 4.28(Z) (s, 2H), 3.82(s, 3H), 3.75(q, 2H), 1.12(t, 3H) | 415(14), 192(100), 164(43), 121(75) |
| 57 | 3-CF₃—C₆H₄ | C₂H₅ | C₆H₅ | 52~53 | 7.81~7.23(m, 9H), 4.43(E) 4.29(Z) (s, 2H), 3.72(q, 2H), 1.13(t, 3H) | 435(26), 221(100), 174(61), 159(69) |
| 58 | 3-CF₃—C₆H₄ | C₂H₅ | 4-CH₃—C₆H₄ | 48~49 | 7.86~7.02(m, 8H), 4.41(E) 4.28(Z) (s, 2H), 3.72(q, 2H), 2.38(s, 3H), 1.12(t, 3H) | 449(10), 230(100), 202(36), 174(27) |
| 59 | 3-CF₃—C₆H₄ | C₂H₅ | 4-F—C₆H₄ | L | 7.89~6.85(m, 8H), 4.41(E) 4.29(Z) (s, 2H), 3.73(q, 2H), 1.14(t, 3H) | 453(26), 231(100), 201(63) |
| 60 | 2-Cl—C₆H₄ | C₂H₅ | C₆H₅ | L | 7.60~7.12(m, 9H), 4.40(E) 4.28(Z) (s, 2H), 4.02(m, 1H), | 401(72), 382(15), 196(100), |

TABLE 4-continued $$R^4 = CF_3 \quad (I)$$

Structure:
$$R^1\text{-}N(R^2)\text{-}C(=O)\text{-}CH_2\text{-}O\text{-}C(F)=C(R^3)(R^4)$$

| Comp. No. | R¹ | R² | R³ | state (° C.) | NMR (CDCl₃, TMS) δ (ppm) | MS (m/e) |
|---|---|---|---|---|---|---|
| 61 | 2-Cl—C₆H₄ | C₂H₅ | 4-CH₃—C₆H₄ | L | 3.48(m, 1H), 1.12(t, 3H) 7.62~7.02(m, 8H), 4.28(E) 4.40(E) (s, 2H), 4.06(m, 1H), 3.49(m, 1H), 2.39(s, 3H), 1.14(t, 3H) | 168(44), 146(35) 415(26), 196(100), 118(35) |
| 62 | 3-Cl—C₆H₄ | C₂H₅ | C₆H₅ | L | 7.49~6.94(m, 9H), 4.41(E) 4.28(Z) (s, 2H), 3.73(q, 2H), 1.13(t, 3H) | 401(14), 196(100), 168(24), 146(27) |
| 63 | 4-Cl—C₆H₄ | C₂H₅ | C₆H₅ | L | 7.50~6.90(m, 9H), 4.40(E) 4.28(Z) (s, 2H), 3.74(q, 2H), 1.14(t, 3H) | 401(10), 196(100), 146(37), 118(18) |
| 64 | 4-Cl—C₆H₄ | C₂H₅ | 4-CH₃—C₆H₄ | 70~71 | 7.62~6.95(m, 8H), 4.40(E) 4.29(Z) (s, 2H), 3.76(q, 2H), 2.39(s, 3H), 1.14(t, 3H) | 415(12), 196(81), 161(100), 118(27) |
| 65 | C₆H₅ | n-C₃H₇ | 4-CH₃—C₆H₄ | L | 7.50~7.02(m, 10H), 4.40(E) 4.25(Z) (s, 2H), 3.65(t, 2H), 1.68~1.41(m, 2H), 0.91(t, 3H) | 381(11), 176(100), 134(84), 106(93), 77(62) |
| 66 | C₆H₅ | n-C₃H₇ | C₆H₅ | L | 7.62~6.97(m, 9H), 4.40(E) 4.26(Z) (s, 2H), 3.64(t, 2H), 2.32(s, 3H), 1.67~1.42(m, 2H), 0.91(t, 3H) | 395(20), 377(13), 176(100) |
| 67 | 4-CH₃O—C₆H₄ | n-C₃H₇ | 4-CH₃—C₆H₄ | L | 7.53~6.86(m, 9H), 4.40(E) 4.25(Z) (s, 2H), 3.81(s, 3H), 3.65(t, 2H), 1.65~1.41(m, 2H), 0.91(t, 3H) | 411(24), 206(100), 178(35), 164(48), 136(42) |
| 68 | 4-CH₃O—C₆H₄ | n-C₃H₇ | C₆H₅ | L | 7.62~6.79(m, 8H), 4.39(E) 4.25(Z) (s, 2H), 3.83(s, 3H), 3.65(t, 2H), 2.32(s, 3H), 1.68~1.42(m, 2H), 0.92(t, 3H) | 425(29), 406(14), 203(100) |
| 69 | C₆H₅ | i-C₃H₇ | C₆H₅ | 54~55 | 7.50~7.01(m, 10H), 5.09~4.87(m, 1H), 4.30(E) 4.14(Z) (s, 2H), 1.08(d, 6H) | 381(12), 176(59), 134(100), 106(97), 77(89) |
| 70 | C₆H₅ | i-C₃H₇ | 3-CH₃—C₆H₄ | L | 7.62~6.82(m, 9H), 5.10~4.89(m, 1H), 4.29(E) 4.16(Z) (s, 2H), 2.39(s, 3H), 1.09(d, 6H) | 395(39), 176(34), 134(100), 106(69) |
| 71 | C₆H₅ | i-C₃H₇ | 4-CH₃—C₆H₄ | 67~68 | 7.62~6.97(m, 9H), 5.28~4.86(m, 1H), 4.29(E) 4.15(Z) (s, 2H), 2.46(s, 3H), 1.09(d, 6H) | 395(65), 376(49), 176(100), 106(76) |
| 72 | C₆H₅ | i-C₃H₇ | 3,5-(CH₃)₂—C₆H₃ | L | 7.64~6.85(m, 8H), 5.28~4.88(m, 1H), 4.30(E) 4.16(Z) (s, 2H), 2.38(s, 6H), 1.09(d, 6H) | 409(56), 134(100), 106(87), 77(52) |
| 73 | C₆H₅ | i-C₃H₇ | 3-CH₃O—C₆H₄ | L | 7.51~6.79(m, 9H), 5.19~4.84(m, 1H), 4.28(E) 4.14(Z) (s, 2H), 3.80(s, 3H), 1.08(d, 6H) | 411(30), 176(39), 134(100), 106(50) |
| 74 | C₆H₅ | i-C₃H₇ | 4-CH₃O—C₆H₄ | 48~49 | 7.71~6.95(m, 9H), 5.21~4.85(m, 1H), 4.29(E) 4.15(Z) (s, 2H), 3.81(s, 3H), 1.09(d, 6H) | 411(33), 176(57), 134(100), 106(74) |
| 75 | C₆H₅ | i-C₃H₇ | 4-C₂H₅O—C₆H₄ | L | 7.48~6.79(m, 9H), 5.10~4.84(m, 1H), 4.28(E) 4.16(Z) (s, 2H), 4.40(q, 2H), 1.38(t, 3H), 1.09(d, 6H) | 425(70), 176(63), 134(100), 106(69), 84(55) |
| 76 | C₆H₅ | i-C₃H₇ | 3,4-OCH₂O—C₆H₃ | L | 7.59~6.75(m, 8H), 5.96(s, 2H), 5.11~4.86(m, 1H), 4.29(E) 4.16(Z) (s, 2H), 1.08(d, 6H) | 425(15), 219(30), 134(100), 106(60) |
| 77 | C₆H₅ | i-C₃H₇ | 3-F—C₆H₄ | L | 7.50~6.91(m, 9H), 5.10~4.82(m, 1H), 4.28(E) 4.15(Z) (s, 2H), 1.08(d, 6H) | 399(40), 134(100), 106(70) |
| 78 | C₆H₅ | i-C₃H₇ | 4-F—C₆H₄ | L | 7.54~6.89(m, 9H), 5.09~4.84(m, 1H), 4.29(E) 4.15(Z) (s, 2H), 1.08(d, 6H) | 399(35), 176(45), 134(100), 106(83) |
| 79 | C₆H₅ | i-C₃H₇ | 3-Cl—C₆H₄ | L | 7.69~6.94(m, 9H), 5.11~4.88(m, 1H), 4.29(E) 4.15(Z) (s, 2H), 1.08(d, 6H) | 415(45), 176(31), 134(100), 106(65) |
| 80 | C₆H₅ | i-C₃H₇ | 4-Cl—C₆H₄ | 72~73 | 7.87~6.87(m, 9H), 5.21~4.87(m, 1H), 4.28(E) 4.14(Z) (s, 2H), 1.08(d, 6H) | 415(25), 176(28), 134(100) |

TABLE 4-continued $$R^4 = CF_3 \quad (I)$$

[Structure: R¹R²N-C(=O)-CH₂-O-C(F)=C(R³)(R⁴)]

| Comp. No. | R¹ | R² | R³ | state (° C.) | NMR (CDCl₃, TMS) δ (ppm) | MS (m/e) |
|---|---|---|---|---|---|---|
| 81 | C₆H₅ | i-C₃H₇ | C₄H₃S-2-yl | 63–64 | (s, 2H), 1.09(d, 6H) | 106(73), 78(34) |
| 82 | 2-CH₃—C₆H₄ | i-C₃H₇ | C₆H₅ | L | 7.50–6.94(m, 8H), 5.18–4.81(m, 1H), 4.29(E) 4.16(Z) (s, 2H), 1.08(d, 6H) | 387(22), 176(31), 134(100), 106(85), 77(41), 43(46) |
| 83 | 2-CH₃—C₆H₄ | i-C₃H₇ | 4-CH₃—C₆H₄ | L | 7.61–6.97(m, 9H), 5.00–4.78(m, 1H), 4.28(E) 4.17(Z) (dd, 2H), 2.32(s, 3H), 1.27(d, 3H), 1.02(d, 3H) | 395(46), 148(100), 120(47), 45(23) |
| 84 | 2-CH₃—C₆H₄ | i-C₃H₇ | 3,4-(CH₃)₂—C₆H₃ | L | 7.48–6.95(m, 8H), 4.95–4.75(m, 1H), 4.29(E) 4.15(Z) (dd, 2H), 2.33(s, 3H), 2.31(s, 3H), 1.30(d, 3H), 1.00(d, 3H) | 409(9), 190(34), 148(100), 120(80), 118(30), 91(30), 45(42) |
| 85 | 2-CH₃—C₆H₄ | i-C₃H₇ | 3,5-(CH₃)₂—C₆H₃ | L | 7.42–7.00(m, 7H), 4.96–4.76(m, 1H), 4.28(E) 4.15(Z) (dd, 2H), 2.33(s, 3H), 2.30(s, 6H), 1.30(d, 3H), 1.02(d, 3H) | 423(15), 148(100), 120(49), 45(22) |
| 86 | 2-CH₃—C₆H₄ | i-C₃H₇ | 3-CH₃O—C₆H₄ | L | 7.40–6.85(m, 7H), 4.95–4.76(m, 1H), 4.28(E) 4.16(Z) (dd, 2H), 2.33(s, 3H), 2.31(s, 6H), 1.31(d, 3H), 1.01(d, 3H) | 423(20), 148(100), 120(45), 45(24) |
| 87 | 2-CH₃—C₆H₄ | i-C₃H₇ | 4-CH₃O—C₆H₄ | L | 7.46–6.75(m, 8H), 4.90–4.72(m, 1H), 4.28(E) 4.16(Z) (dd, 2H), 3.82(s, 3H), 2.32(s, 3H), 1.28(d, 3H), 0.98(d, 3H) | 425(R), 148(100), 120(82), 45(39) |
| 88 | 2-CH₃—C₆H₄ | i-C₃H₇ | 3-F—C₆H₄ | L | 7.40–6.80(m, 8H), 4.91–4.75(m, 1H), 4.28(E) 4.15(Z) (dd, 2H), 3.81(s, 3H), 2.31(s, 3H), 1.29(d, 3H), 0.99(d, 3H) | 425(8), 148(100), 120(63), 45(25) |
| 89 | 2-CH₃—C₆H₄ | i-C₃H₇ | 4-F—C₆H₄ | L | 7.38–6.87(m, 8H), 4.91–4.72(m, 1H), 4.28(E) 4.16(Z) (dd, 2H), 2.31(s, 3H), 1.29(d, 3H), 0.98(d, 3H) | 413(54), 148(100), 120(68), 45(39) |
| 90 | 2-CH₃—C₆H₄ | i-C₃H₇ | 3-Cl—C₆H₄ | L | 7.51–6.95(m, 8H), 4.97–4.78(m, 1H), 4.28(E) 4.15(Z) (dd, 2H), 2.30(s, 3H), 1.25(d, 3H), 1.01(d, 3H) | 413(22), 190(89), 148(100), 120(94), 91(73) |
| 91 | 2-CH₃—C₆H₄ | i-C₃H₇ | 4-Cl—C₆H₄ | L | 7.54–7.00(m, 8H), 4.96–4.74(m, 1H), 4.27(E) 4.16(Z) (dd, 2H), 2.28(s, 3H), 1.30(d, 3H), 1.01(d, 3H) | 429(16), 148(100), 120(51), 45(23) |
| 92 | 2-CH₃—C₆H₄ | i-C₃H₇ | 3,5-Cl₂—C₆H₃ | L | 7.50–7.00(m, 8H), 4.95–4.76(m, 1H), 4.28(E) 4.15(Z) (dd, 2H), 2.29(s, 3H), 1.28(d, 3H), 1.00(d, 3H) | 429(30), 148(100), 120(52), 84(32), 45(36) |
| 93 | 3-CH₃—C₆H₄ | i-C₃H₇ | C₆H₅ | 64–65 | 7.52–7.00(m, 7H), 4.95–4.75(m, 1H), 4.27(E) 4.15(Z) (dd, 2H), 2.28(s, 3H), 1.30(d, 3H), 1.01(d, 3H) | 463(16), 148(100), 120(73), 45(45) |
| 94 | 3-CH₃—C₆H₄ | i-C₃H₇ | 3-CH₃—C₆H₄ | L | 7.45–6.80(m, 9H), 5.02–4.79(m, 1H), 4.30(E) 4.12(Z) (s, 2H), 2.35(s, 3H), 1.08(d, 6H) | 395(14), 190(56), 148(100), 120(95), 91(35) |
| 95 | 3-CH₃—C₆H₄ | i-C₃H₇ | 4-C₂H₅—C₆H₄ | 76–77 | 7.32–6.79(m, 8H), 5.03–4.80(m, 1H), 4.30(E) 4.15(Z) (s, 2H), 2.34(s, 3H), 2.30(s, 3H), 1.09(d, 6H) | 409(11), 190(28), 148(100), 120(51), 84(39) |
| 96 | 3-CH₃—C₆H₄ | i-C₃H₇ | 4-C₂H₅—C₆H₄ | 66–67 | 7.32–6.80(m, 8H), 5.04–4.83(m, 1H), 4.28(E) 4.14(Z) (s, 2H), 2.38(s, 3H), 2.31(s, 3H), 1.05(d, 6H) | 409(36), 190(60), 148(100), 120(54) |
| 97 | 3-CH₃—C₆H₄ | i-C₃H₇ | 3,4-(CH₃)₂—C₆H₃ | L | 7.40–6.81(m, 8H), 5.04–4.84(m, 1H), 4.30(E) 4.16(Z) (s, 2H), 2.38(s, 3H), 1.26(d, 3H), 1.09(d, 6H) | 423(41), 190(47), 148(100), 120(60), 91(21) |
| | | | | | 7.48–6.81(m, 7H), 5.03–4.85(m, 1H), 4.31(E) 4.17(Z) | 423(56), 190(39), 148(100), |

TABLE 4-continued

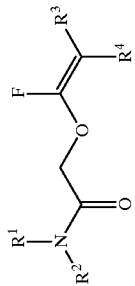

R⁴ = CF₃

| Comp. No. | R¹ | R² | R₃ | state (° C.) | NMR (CDCl₃, TMS) δ (ppm) | MS (m/e) |
|---|---|---|---|---|---|---|
| 98 | 3-CH₃—C₆H₄ | i-C₃H₇ | 3,5-(CH₃)₂—C₆H₃ | 60–61 | (s, 2H), 2.39(s, 3H), 2.25(s, 6H), 1.08(d, 6H) 7.38–6.80(m, 7H), 5.05–4.85(m, 1H), 4.29(E) 4.15(Z) | 120(52), 91(20) 423(57), 190(69), 148(100), |
| 99 | 3-CH₃—C₆H₄ | i-C₃H₇ | 3-CH₃—C₆H₄ | 46–47 | (s, 2H), 2.35(s, 3H), 2.29(s, 6H), 1.07(d, 6H) 7.41–6.82(m, 8H), 5.06–4.86(m, 1H), 4.30(E) 4.16(Z) | 120(63), 91(24) 425(58), 190(37), 148(100), |
| 100 | 3-CH₃—C₆H₄ | i-C₃H₇ | 4-CH₃O—C₆H₄ | 68–69 | (s, 2H), 3.80(s, 3H), 2.35(s, 3H), 1.10(d, 6H) 7.37–6.79(m, 8H), 5.01–4.80(m, 1H), 4.30(E) 4.15(Z) | 120(53) 425(31), 190(11), 148(100), |
| 101 | 3-CH₃—C₆H₄ | i-C₃H₇ | 3-F—C₆H₄ | 42–43 | (s, 2H), 3.82(s, 3H), 2.34(s, 3H), 1.07(d, 6H) 7.35–6.81(m, 8H), 5.01–4.78(m, 1H), 4.30(E) 4.14(Z) | 1.20(79), 91(30) 413(57), 190(37), 148(100), |
| 102 | 3-CH₃—C₆H₄ | i-C₃H₇ | 4-F—C₆H₄ | L | (s, 2H), 2.35(s, 3H), 1.09(d, 6H) 7.50–6.85(m, 8H), 5.04–4.85(m, 1H), 4.29(E) 4.16(Z) | 120(54) 413(51), 148(100), 120(90) |
| 103 | 3-CH₃—C₆H₄ | i-C₃H₇ | 3-Cl—C₆H₄ | L | (s, 2H), 2.39(s, 3H), 1.09(d, 6H) 7.48–6.78(m, 8H), 5.02–4.85(m, 1H), 4.30(E) 4.14(Z) | 429(25), 148(100), 120(83) |
| 104 | 3-CH₃—C₆H₄ | i-C₃H₇ | 4-Cl—C₆H₄ | 56–57 | (s, 2H), 2.38(s, 3H), 1.08(d, 6H) 7.40–6.62(m, 8H), 5.02–4.85(m, 1H), 4.30(E) 4.15(Z) | 429(55), 190(23), 148(100), |
| 105 | 3-CH₃—C₆H₄ | i-C₃H₇ | 3,5-Cl₂—C₆H₃ | 58–59 | (s, 2H), 2.35(s, 3H), 1.08(d, 6H) 7.35–6.80(m, 7H), 5.00–4.80(m, 1H), 4.31(E) 4.17(Z) | 120(53) 463(51), 148(100), 120(37) |
| 106 | 3-CH₃—C₆H₄ | i-C₃H₇ | C₆H₅ | 80–81 | (s, 2H), 2.35(s, 3H), 1.07(d, 6H) 7.50–6.58(m, 9H), 5.08–4.85(m, 1H), 4.29(E) 4.14(Z) | 411(28), 208(100), 165(82), |
| 107 | 3-CH₃—C₆H₄ | i-C₃H₇ | 4-CH₃—C₆H₄ | 93–94 | (s, 2H), 3.82(s, 3H), 1.09(d, 6H) 7.52–6.53(m, 8H), 5.23–4.78(m, 1H), 4.30(E) 4.15(Z) | 137(36) 425(33), 375(100), 118(78) |
| 108 | 3-CH₃—C₆H₄ | i-C₃H₇ | 4-F—C₆H₄ | 50–51 | (s, 2H), 3.82(s, 3H), 2.41(s, 3H), 1.12(d, 6H) 7.45–6.55(m, 8H), 5.02–4.85(m, 1H), 4.31(E) 4.16(Z) | 429(52), 206(82), 164(100), |
| 109 | 3,4-CH₃O—C₆H₄ | i-C₃H₇ | 3-Cl—C₆H₄ | L | (s, 2H), 3.80(s, 3H), 1.09(d, 6H) 7.51–6.76(m, 8H), 5.02–4.82(m, 1H), 4.30(E) 4.14(Z) | 136(86), 45(24) 445(50), 206(50), 164(100), |
| 110 | 3-CH₃O—C₆H₄ | i-C₃H₇ | 4-Cl—C₆H₄ | 60–61 | (s, 2H), 3.82(s, 3H), 1.02(d, 6H) 7.45–6.58(m, 8H), 5.02–4.85(m, 1H), 4.29(E) 4.14(Z) | 136(68), 45(54) 445(24), 206(66), 164(100), |
| 111 | 3-CH₃O—C₆H₄ | i-C₃H₇ | 3,5-Cl₂—C₆H₃ | L | (s, 2H), 3.81(s, 3H), 1.10(d, 6H) 7.41–6.61(m, 7H), 5.00–4.84(m, 1H), 4.30(E) 4.15(Z) | 136(92), 45(37) 479(51), 206(54), 164(100), |
| 112 | 3-CH₃O—C₆H₄ | i-C₃H₇ | C₆H₅ | L | (s, 2H), 3.81(s, 3H), 1.09(d, 6H) 7.49–6.81(m, 9H), 5.04–4.82(m, 1H), 4.29(E) 4.13(Z) | 137(74), 45(26) 411(56), 206(68), 164(100), |
| 113 | 3-CH₃O—C₆H₄ | i-C₃H₇ | 3-CH₃—C₆H₄ | L | (s, 2H), 3.81(s, 3H), 1.04(d, 6H) 7.55–6.88(m, 8H), 5.12–4.79(m, 1H), 4.31(E) 4.16(Z) | 136(52), 121(74) 425(26), 210(81), 168(100), |
| 114 | 3,4-CH₃O—C₆H₄ | i-C₃H₇ | 4-CH₃—C₆H₄ | 87–88 | (s, 2H), 3.81(s, 3H), 2.38(s, 3H), 1.08(d, 6H) 7.62–6.98(m, 8H), 5.21–4.82(m, 1H), 4.29(E) 4.14(Z) | 140(53), 133(49), 45(51) 425(14), 406(10), 203(100), |
| 115 | 4-CH₃O—C₆H₄ | i-C₃H₇ | 4-CH₃O—C₆H₄ | L | (s, 2H), 3.82(s, 3H), 2.35(s, 3H), 1.08(d, 6H) 7.40–6.81(m, 8H), 5.02–4.83(m, 1H), 4.29(E) 4.15(Z) | 69(27) 441(30), 206(76), 164(100), |
| 116 | 4-CH₃O—C₆H₄ | i-C₃H₄ | 4-F—C₆H₄ | L | (s, 2H), 3.81(s, 3H), 3.79(s, 3H), 1.08(d, 6H) 7.49–6.86(m, 8H), 5.03–4.84(m, 1H), 4.30(E) 4.15(Z) | 136(42), 121(47) 429(57), 206(36), 164(100), |
| 117 | 4-CH₃O—C₆H₄ | i-C₃H₇ | 3-Cl—C₆H₄ | L | (s, 2H), 3.82(s, 3H), 1.10(d, 6H) 7.49–6.88(m, 8H), 5.03–4.85(m, 1H), 4.29(E) 4.17(Z) | 136(52) 445(62), 164(100), 121(42) |

TABLE 4-continued $$R^4 = CF_3 \quad (I)$$

(Structure: R¹R²N-C(=O)-CH₂-O-C(F)=C(R³)(R⁴))

| Comp. No. | R¹ | R² | R³ | state (°C.) | NMR (CDCl₃, TMS) δ (ppm) | MS (m/e) |
|---|---|---|---|---|---|---|
| 118 | 3-CF₃—C₆H₄ | i-C₃H₇ | C₆H₅ | L | (s, 2H), 3.82(s, 3H), 1.10(d, 6H) 7.80~7.23(m, 9H), 5.12–4.89(m, 1H), 4.30(E) 4.15(Z) (s, 2H), 1.02(d, 6H) | 449(36), 430(19), 244(100), 174(40) |
| 119 | 3-CF₃—C₆H₄ | i-C₃H₇ | 3,4-OCH₂O—C₆H₃ | L | 7.95–6.72(m, 7H), 5.95(s, 2H), 5.28–4.84(m, 1H), 4.29(E) 4.14(Z) (s, 2H), 1.09(d, 6H) | 493(35), 244(21), 202(100) |
| 120 | 3-CF₃—C₆H₄ | i-C₃H₇ | 4-F—C₆H₄ | L | 7.81–6.98(m, 8H), 5.05–4.92(m, 1H), 4.29(E) 4.16(Z) (s, 2H), 1.12(d, 6H) | 467(30), 244(35), 203(100), 174(78), 145(65) |
| 121 | 3-CF₃—C₆H₄ | i-C₃H₇ | 3-Cl—C₆H₄ | L | 7.79–7.18(m, 8H), 5.09–4.89(m, 1H), 4.30(E) 4.14(Z) (s, 2H), 1.10(d, 6H) | 483(24), 202(100), 174(31) |
| 122 | 4-F—C₆H₄ | i-C₃H₇ | C₆H₅ | 75~76 | 7.51–6.91(m, 9H), 5.15–4.67(m, 1H), 4.29(E) 4.14(Z) (s, 2H), 1.02(d, 6H) | 399(70), 380(26), 194(100), 152(94), 123(91), 109(36) |
| 123 | 4-F—C₆H₄ | i-C₃H₇ | 4-CH₃—C₆H₄ | 68~69 | 7.46–6.98(m, 8H), 5.21–4.78(m, 1H), 4.30(E) 4.15(Z) (s, 2H), 2.46(s, 3H), 1.07(d, 6H) | 413(45), 394(100), 109(36) |
| 124 | 4-F—C₆H₄ | i-C₃H₇ | 3-CH₃O—C₆H₄ | L | 7.51–6.91(m, 8H), 5.51–4.67(m, 1H), 4.29(E) 4.17(Z) (s, 2H), 3.85(s, 3H), 1.02(d, 6H) | 429(22), 410(15), 194(47), 152(100), 124(41) |
| 125 | 4-F—C₆H₄ | i-C₃H₇ | 3-CF₃—C₆H₄ | L | 7.79–7.05(m, 1H), 5.23–4.82(m, 1H), 4.30(E) 4.14(Z) (s, 2H), 1.08(d, 6H) | 467(15), 194(51), 152(100), 124(36) |
| 126 | 4-F—C₆H₄ | i-C₃H₇ | 4-F—C₆H₄ | L | 7.49–6.98(m, 8H), 5.06–4.87(m, 1H), 4.29(E) 4.16(Z) (m, 2H), 1.11(d, 6H) | 417(36), 194(92), 152(100), 122(86) |
| 127 | 4-F—C₆H₄ | i-C₃H₇ | 3-Cl—C₆H₄ | L | 7.41–7.01(m, 8H), 5.02–4.85(m, 1H), 4.30(E) 4.14(Z) (m, 2H), 1.02(d, 6H) | 433(45), 152(100), 124(41) |
| 128 | 4-F—C₆H₄ | i-C₃H₇ | C₄H₃S-2-yl | L | 7.46–6.97(m, 7H), 5.21–4.75(m, 1H), 4.29(E) 4.15(Z) (s, 2H), 1.09(d, 6H) | 405(31), 194(36), 152(100), 122(21), 109(24) |
| 129 | 2-Cl—C₆H₄ | i-C₃H₇ | C₆H₅ | L | 7.58–7.02(m, 9H), 4.98–4.79(m, 1H), 4.29(E) 4.15(Z) (dd, 2H), 1.24(d, 3H), 1.02(d, 3H) | 415(25), 168(100), 140(64), 45(57) |
| 130 | 2-Cl—C₆H₄ | i-C₃H₇ | 3-CH₃—C₆H₄ | L | 7.61~7.02(m, 8H), 5.03–4.79(m, 1H), 4.31(E) 4.14(Z) (dd, 2H), 2.35(s, 3H), 1.24(d, 3H), 1.02(d, 3H) | 429(60), 168(100), 140(53) |
| 131 | 2-Cl—C₆H₄ | i-C₃H₇ | 4-CH₃—C₆H₄ | L | 7.61~7.08(m, 8H), 4.98–4.79(m, 1H), 4.30(E) 4.15(Z) (dd, 2H), 2.35(s, 3H), 1.25(d, 3H), 1.02(d, 3H) | 429(15), 168(100), 140(44) |
| 132 | 2-Cl—C₆H₄ | i-C₃H₇ | 4-C₂H₅—C₆H₄ | L | 7.60~7.08(m, 8H), 4.98–4.78(m, 1H), 4.33(E) 4.14(Z) (dd, 2H), 2.65(q, 2H), 1.32(t, 3H), 1.25(d, 3H), 1.03(d, 3H) | 443(17), 210(59), 168(100), 1.33(86), 45(78) |
| 133 | 2-Cl—C₆H₄ | i-C₃H₇ | 3,4-(CH₃)₂—C₆H₃ | L | 7.59~7.02(m, 7H), 4.98–4.79(m, 1H), 4.29(E) 4.16(Z) (dd, 2H), 2.26(s, 6H), 1.23(d, 3H), 1.02(d, 3H) | 443(20), 170(59), 168(100), 140(59) |
| 134 | 2-Cl—C₆H₄ | i-C₃H₇ | 3,5-(CH₃)₂—C₆H₃ | 64~65 | 7.58–6.89(m, 7H), 5.02–4.78(m, 1H), 4.30(E) 4.15(Z) (dd, 2H), 2.28(s, 6H), 1.23(d, 3H), 1.00(d, 3H) | 443(30), 168(100), 140(44) |
| 135 | 2-Cl—C₆H₄ | i-C₃H₇ | 3-CH₃O—C₆H₄ | L | 7.60–6.80(m, 8H), 5.00–4.80(m, 1H), 4.29(E) 4.17(Z) (dd, 2H), 3.79(s, 3H), 1.27(d, 3H), 1.01(d, 3H) | 445(30), 210(25), 168(100), 140(68), 133(56), 45(36) |
| 136 | 2-Cl—C₆H₄ | i-C₃H₇ | 4-CH₃O—C₆H₄ | L | 7.59–6.87(m, 8H), 4.99–4.78(m, 1H), 4.32(E) 4.13(Z) (dd, 2H), 3.79(s, 3H), 1.25(d, 3H), 1.03(d, 3H) | 445(25), 168(100), 140(49), 45(78) |

TABLE 4-continued

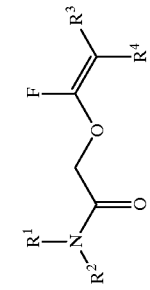

R⁴ = CF₃ (I)

| Comp. No. | R¹ | R² | R³ | state (° C.) | NMR (CDCl₃, TMS) δ (ppm) | MS (m/e) |
|---|---|---|---|---|---|---|
| 137 | 2-Cl—C₆H₄ | i-C₃H₇ | 3-F—C₆H₄ | L | 7.61~6.91(m, 8H), 5.01~4.78(m, 1H), 4.30(E) 4.18(Z) (dd, 2H), 1.28(d, 3H), 1.02(d, 3H) | 4.33(25), 210(57), 168(100), 140(81), 133(56) |
| 138 | 2-Cl—C₆H₄ | i-C₃H₇ | 4-F—C₆H₄ | L | 7.60~6.98(m, 8H), 5.02~4.79(m, 1H), 4.32(E) 4.19(Z) (dd, 2H), 1.29(d, 3H), 1.03(d, 3H) | 433(30), 168(100), 140(67), 133(47) |
| 139 | 2-Cl—C₆H₄ | i-C₃H₇ | 3-Cl—C₆H₄ | L | 7.59~7.04(m, 8H), 4.99~4.78(m, 1H), 4.33(E) 4.16(Z) (dd, 2H), 1.29(d, 3H), 1.02(d, 3H) | 449(20), 168(100), 140(64), 45(75) |
| 140 | 2-Cl—C₆H₄ | i-C₃H₇ | 4-Cl—C₆H₄ | L | 7.62~7.15(m, 8H), 5.00~4.75(m, 1H), 4.30(E) 4.17(Z) (dd, 2H), 1.25(d, 3H), 1.02(d, 3H) | 449(15), 168(100), 140(49), 133(37), 45(34) |
| 141 | 2-Cl—C₆H₄ | i-C₃H₇ | 3,5-Cl₂—C₆H₃ | L | 7.57~7.01(m, 7H), 4.97~4.79(m, 1H), 4.30(E) 4.22(Z) (dd, 2H), 1.29(d, 3H), 1.02(d, 3H) | 483(25), 168(100), 140(77), 133(63) |
| 142 | 2-Cl—C₆H₄ | i-C₃H₇ | C₆H₃ | L | 7.65~6.98(m, 9H), 5.09~4.84(m, 1H), 4.30(E) 4.15(Z) (s, 2H), 1.09(d, 6H) | 415(10), 211(45), 169(100), 87(35) |
| 143 | 3-Cl—C₆H₄ | i-C₃H₇ | 4-CH₃—C₆H₄ | 79~80 | 7.52~6.53(m, 8H), 5.24~4.72(m, 1H), 4.29(E) 4.17(Z) (s, 2H), 2.32(s, 3H), 1.21(d, 6H) | 429(15), 210(42), 168(100), 140(53), 133(41) |
| 144 | 3-Cl—C₆H₄ | i-C₃H₇ | 4-F—C₆H₄ | L | 7.51~6.90(m, 8H), 5.03~4.83(m, 1H), 4.30(E) 4.16(Z) (s, 2H), 1.08(d, 6H) | 433(45), 210(42), 168(100), 140(80), 133(52) |
| 145 | 3-Cl—C₆H₄ | i-C₃H₇ | 3-Cl—C₆H₄ | L | 7.69~6.95(m, 8H), 5.09~4.85(m, 1H), 4.31(E) 4.18(Z) (s, 2H), 1.10(d, 6H) | 449(35), 168(100), 140(60), 45(8H) |
| 146 | 2-Cl-4-F—C₆H₃ | i-C₃H₇ | C₆H₅ | L | 7.45~6.92(m, 1), 5.00~4.77(m, 1H), 4.32(E) 4.19(Z) (dd, 2H), 1.29(d, 3H), 1.03(d, 3H) | 433(56), 193(54), 168(65), 151(100), 45(46) |
| 147 | 2-Cl-4-F—C₆H₃ | i-C₃H₇ | 3-CH₃—C₆H₄ | L | 7.34~6.98(m, 7H), 5.00~4.77(m, 1H), 4.32(E) 4.17(Z) (dd, 2H), 2.32(s, 3H), 1.27(d, 3H), 1.04(d, 3H) | 447(35), 186(33), 84(100), 45(49) |
| 148 | 2-Cl-4-F—C₆H₃ | i-C₃H₇ | 4-CH₃—C₆H₄ | L | 7.41~6.99(m, 7H), 5.01~4.76(m, 1H), 4.30(E) 4.16(Z) (dd, 2H), 2.33(s, 3H), 1.26(d, 3H), 1.04(d, 3H) | 447(55), 193(67), 186(78), 151(100), 45(35) |
| 149 | 2-Cl-4-F—C₆H₃ | i-C₃H₇ | 3,4-(CH₃)₂—C₆H₃ | L | 7.35~6.97(m, 6H), 5.01~4.78(m,1H), 4.30(E) 4.19(Z) (dd, 2H), 2.33(s, 6H), 1.26(d, 3H), 1.02(d, 3H) | 461(56), 193(66), 186(88), 151(100), 45(49) |
| 150 | 2-Cl-4-F—C₆H₃ | i-C₃H₇ | 3,5-(CH₃)₂—C₆H₃ | 70~71 | 7.38~6.82(m, 6H), 5.00~4.76(m, 1H), 4.31(E) 4.16(Z) (dd, 2H), 2.30(s, 6H), 1.27(d, 3H), 1.00(d, 3H) | 461(31), 193(64), 186(85), 151(100), 45(54) |
| 151 | 2-Cl-4-F—C₆H₃ | i-C₃H₇ | 3-F—C₆H₄ | L | 7.40~6.95(m, 7H), 5.00~4.79(m, 1H), 4.31(E) 4.17(Z) (dd, 2H), 1.27(d, 3H), 1.02(d, 3H) | 451(40), 193(61), 186(66), 151(100), 45(48) |
| 152 | 2-Cl-4-F—C₆H₃ | i-C₃H₇ | 4-F—C₆H₄ | L | 7.47~6.94(m, 7H), 5.00~4.78(m, 1H), 4.32(E) 4.16(Z) (dd, 2H), 1.26(d, 3H), 1.02(d, 3H) | 451(22), 193(52), 186(73), 151(100), 45(53) |
| 153 | 2-Cl-4-F—C₆H₃ | i-C₃H₇ | 3-Cl—C₆H₄ | L | 7.45~6.98(m, 7H), 5.00~4.79(m, 1H), 4.32(E) 4.16(Z) (dd, 2H), 1.28(d, 3H), 1.04(d, 3H) | 467(39), 193(69), 186(74), 151(100), 45(53) |
| 154 | 2-Cl-4-F—C₆H₃ | i-C₃H₇ | 4-Cl—C₆H₄ | L | 7.44~6.98(m, 7H), 4.98~4.75(m, 1H), 4.30(E) 4.17(Z) (dd, 2H), 1.27(d, 3H), 1.03(d, 3H) | 467(35), 193(71), 186(72), 151(100), 45(60) |
| 155 | 2-Cl-4-F—C₆H₃ | i-C₃H₇ | 3,5-Cl₂—C₆H₃ | L | 7.45~7.01(m, 6H), 5.00~4.78(m, 1H), 4.32(E) 4.15(Z) (dd, 2H), 1.27(d, 3H), 1.03(d, 3H) | 501(41), 193(87), 186(76), 151(100), 45(68) |
| 156 | 3,4-Cl₂—C₆H₃ | i-C₃H₇ | C₆H₃ | 96~97 | 7.60~6.87(m, 8H), 5.04~4.84(m, 1H), 4.30(E) 4.15(Z) (s, 2H), 1.07(d, 6H) | 449(30), 244,(31), 202(100), 167(83), 45(65) |

TABLE 4-continued

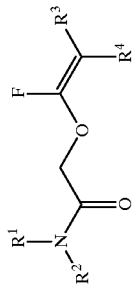
$R^4 = CF_3$ (I)

| Comp. No. | R¹ | R² | R³ | state (° C.) | NMR (CDCl₃, TMS) δ (ppm) | MS (m/e) |
|---|---|---|---|---|---|---|
| 157 | 3,4-Cl₂—C₆H₃ | i-C₃H₇ | 3-F—C₆H₄ | 74~75 | 7.61~6.95(m, 7H), 5.05~4.85(m, 1H), 4.29(E) 4.14(Z) (s, 2H), 1.12(d, 6H) | 467(36), 244(28), 202(100), 174(51), 167(82), 45(68) |
| 158 | 3,4-Cl₂—C₆H₃ | i-C₃H₇ | 4-F—C₆H₄ | L | 7.59~6.87(m, 7H), 5.03~4.84(m, 1H), 4.30(E) 4.16(Z) (s, 2H), 1.09(d, 6H) | 467(20), 202(98), 167(100) |
| 159 | 3,4-Cl₂—C₆H₃ | i-C₃H₇ | 3-Cl—C₆H₄ | L | 7.60~6.92(m, 7H), 5.02~4.82(m, 1H), 4.31(E) 4.15(Z) (s, 2H), 1.08(d, 6H) | 483(42), 244(65), 204(100), 167(72) |
| 160 | 3,4-Cl₂—C₆H₃ | i-C₃H₇ | 4-Cl—C₆H₄ | 44~45 | 7.70~6.90(m, 7H), 5.02~4.85(m, 1H), 4.30(E) 4.15(Z) (s, 2H), 1.07(d, 6H) | 483(12), 244(39), 202(100), 167(54), 45(48) |
| 161 | 3,4-Cl₂—C₆H₃ | i-C₃H₇ | 3,5-Cl₂—C₆H₃ | 80~81 | 7.61~6.95(m, 6H), 5.05~4.86(m, 1H), 4.28(E) 4.14(Z) (s, 2H), 1.09(d, 6H) | 517(8), 202(99), 167(89), 45(100) |
| 162 | 3-CH₃—C₆H₄ | CH₃ | C₆H₅ | L | 7.45~5.90(m, 9H), 4.41(s, 2H), 3.27(s, 3H), 2.36(s, 3H) | 367(15), 162(100), 147(34), 91(32) |
| 163 | 3-CH₃—C₆H₄ | CH₃ | 4-CH₃—C₆H₄ | 54 | 7.32~6.90(m, 8H), 4.39(s, 2H), 3.26(s, 3H), 2.34(s, 3H) | 381(13), 162(100), 147(37), 91(34) |
| 164 | 3-CH₃—C₆H₄ | CH₃ | 4-CH₃O—C₆H₄ | 69 | 7.48~6.79(m, 8H), 4.43(s, 2H), 3.82(s, 3H), 3.48(s, 3H), 2.64(s, 3H) | 397(15), 162(100), 134(42), 91(42), 43(39) |
| 165 | 3-CH₃—C₆H₄ | CH₃ | 4-F—C₆H₄ | L | 7.44~6.93(m, 8H), 4.41(s, 2H), 3.27(s, 3H), 2.38(s, 3H) | 385(16), 162(100), 147(60), 134(74), 91(65) |
| 166 | 3-CH₃—C₆H₄ | CH₃ | 3-CF₃—C₆H₄ | L | 7.82~6.98(m, 8H), 4.49(s, 2H), 3.28(s, 3H), 3.39(s, 3H) | 435(25), 162(100), 147(69), 134(64), 91(69) |
| 167 | 3-CH₃—C₆H₄ | CH₃ | 4-Cl—C₆H₄ | L | 7.40~6.97(m, 8H), 4.42(s, 2H), 3.28(s, 3H), 2.39(s, 3H) | 401(12), 162(100), 147(50), 134(56), 91(48) |
| 168 | 3-CH₃—C₆H₄ | CH₃ | C₆H₄ | 90 | 7.44~6.99(m, 9H), 4.40(s, 2H), 326(s, 3H), 2.38(s, 3H) | 367(15), 162(100), 147(48), 134(46), 91(47) |
| 169 | 4-CH₃—C₆H₄ | CH₃ | 3-CH₃—C₆H₄ | L | 7.30~6.99(m, 8H), 4.41(s, 2H), 3.27(s, 3H), 2.39(s, 3H) | 381(14), 162(100), 147(46), 134(36), 91(32) |
| 170 | 4-CH₃—C₆H₄ | CH₃ | 4-CH₃—C₆H₄ | 108 | 7.33~6.99(m, 8H), 4.39(s, 2H), 3.28(s, 3H), 2.38(s, 3H) | 381(13), 162(100), 147(41), 134(36), 91(27) |
| 171 | 4-CH₃—C₆H₄ | CH₃ | 4-CH₃O—C₆H₄ | 83 | 7.36~6.90(m, 8H), 4.38(s, 2H), 3.80(s, 3H), 3.28(s, 3H), 2.37(s, 3H) | 397(25), 162(100), 147(42), 134(44), 91(43) |
| 172 | 4-CH₃—C₆H₄ | CH₃ | 4-F—C₆H₄ | 71 | 7.44~6.69(m, 8H), 3.27(s, 3H), 2.38(s, 3H) | 385(23), 162(100), 134(46), 91(26) |
| 173 | 4-CH₃—C₆H₄ | CH₃ | 3-Cl—C₆H₄ | L | 7.43~7.02(m, 7H), 4.42(s, 2H), 3.27(s, 3H), 2.38(s, 3H) | 401(11), 162(100), 147(48), 134(38), 91(36) |
| 174 | 4-CH₃—C₆H₄ | CH₃ | 3,5-Cl₂—C₆H₃ | L | 7.35~7.04(m, 7H), 4.45(s, 2H), 3.28(s, 3H), 2.39(s, 3H) | 435(15), 162(100), 147(54), 134(50) |
| 175 | 4-CH₃—C₆H₄ | CH₃ | 4-C₆H₅O—C₆H₄ | 80 | 7.40~6.94(m, 13H), 4.35(s, 2H), 3.27(s, 3H), 2.39(s, 3H) | 459(15), 162(100), 147(33), 134(28) |
| 176 | 4-CH₃—C₆H₄ | CH₃ | 3,4-OCH₂O—C₆H₄ | 68 | 7.26~6.77(m, 7H), 5.95(s, 2H), 4.40(s, 2H), 3.27(s, 3H), 2.38(s, 3H) | 411(15), 162(100), 147(39), 134(32) |

TABLE 4-continued $R^4 = CF_3$ (I)

| Comp. No. | $R^1$ | $R^2$ | $R_3$ | state (° C.) | NMR (CDCl$_3$, TMS) δ (ppm) | MS (m/e) |
|---|---|---|---|---|---|---|
| 177 | 3,4-(CH$_3$)$_2$—C$_6$H$_3$ | CH$_3$ | C$_6$H$_5$ | L | 7.45~6.89(m, 8H), 4.42(s, 2H), 3.27(s, 3H), 2.27(s, 3H) | 381(13), 161(33), 86(72), 84(100) |
| 178 | 3,4-(CH$_3$)$_2$—C$_6$H$_3$ | CH$_3$ | 4-C$_2$H$_5$—C$_6$H$_4$ | L | 7.34~6.90(m, 7H), 4.41(s, 2H), 3.25(s, 3H), 2.28(s, 3H), 2.26(s, 3H) | 395(12), 176(100), 161(96), 43(49) |
| 179 | 3,4-(CH$_3$)$_2$—C$_6$H$_3$ | CH$_3$ | 3,5-(CH$_3$)$_2$—C$_6$H$_3$ | L | 7.24~6.86(m, 6H), 4.37(s, 2H), 3.22(s, 3H), 2.28(s, 6H), 2.25(s, 3H), 2.31(s, 3H) | 409(19), 176(100), 161(65) |
| 180 | 3,4-(CH$_3$)$_2$—C$_6$H$_3$ | CH$_3$ | 4-C$_2$H$_5$—C$_6$H$_4$ | L | 7.37~6.88(m, 7H), 4.41(s, 2H), 3.26(s, 3H), 2.65(q, 2H), 2.30(s, 3H), 2.28(s, 3H), 1.26(t, 3H) | 409(24), 176(100), 161(58) |
| 181 | 3,4-(CH$_3$)$_2$—C$_6$H$_3$ | CH$_3$ | 4-F—C$_6$H$_4$ | L | 7.41~6.83(m, 7H), 4.41(s, 2H), 3.25(s, 3H), 2.26(s, 6H) | 399(18), 176(100), 161(99), 132(22) |
| 182 | 3,4-(CH$_3$)$_2$—C$_6$H$_3$ | CH$_3$ | 4-CF$_3$—C$_6$H$_4$ | L | 7.69~6.86(m, 7H), 4.39(s, 2H), 3.27(s, 3H), 2.89(s, 3H), 2.27(s, 3H) | 449(61), 176(100), 161(84) |
| 183 | 3,4-(CH$_3$)$_2$—C$_6$H$_3$ | CH$_3$ | 3-Cl—C$_6$H$_4$ | L | 7.32~6.81(m, 7H), 4.42(s, 2H), 3.26(s, 3H), 2.29(s, 3H), 2.28(s, 3H) | 415(12), 176(97), 161(100), 84(42) |
| 184 | 3,4-(CH$_3$)$_2$—C$_6$H$_3$ | CH$_3$ | 4-C$_6$H$_5$O—C$_6$H$_4$ | L | 7.40~6.85(m, 12H), 4.42(s, 2H), 3.26(s, 3H), 2.28(s, 3H), 2.27(s, 3H) | 473(25), 176(100), 161(76) |
| 185 | 3,4-(CH$_3$)$_2$—C$_6$H$_3$ | i-C$_3$H$_7$ | C$_6$H$_5$ | 65 | 7.46~6.78(m, 8H), 4.96(m, 1H), 4.30(s, 2H), 2.31(s, 3H), 2.29(s, 3H), 1.06(d, 6H) | 409(36), 204(41), 162(100), 134(40) |
| 186 | 3,4-(CH$_3$)$_2$—C$_6$H$_3$ | i-C$_3$H$_7$ | 4-CH$_3$—C$_6$H$_4$ | L | 7.27~6.77(m, 7H), 4.95(m, 1H), 4.24(s, 2H), 2.35(s, 3H), 2.29(s, 3H), 2.27(s, 3H), 1.05(d, 6H) | 423(48), 204(51), 162(100), 134(33) |
| 187 | 3,4-(CH$_3$)$_2$—C$_6$H$_3$ | i-C$_3$H$_7$ | 4-F—C$_6$H$_4$ | 52 | 7.46~6.78(m, 7H), 4.93(m, 1H), 4.25(s, 2H), 2.28(s, 3H), 2.26(s, 3H), 1.06(d, 6H) | 427(14), 204(37), 162(100), 134(34) |
| 188 | 3,4-(CH$_3$)$_2$—C$_6$H$_3$ | i-C$_3$H$_7$ | 3-Cl—C$_6$H$_4$ | 58 | 7.43~6.79(m, 7H), 4.94(m, 1H), 4.26(s, 2H), 2.29(s, 3H), 2.27(s, 3H), 1.06(d, 6H) | 443(18), 204(33), 162(100), 134(35) |
| 189 | 4-CH$_3$O—C$_6$H$_4$ | CH$_3$ | 4-F—C$_6$H$_4$ | L | 7.44~6.90(m, 8H), 4.39(s, 2H), 3.82(s, 3H), 3.29(s, 3H) | 401(18), 178(100), 147(66), 121(53) |
| 190 | 3-Cl—C$_6$H$_4$ | CH$_3$ | C$_6$H$_5$ | L | 7.42~7.03(m, 9H), 4.41(s, 2H), 3.29(s, 3H) | 387(14), 182(51), 147(100), 118(20) |
| 191 | 3-Cl—C$_6$H$_4$ | CH$_3$ | 3-CH$_3$—C$_6$H$_4$ | L | 7.41~7.01(m, 8H), 4.39(s, 2H), 3.27(s, 3H), 2.25(s, 6H) | 401(14), 182(47), 147(100), 118(20) |
| 192 | 3-Cl—C$_6$H$_4$ | CH$_3$ | 3,4-(CH$_3$)$_2$—C$_6$H$_3$ | L | 7.42~7.02(m, 8H), 4.40(s, 2H), 3.26(s, 3H), 2.25(s, 6H) | 415(17), 182(64), 147(100) |
| 193 | 3-Cl—C$_6$H$_4$ | CH$_3$ | 4-C$_2$H$_5$—C$_6$H$_4$ | L | 7.42~7.02(m, 8H), 4.40(s, 2H), 3.26(s, 3H), 2.64(q, 2H), 1.26(t, 3H) | 415(21), 182(99), 147(100) |
| 194 | 3-Cl—C$_6$H$_4$ | CH$_3$ | 4-t-C$_4$H$_9$—C$_6$H$_4$ | L | 7.42~7.02(m, 8H), 4.41(s, 2H), 3.28(s, 3H), 1.31(s, 9H) | 443(18), 182(72), 147(100) |
| 195 | 3-Cl—C$_6$H$_4$ | CH$_3$ | 4-CH$_3$O—C$_6$H$_4$ | L | 7.43~6.87(m, 8H), 4.40(s, 2H), 3.81(s, 3H), 3.29(s, 3H) | 417(15), 182(52), 147(100), 78(19) |
| 196 | 3-Cl—C$_6$H$_4$ | CH$_3$ | 3-F—C$_6$H$_4$ | L | 7.43~7.02(m, 8H), 4.44(s, 2H), 3.30(s, 3H) | 405(17), 182(38), 147(100) |
| 197 | 3-Cl—C$_6$H$_4$ | CH$_3$ | 4-F—C$_6$H$_4$ | L | 7.43~7.00(m, 8H), 4.36(s, 2H), 3.29(s, 3H) | 405(30), 147(46), 85(60), 84(100), 43(51) |
| 198 | 3-Cl—C$_6$H$_4$ | CH$_3$ | 4-Cl—C$_6$H$_4$ | L | 7.42~7.06(m, 8H), 4.43(s, 2H), 3.28(s, 3H) | 421(13), 182(40), 147(100) |

TABLE 4-continued $$R^4 = CF_3 \quad (I)$$

| Comp. No. | R¹ | R² | R³ | state (° C.) | NMR (CDCl₃, TMS) δ (ppm) | MS (m/e) |
|---|---|---|---|---|---|---|
| 199 | 4-Cl—C₆H₄ | CH₃ | C₆H₅ | 95 | 7.46~7.09(m, 9H), 4.39(s, 2H), 3.29(s, 3H) | 43(26) 387(10), 181(28), 147(100) |
| 200 | 4-Cl—C₆H₄ | CH₃ | 3-CH₃—C₆H₄ | 74 | 7.47~7.05(m, 8H), 4.39(s, 2H), 3.25(s, 3H), 2.35(s, 3H) | 401(19), 182(48), 147(100) |
| 201 | 4-Cl—C₆H₄ | CH₃ | 4-CH₃—C₆H₄ | 99 | 7.48~7.06(m, 8H), 4.38(s, 2H), 3.26(s, 3H), 2.34(s, 3H) | 401(18), 147(71), 84(100), 47(83) |
| 202 | 4-Cl—C₆H₄ | CH₃ | 3,4-(CH₃)₂—C₆H₃ | 76 | 7.43~7.02(m, 7H), 4.35(s, 2H), 3.24(s, 3H), 2.22(s, 6H) | 415(15), 182(59), 147(100) |
| 203 | 4-Cl—C₆H₄ | CH₃ | 4-C₂H₅—C₆H₄ | 85 | 7.46~7.04(m, 8H), 4.38(s, 2H), 3.25(s, 3H), 2.64(q, 2H), 1.22(t, 3H) | 415(14), 182(47), 147(100), 118(24) |
| 204 | 4-Cl—C₆H₄ | CH₃ | 3-CH₃O—C₆H₄ | L | 7.43~6.85(m, 8H), 4.40(s, 2H), 3.81(s, 3H), 3.26(s, 3H) | 417(19), 182(23), 147(100) |
| 205 | 4-Cl—C₆H₄ | CH₃ | 4-CH₃O—C₆H₄ | 90 | 7.43~6.86(m, 8H), 4.31(s, 2H), 3.80(s, 3H), 3.26(s, 3H) | 417(16), 182(47), 147(100) |
| 206 | 4-Cl—C₆H₄ | CH₃ | 3-F—C₆H₄ | L | 7.47~7.01(m, 8H), 4.42(s, 2H), 3.28(s, 3H) | 405(17), 182(42), 147(100) |
| 207 | 4-Cl—C₆H₄ | CH₃ | 4-F—C₆H₄ | 72 | 7.48~7.00(m, 8H), 4.40(s, 2H), 3.26(s, 3H) | 405(18), 182(77), 147(100) |
| 208 | 4-Cl—C₆H₄ | CH₃ | 3-Cl—C₆H₄ | L | 7.47~7.09(m, 8H), 4.41(s, 2H), 3.27(s, 3H) | 421(15), 182(45), 147(100) |
| 209 | 4-Cl—C₆H₄ | CH₃ | 4-Cl—C₆H₄ | 66 | 7.47~7.09(m, 8H), 4.41(s, 2H), 3.28(s, 3H) | 421(18), 182(29), 147(100), 118(29) |
| 210 | 4-Cl—C₆H₄ | CH₃ | thiophene-2-yl | L | 7.47~6.99(m, 7H), 4.45(s, 2H), 3.28(s, 3H) | 393(24), 182(62), 147(100) |
| 211 | C₆H₅ | CH₃ | C₆H₅ | L | 7.51~7.04(m, 10H), 4.32(s, 2H), 3.28(s, 3H) | 403(23), 147(100), 120(94), 91(40) |
| 212 | C₆H₅ | C₂H₅ | C₆H₅ | L | 7.49~7.01(m, 10H), 4.28(s, 2H), 3.75(q, 2H), 1.10(t, 3H) | 417(24), 162(100), 134(94), 106(71), 91(62), 77(57) |
| 213 | C₆H₅ | n-C₃H₇ | C₆H₅ | L | 7.50~7.02(m, 10H), 4.21(s, 2H), 3.67(t, 2H), 1.67~1.45 (m, 2H), 0.91(t, 3H) | 431(63), 180(65), 133(60), 106(100) |
| 214 | C₆H₅ | i-C₃H₇ | C₆H₅ | L | 7.51~7.00(m, 10H), 4.98(m, 1H), 4.10(s, 2H), 1.09(d, 6H) | 431(24), 176(62), 133(100), 120(49) |
| 215 | 4-CH₃O—C₆H₄ | C₂H₅ | C₆H₅ | L | 7.46~6.84(m, 9H), 4.19(s, 2H), 3.81(s, 3H), 3.71(q, 2H), 1.11(t, 3H) | 447(55), 324(53), 239(52), 149(100), 135(55), 120(41) |
| 216 | 4-CH₃O—C₆H₄ | n-C₃H₇ | C₆H₅ | L | 7.47~6.87(m, 9H), 4.26(s, 2H), 3.82(s, 3H), 3.65(t, 2H), 1.67~1.45(m, 2H), 0.90(t, 3H) | 461(43), 206(100), 136(37), 121(54) |
| 217 | 3-CF₃—C₆H₄ | i-C₃H₇ | C₆H₅ | L | 7.76~7.16(m, 9H), 4.94(m, 1H), 4.08(s, 2H), 1.08(d, 6H) | 499(50), 244(46), 202(100), 174(66), 145(26), 43(74) |
| 218 | 4-F—C₆H₄ | i-C₃H₇ | C₆H₅ | L | 7.46~6.97(m, 9H), 4.97(m, 1H), 4.15(s, 2H), 1.02(d, 6H) | 449(21), 194(33), 152(100), 124(45) |
| 219 | 4-Cl—C₆H₄ | C₂H₅ | C₆H₅ | L | 7.49~7.01(m, 9H), 4.20(s, 2H), 3.74(q, 2H), 1.10(t, 3H) | 451(57), 324(47), 219(52), 182(78), 154(100), 139(42) |
| 220 | 2,4-Cl₂—C₆H₄ | CH₃ | C₆H₅ | L | 7.54~7.01(m, 8H), 4.20(s, 2H), 3.21(s, 3H) | 471(41), 436(73), 181(100) |

EXAMPLE 221

Preparation of N-2-(2'-Fluoro-1'-trifluoromethylstyryl-2'-oxy)acetylpiperidine (Compound 221)

The procedure of Example 1 was repeated except that 286 mg(2 mmol) of N-2-hydroxyacetylpiperidine obtained in Preparation 32 and 2,2-difluoro-1-trifluoromethyl styrene obtained in Preparation 56 were used and that silica gel column chromatography was conducted using a mixture of n-hexane and ethyl acetate(2:1) as an eluent to obtain 600 mg(yield 90.6%) of the title compound as a white solid.

$^1$H-NMR (CDCl$_3$, TMS) δ: 7.58–7.17(m, 5H), 4.79(E isomer) 4.67(Z isomer)(s, 2H), 3.17–3.05(m, 4H), 1.78–1.35 (m, 6H); MS (m/e): 331(M$^+$, 40), 126(85), 98(76), 84(100); $^{19}$F-NMR (CDCl$_3$, CFCl$_3$) δ: −57.38(Z isomer) −57.83(E isomer)(d,3F), −82.24(E isomer) −84.28(Z isomer)(q, 1F); m.p.: 78–79° C.

EXAMPLES 222 to 294

Using each of the alcoholic compounds obtained in Preparations 32 to 48 and each of the fluorovinyl compounds obtained in Preparations 49 to 56 and 58 to 65, the procedure of Example 221 was repeated to obtain 73 compounds (Compounds 222 to 294) of formula (I) of the present invention having various R$^1$, R$^2$ and R$^3$ groups listed in Table 5. The $^1$H-NMR and MS data and melting points of these compounds are also shown in Table 5. L in Table 5 represents liquid.

TABLE 5

$$\underset{R^2}{\overset{R^1}{N}}\!\!-\!\!\underset{O}{\overset{}{C}}\!\!-\!\!CH_2\!-\!O\!-\!\underset{F}{\overset{}{C}}\!\!=\!\!\underset{R^4}{\overset{R^3}{C}} \quad R^4 = CF_3 \quad (I)$$

| Comp. No. | R¹ | R² | R³ | state (°C.) | NMR (CDCl₃, TMS) δ (ppm) | MS (m/e) |
|---|---|---|---|---|---|---|
| 221 | —(CH₂)₅— | | C₆H₅ | 78~79 | 7.58~7.17(m, 5H), 4.79(E) 4.67(Z) (s, 2H), 3.71~3.05 (m, 4H), 1.78~1.35(m, 6H) | 331(40), 126(85), 98(76), 84(100) |
| 222 | —(CH₂)₅— | | 3-CH₃—C₆H₄ | L | 7.31~7.04(m, 4H), 4.78(E) 4.66(Z) (s, 2H), 3.64~3.03 (m, 4H), 2.37(s, 3H), 1.74~1.38(m, 6H) | 345(26), 126(71), 98(70), 84(100) |
| 223 | —(CH₂)₅— | | 4-CH₃—C₆H₄ | L | 7.43~7.02(m, 4H), 4.79(E) 4.67(Z) (s, 2H), 3.64~3.01 (m, 4H), 2.43(s, 3H), 1.98~1.17(m, 6H) | 345(23), 326(18), 126(34), 98(100), 84(94) |
| 224 | —(CH₂)₅— | | 4-C₂H₅—C₆H₄ | L | 7.41~7.13(m, 4H), 4.77(E) 4.68(Z) (s, 2H), 3.61~3.06 (m, 4H), 2.64(q, 2H), 1.72~1.38(m, 6H), 1.25(t, 3H) | 359(11), 126(100), 98(51), 84(61) |
| 225 | —(CH₂)₅— | | 3,4-(CH₃)₂—C₆H₃ | L | 7.21~7.00(m, 3H), 4.79(E) 4.67(Z) (s, 2H), 3.60~3.04 (m, 4H), 2.23(s, 6H), 1.70~1.37(m, 6H) | 359(36), 126(85), 98(41), 84(100), 42(30) |
| 226 | —(CH₂)₅— | | 3,5-(CH₃)₂—C₆H₃ | L | 7.03~6.87(m, 3H), 4.78(E) 4.66(Z) (s, 2H), 3.59~3.01 (m, 4H), 2.26(s, 6H), 1.69~1.34(m, 6H) | 359(40), 126(55), 98(63), 84(100), 42(57) |
| 227 | —(CH₂)₅— | | 3-CH₃O—C₆H₄ | L | 7.48~6.72(m, 4H), 4.78(E) 4.66(Z) (s, 2H), 3.82(s, 3H), 3.78~2.98(m, 4H), 1.82-1.43(m, 6H) | 361(23), 126(33), 98(83), 84(100) |
| 228 | —(CH₂)₅— | | 4-CH₃O—C₆H₄ | L | 7.52~6.75(m, 4H), 4.79(E) 4.66(Z) (s, 2H), 3.84(s, 3H), 3.78~3.01(m, 4H), 1.84-1.36(m, 6H) | 361(50), 157(44), 126(100), 98(92), 84(78), 55(69) |
| 229 | —(CH₂)₅— | | 3,4-OCH₂O—C₆H₃ | L | 6.94~6.75(m, 3H), 5.94(s, 2H), 4.78(E) 4.65(Z) (s, 2H), 3.63~3.00(m, 4H), 1.70~1.44(m, 6H) | 375(50), 126(53), 98(60), 84(100), 43(90) |
| 230 | —(CH₂)₅— | | 3-CF₃—C₆H₄ | L | 7.72~7.32(m, 4H), 4.79(E) 4.65(Z) (s, 2H), 3.74~3.02 (m, 4H), 1.97~1.18(m, 6H) | 399(87), 212(47), 127(100) |
| 231 | —(CH₂)₅— | | 3-F—C₆H₄ | L | 7.62~6.89(m, 4H), 4.80(E) 4.68(Z) (s, 2H), 3.75~3.04 (m, 4H), 1.78~0.94(m, 6H) | 349(47), 126(64), 98(100), 84(78) |
| 232 | —(CH₂)₅— | | 4-F—C₆H₄ | L | 7.51~6.95(m, 4H), 4.79(E) 4.67(Z) (s, 2H), 3.62~3.12 (m, 4H), 1.73~1.45(m, 6H) | 349(60), 126(66), 98(56), 42(55) |
| 233 | —(CH₂)₅— | | 3-Cl—C₆H₄ | L | 7.49~7.17(m, 4H), 4.80(E) 4.67(Z) (s, 2H), 3.61~3.07 (m, 4H), 1.72~1.42(m, 6H) | 365(35), 126(32), 98(20), 84(100), 42(38) |
| 234 | —(CH₂)₅— | | 4-Cl—C₆H₄ | L | 7.78~7.34(m, 4H), 4.79(E) 4.66(Z) (s, 2H), 3.85~3.02 (m, 4H), 1.83~1.42(m, 6H) | 365(20), 126(57), 98(41), 84(100), 45(69) |
| 235 | —(CH₂)₅— | | 3,5-Cl₂—C₆H₃ | 54~55 | 7.39~7.15(m, 3H), 4.81(E) 4.70(Z) (s, 2H), 3.60~3.08 (m, 4H), 1.78~1.36(m, 6H) | 399(41), 126(60), 98(42), 84(100) |
| 236 | —(CH₂)₅— | | C₄H₃S-2-yl | L | 7.47~6.94(m, 3H), 4.80(E) 4.70(Z) (s, 2H), 3.82~3.07 (m, 4H), 1.81~1.42(m, 6H) | 337(10), 126(100), 98(74), 84(80) |
| 237 | —CH(CH₃) (CH₂)₄— | | C₆H₅ | L | 7.63~7.18(m, 5H), 4.83(E) 4.74(Z) (s, 2H), 3.25~2.76 (m, 3H), 1.95~1.48(m, 6H), 1.26(d, 3H) | 345(46), 140(52), 98(100), 84(46), 55(63) |
| 238 | —CH(CH₃) (CH₂)₄— | | 3-CH₃—C₆H₄ | L | 7.44~6.92(m, 4H), 4.82(E) 4.75(Z) (s, 2H), 3.18~2.72 (m, 3H), 2.35(s, 3H), 1.95~1.46(m, 6H), 1.29(d, 3H) | 359(65), 242(40), 98(78), 84(92), 56(100) |
| 239 | —CH(CH₃) (CH₂)₄— | | 4-CH₃—C₆H₄ | L | 7.44~7.03(m, 3H), 4.80(E) 4.74(Z) (s, 2H), 3.82~2.45 (m, 3H), 2.42(s, 3H), 1.86~1.42(m, 6H), 1.12(d, 3H) | 359(15), 140(66), 98(100) |
| 240 | —CH(CH₃) (CH₂)₄— | | 3,4-(CH₃)₂—C₆H₃ | L | 7.31~7.03(m, 3H), 4.81(E) 4.74(Z) (s, 2H), 3.24~2.75 | 373(30), 140(86), 98(100) |

TABLE 5-continued $$\begin{array}{c} R^1 \\ | \\ R^2-N \\ \quad\quad \| \\ \quad\quad O \end{array} \begin{array}{c} F \quad R^3 \\ \diagdown / \\ \diagup \diagdown \\ O \quad R^4 \end{array} \quad R^4 = CF_3 \quad (I)$$

| Comp. No. | R¹ | R² | R³ | state (° C.) | NMR (CDCl₃, TMS) δ (ppm) | MS (m/e) |
|---|---|---|---|---|---|---|
| 241 | —CH(CH₃)(CH₂)₄— | | 3,5-(CH₃)₂—C₆H₃ | L | 7.28–6.83(m, 3H), 4.80(E) 4.75(Z) (s, 2H), 3.25–2.74 (m, 3H), 2.28(s, 6H), 1.96–1.45(m, 6H), 1.28(d, 3H) | 373(24), 140(89), 98(100), 55(75) |
| 242 | —CH(CH₃)(CH₂)₄— | | 4-C₂H₅—C₆H₄ | L | 7.52–7.05(m, 4H), 4.81(E) 4.76(Z) (s, 2H), 3.24–2.85 (m, 3H), 2.71(q, 2H), 1.95–1.45(m, 6H), 1.28(t, 3H), 1.15(d, 3H) | 373(45), 140(43), 98(100), 55(43) |
| 243 | —CH(CH₃)(CH₂)₄— | | 3-CH₃O—C₆H₄ | L | 7.47–6.74(m, 4H), 4.79(E) 4.74(Z) (s, 2H), 3.78(s, 3H), 3.24–2.73(m, 3H), 1.95–1.43(m, 6H), 1.24(d, 3H) | 375(20), 140(97), 98(100), 55(84) |
| 244 | —CH(CH₃)(CH₂)₄— | | 4-CH₃O—C₆H₄ | L | 7.54–6.79(m, 4H), 4.80(E) 4.76(Z) (s, 2H), 3.87(s, 3H), 3.22–2.91(m, 3H), 1.97–1.48(m, 6H), 1.33(d, 3H) | 375(20), 140(56), 98(100), 56(32) |
| 245 | —CH(CH₃)(CH₂)₄— | | 3,4-OCH₂O—C₆H₃ | L | 7.20–6.62(m, 3H), 6.01(s, 2H), 4.79(E) 4.75(Z) (s, 2H), 3.23–2.74(m, 3H), 1.97–1.49(m, 6H), 1.29(d, 3H) | 389(19), 219(40), 140(87), 112(74), 98(100), 55(77) |
| 246 | —CH(CH₃)(CH₂)₄— | | 3-CF₃—C₆H₄ | L | 7.76–7.37(m, 4H), 4.78(E) 4.73(Z) (s, 2H), 3.25–2.72 (m, 3H), 1.96–1.42(m, 6H), 1.23(d, 3H) | 413(51), 140(29), 98(62), 84(69), 43(100) |
| 247 | —CH(CH₃)(CH₂)₄— | | 3-F—C₆H₄ | L | 7.53–6.78(m, 4H), 4.79(E) 4.74(Z) (s, 2H), 3.25–2.75 (m, 3H), 1.96–1.46(m, 6H), 1.25(d, 3H) | 363(38), 140(38), 98(100), 55(45) |
| 248 | —CH(CH₃)(CH₂)₄— | | 4-F—C₆H₄ | L | 7.65–6.82(m, 4H), 4.81(E) 4.75(Z) (s, 2H), 3.28–2.65 (m, 3H), 1.95–1.34(m, 6H), 1.16(d, 3H) | 363(50), 140(78), 112(46), 98(100), 55(57) |
| 249 | —CH(CH₃)(CH₂)₄— | | 3-Cl—C₆H₄ | L | 7.58–7.28(m, 4H), 4.80(E) 4.75(Z) (s, 2H), 3.21–2.94 (m, 3H), 1.98–1.49(m, 6H), 1.32(d, 3H) | 379(72), 140(44), 98(100), 56(57) |
| 250 | —CH(CH₃)(CH₂)₄— | | 4-Cl—C₆H₄ | L | 7.57–7.18(m, 4H), 4.81(E) 4.74(Z) (s, 2H), 3.18–2.74 (m, 3H), 1.75–1.35(m, 6H), 1.15(d, 3H) | 379(35), 140(70), 98(100), 55(47) |
| 251 | —CH(CH₃)(CH₂)₄— | | 3,5-Cl₂—C₆H₃ | L | 7.64–7.18(m, 3H), 4.80(E) 4.75(Z) (s, 2H), 3.24–2.75 (m, 3H), 1.95–1.44(m, 4H), 1.23(d, 3H) | 413(35), 140(49), 98(100), 55(57) |
| 252 | —CH(CH₃)(CH₂)₄— | | C₄H₃S-2-yl | L | 7.45–6.91(m, 3H), 4.79(E) 4.74(Z) (s, 2H), 3.26–2.73 (m, 3H), 1.97–1.41(m, 4H), 1.24(d, 3H) | 351(20), 140(65), 98(100), 55(66), 41(47) |
| 253 | —CH(C₂H₅)(CH₂)₃CH(CH₃)— | | C₆H₅ | L | 7.48–7.22(m, 5H), 4.80(E) 4.75(Z) (s, 2H), 3.58–2.62 (m, 3H), 1.81–1.21(m, 8H), 0.83(t, 3H) | 359(18), 154(100), 126(58), 112(98) |
| 254 | —CH(C₂H₅)(CH₂)₃CH(CH₃)— | | 4-CH₃—C₆H₄ | L | 7.43–7.02(m, 4H), 4.81(E) 4.76(Z) (s, 2H), 4.01–2.52 (m, 3H), 2.41(s, 3H), 1.98–1.12(m, 8H), 0.92(t, 3H) | 373(30), 354(15), 154(43), 112(100) |
| 255 | —CH(C₂H₅)(CH₂)₃CH(CH₃)— | | 3-Cl—C₆H₄ | L | 7.59–7.15(m, 4H), 4.80(E) 4.75(Z) (s, 2H), 4.54–3.91 (m, 2H), 3.43–3.12(m, 3H), 1.95–1.23(m, 6H), 1.04(t, 3H) | 393(71), 154(41), 112(100), 97(38), 55(61) |
| 256 | —CH(C₂H₅)(CH₂)₃CH(CH₃)— | | 4-CH₃—C₆H₄ | L | 7.49–7.01(m, 4H), 4.80(E) 4.75(Z) (s, 2H), 4.54–3.96 (m, 2H), 2.42(s, 3H), 1.98–1.51(m, 6H), 1.42(d, 6H) | 373(49), 354(21), 217(100), 153(48), 69(21) |
| 257 | —CH(C₂H₅)(CH₂)₃CH(CH₃)— | | 3-Cl—C₆H₄ | 58–59 | 7.62–7.18(m, 4H), 4.81(E) 4.75(Z) (s, 2H), 3.75–2.76 (m, 2H), 1.98–1.48(m, 6H), 1.42(d, 6H) | 393(60), 154(30), 112(100), 69(45), 55(62) |
| 258 | —CH(C₂H₅)(CH₂)₃CH(CH₃)— | | 3,5-Cl₂—C₆H₃ | 98–99 | 7.45–7.21(m, 3H), 4.80(E) 4.76(Z) (s, 2H), 3.78–3.54 (m, 2H), 1.98–1.47(m, 6H), 1.28(d, 6H) | 427(20), 154(60), 112(100), 69(64), 55(80) |
| 259 | —(CH₂)₂CH=CHCH₂— | | 4-CH₃—C₆H₄ | L | 7.51–7.10(m, 4H), 5.92–5.62(m, 2H), 4.81(E) 4.74(Z) | 343(10), 324(48), 124(74) |

TABLE 5-continued (I)

$$\begin{array}{c} R^1 \\ | \\ R^2-N \\ \phantom{xxx} \diagdown \\ \phantom{xxxxx} O \end{array} \cdots O-C(F)=C(R^3)(R^4) \quad R^4=CF_3$$

| Comp. No. | R¹ | R² | R³ | state | (°C.) | NMR (CDCl₃, TMS) δ (ppm) | MS (m/e) |
|---|---|---|---|---|---|---|---|
| 260 | —(CH₂)₂O(CH₂)₂— | | C₆H₅ | L | | (s, 2H), 4.18–3.32(m, 4H), 2.43(s, 3H), 2.42–1.91(m, 2H) | 333(10), 129(69), 102(100) 96(42), 82(100) |
| 261 | —(CH₂)₂O(CH₂)₂— | | 4-CH₃—C₆H₄ | | 75~76 | 7.43–7.02(m, 4H), 4.81(E) 4.76(Z) (s, 2H), 4.02–3.10 (m, 8H), 2.41(s, 3H) | 347(15), 128(48), 100(100) 87(30) |
| 262 | —(CH₂)₃C(C₆H₄)C— | | C₆H₅ | | 72~73 | 7.45–7.10(m, 9H), 4.80(E) 4.74(Z) (s, 2H), 3.79(t, 2H), 2.70(t, 2H), 2.06–1.87(m, 2H) | 379(14), 360(15), 174(70), 146(70), 118(100) |
| 263 | —(CH₂)₃C(C₆H₄)C— | | 4-CH₃—C₆H₄ | L | | 7.49–7.02(m, 8H), 4.81(E) 4.76(Z) (s, 2H), 3.78(t, 2H), 2.71(t, 2H), 2.42(s, 3H), 2.05–1.86(m, 2H) | 393(38), 374(28), 174(89), 146(96), 118(100) |
| 264 | —(CH₂)₆— | | C₆H₅ | L | | 7.50–7.25(m, 5H), 4.80(E) 4.75(Z) (s, 2H), 3.60–3.10 (m, 4H), 1.81–1.45(m, 8H) | 345(16), 147(100), 112(46) 99(26) |
| 265 | —(CH₂)₆— | | 3-CH₃—C₆H₄ | L | | 7.38–7.08(m, 4H), 4.81(E) 4.76(Z) (s, 2H), 3.60–3.13 (m, 4H), 2.31(s, 3H), 1.78–1.38(m, 8H) | 359(15), 140(44), 98(100), 43(63) |
| 266 | —(CH₂)₆— | | 4-CH₃—C₆H₄ | L | | 7.40–7.10(m, 4H), 4.80(E) 4.75(Z) (s, 2H), 3.60–3.12 (m, 4H), 2.38(s, 3H), 1.81–1.48(m, 8H) | 359(13), 140(56), 97(53), 55(53), 43(100) |
| 267 | —(CH₂)₆— | | 4-C₂H₅—C₆H₄ | L | | 7.40–7.12(m, 4H), 4.81(E) 4.75(Z) (s, 2H), 3.60–3.15 (m, 4H), 2.65(q, 2H), 1.85–1.48(m, 8H), 1.26(t, 3H) | 373(23), 140(100), 98(54) |
| 268 | —(CH₂)₆— | | 3,4-(CH₃)₂—C₆H₃ | L | | 7.24–7.02(m, 3H), 4.79(E) 4.74(Z) (s, 2H), 3.58–3.11 (m, 4H), 2.32(s, 6H), 1.77–1.41(m, 8H) | 373(71), 140(51), 98(100) |
| 269 | —(CH₂)₆— | | 3,5-(CH₃)₂—C₆H₃ | L | | 7.06–6.91(m, 3H), 4.80(E) 4.75(Z) (s, 2H), 3.60–3.12 (m, 4H), 2.30(s, 6H), 1.80–1.44(m, 8H) | 373(31), 140(39), 98(100), 42(39) |
| 270 | —(CH₂)₆— | | 3-CH₃O—C₆H₃ | L | | 7.29–6.76(m, 4H), 4.80(E) 4.75(Z) (s, 2H), 3.61–3.17 (m, 4H), 3.74(s, 3H), 3.54–3.10(m, 4H), 1.78–1.42(m, 8H) | 375(53), 140(55), 98(100), 43(56) |
| 271 | —(CH₂)₆— | | 4-CH₃O—C₆H₄ | L | | 7.38–6.80(m, 4H), 4.79(E) 4.74(Z) (s, 2H), 3.76(s, 3H), 3.58–3.12(m, 4H), 1.81–1.46(m, 8H) | 375(21), 140(29), 98(44), 59(38), 43(100) |
| 272 | —(CH₂)₆— | | 3,4-OCH₂O—C₆H₃ | L | | 7.15–6.78(m, 3H), 5.97(s, 2H), 4.80(E) 4.75(Z) (s, 2H), 3.75–3.14(m, 4H), 1.98–1.32(m, 8H) | 389(13), 140(70), 98(100) |
| 273 | —(CH₂)₆— | | 3-F—C₆H₄ | L | | 7.40–6.98(m, 4H), 4.79(E) 4.74(Z) (s, 2H), 3.61–3.16 (m, 4H), 1.81–1.48(m, 8H) | 363(51), 140(42), 98(100), 55(54), 42(65) |
| 274 | —(CH₂)₆— | | 4-F—C₆H₄ | L | | 7.50–6.98(m, 4H), 4.80(E) 4.75(Z) (s, 2H), 3.60–3.15 (m, 4H), 1.81–1.46(m, 8H) | 363(51), 140(45), 98(96), 55(58), 42(100) |
| 275 | —(CH₂)₆— | | 3-Cl—C₆H₄ | L | | 7.49–7.18(m, 4H), 4.81(E) 4.74(Z) (s, 2H), 3.62–3.20 (m, 4H), 1.82–1.50(m, 8H) | 379(55), 140(52), 98(93), 55(73), 42(100) |
| 276 | —(CH₂)₆— | | 4-Cl—C₆H₄ | L | | 7.50–7.15(m, 4H), 4.80(E) 4.75(Z) (s, 2H), 3.61–3.17 (m, 4H), 1.83–1.43(m, 8H) | 379(56), 140(51), 98(82), 55(70), 42(100) |
| 277 | —(CH₂)₆— | | 3,5-Cl₂—C₆H₃ | L | | 7.43–7.16(m, 3H), 4.80(E) 4.79(Z) (s, 2H), 3.63–3.18 (m, 4H), 1.86–1.47(m, 8H) | 413(45), 140(48), 98(100), 42(53) |
| 278 | —(CH₂)₆— | | C₄H₃S-2-yl | L | | 7.40–6.94(m, 3H), 4.79(E) 4.75(Z) (s, 2H), 3.61–3.13 (m, 4H), 1.82–1.43(m, 8H) | 351(11), 140(50), 98(100), 55(31), 42(41) |

TABLE 5-continued (I) structure: R¹R²N-C(=O)-CH₂-O-C(F)=C(R³)(R⁴), R⁴ = CF₃

| Comp. No. | R¹ | R² | R³ | state (° C.) | NMR (CDCl₃, TMS) δ (ppm) | MS (m/e) |
|---|---|---|---|---|---|---|
| 279 | C₂H₅ | C₂H₅ | C₆H₅ | L | 7.50~7.21(m, 5H), 4.77(E) 4.64(Z) (s, 2H), 3.45(q, 4H), 1.15(t, 6H) | 319(28), 114(88), 86(62), 72(100) |
| 280 | C₂H₅ | C₂H₅ | 4-CH₃—C₆H₄ | L | 7.45~6.98(m, 4H), 4.78(E) 4.65(Z) (s, 2H), 3.45(q, 4H), 2.38(s, 3H), 1.10(t, 6H) | 333(39), 314(75), 219(100), 72(82) |
| 281 | n-C₃H₇ | n-C₃H₇ | 4-CH₃—C₆H₄ | L | 7.46~6.97(m, 4H), 4.77(E) 4.65(Z) (s, 2H), 3.21(t, 4H), 2.37(s, 3H), 1.98~1.23(m, 4H), 0.91(t, 6H) | 361(43), 342(52), 261(100), 100(23), 69(58) |
| 282 | i-C₃H₇ | i-C₃H₇ | 4-CH₃—C₆H₄ | 73~74 | 7.45~6.98(m, 4H), 4.78(E) 4.66(Z) (s, 2H), 3.82~3.32 (m, 2H), 2.38(s, 3H), 1.38(d, 12H) | 361(52), 342(40), 261(100), 158(49) |
| 283 | CH₂=CHCH₂ | CH₂=CHCH₂ | C₆H₅ | L | 7.49~7.19(m, 5H), 5.86~5.59(m, 2H), 5.30~5.02(m, 4H), 4.79(E) 4.66(Z) (s, 2H), 4.10~3.62(m, 4H) | 343(19), 138(92), 110(63), 55(100) |
| 284 | CH₂=CHCH₂ | CH₂=CHCH₂ | 4-CH₃—C₆H₄ | L | 7.51~6.97(m, 4H), 5.89~5.42(m, 2H), 5.39~4.98(m, 4H), 4.77(E) 4.65(Z) (s, 2H), 4.18~3.48(m, 4H), 2.38(s, 3H) | 357(40), 138(54), 55(100) |
| 285 | CH₂=CHCH₂ | CH₂=CHCH₂ | 3-CH₃O—C₆H₄ | L | 7.51~6.81(m, 4H), 6.10~5.51(m, 2H), 5.49~4.98(m, 4H), 4.79(E) 4.66(Z) (s, 2H), 4.10~3.62(m, 4H), 3.82(s, 3H) | 373(66), 354(23), 138(41), 56(100) |
| 286 | CH₂=CHCH₂ | CH₂=CHCH₂ | 3-CF₃—C₆H₄ | L | 7.89~7.21(m, 4H), 5.94~5.42(m, 2H), 5.39~4.96(m, 4H), 4.79(E) 4.65(Z) (s, 2H), 4.18~3.48(m, 4H) | 411(69), 195(100), 138(80), 110(51) |
| 287 | CH₂=CHCH₂ | CH₂=CHCH₂ | C₄H₃S-2-yl | L | 7.50~6.91(m, 3H), 6.11~5.50(m, 2H), 5.50~4.97(m, 4H), 4.78(E) 4.66(Z) (s, 2H), 4.12~3.61(m, 4H) | 349(13), 183(30), 138(100), 133(48) |
| 288 | n-C₄H₉ | n-C₄H₉ | 4-CH₃—C₆H₄ | L | 7.48~6.97(m, 4H), 4.79(E) 4.66(Z) (s, 2H), 3.21(t, 4H), 2.38(s, 3H), 1.82~1.10(m, 8H), 0.94(t, 6H) | 389(42), 370(21), 203(100), 186(72), 69(48) |
| 289 | i-C₄H₉ | i-C₄H₉ | 4-CH₃—C₆H₄ | L | 7.45~6.98(m, 4H), 4.79(E) 4.65(Z) (s, 2H), 2.83(d, 4H), 2.37(s, 3H), 2.04~1.37(m, 2H), 0.89(d, 12H) | 389(14), 170(17), 128(100), 72(34) |
| 290 | C₂H₅ | (CH₃)₂CH | C₆H₅ | L | 7.71~7.28(m, 5H), 4.78(E) 4.64(Z) (s, 2H), 3.98~3.63 (m, 1H), 3.12(q, 2H), 1.12(t, 3H), 1.10(d, 6H) | 333(12), 205(40), 128(62), 86(100), 57(71) |
| 291 | CH₃ | n-C₄H₉ | 4-CH₃—C₆H₄ | L | 7.44~6.97(m, 4H), 4.79(E) 4.64(Z) (s, 2H), 3.35(t, 2H), 2.82(s, 3H), 2.28(s, 3H), 1.45~1.30(m, 4H), 0.98(t, 3H) | 347(28), 328(16), 203(100), 144(67), 69(21) |
| 292 | C₂H₅ | n-C₄H₉ | 4-CH₃—C₆H₄ | L | 7.45~6.96(m, 4H), 4.79(E) 4.65(Z) (s, 2H), 3.40(t, 2H), 3.21(q, 2H), 2.28(s, 3H), 1.46~1.31(m, 4H), 1.10(t, 3H), 0.97(t, 3H) | 361(27), 342(12), 203(100), 158(39), 69(13) |
| 293 | CH₃ | (C₆H₅)CH₂ | C₆H₅ | L | 7.49~7.01(m, 10H), 4.80(E) 4.66(Z) (s, 2H), 4.41(s, 2H), 2.82(s, 3H) | 367(32), 164(100), 93(54), 47(98) |
| 294 | CH₃ | (C₆H₅)CH₂ | 4-CH₃—C₆H₄ | L | 7.48~6.98(m, 9H), 4.81(E) 4.67(Z) (s, 2H), 4.43(s, 2H), 2.84(s, 3H), 2.42(s, 3H) | 381(25), 162(68), 91(100), 44(28) |

Herbicidal Activity Test

Herbicidal activity tests were conducted using test plants planted in screening pots as follows.

Each of screening pots, having the shape of a cube and a top surface area of 140 cm$^2$, was filled with a wet mixture of paddy soil and a suitable amount of fertilizer, and sowed thereto were 100 barnyardgrass seeds, 20 bulrush seeds, 50 monochoria seeds, 2 flat-sedge tubers and 2 arrow head tubers(see Table 6). Two rice plant seedlings at the 3-leaf stage were then transplanted thereto, followed by filling water to a depth of 3 cm and kept in a greenhouse for 2 days.

Added to each of the screening pots thus prepared was 4 ml of a 50% acetone solution containing 0.1% Tween-20 and a predetermined amount of each of the compounds listed in Tables 4 and 5 so that the amount of the compound applied would correspond to 4, 1, 0.25, 0.0625 or 0.015 kg/ha. Then, the pot was kept in a greenhouse for 2 to 3 weeks.

The herbicidal activity was determined according to the procedure of Table 7 which was described by Frans et al., *In research methods in weed science*, ed. by Camper, 29–70 (1986) and Cho, K. Y., *Search Report by Korea Research Institute of Chemical Technology*, 916 (1989))". The results are shown in Table 8.

TABLE 6

| Abbreviation | Genus-species name | General name |
|---|---|---|
| ORYSA | *Oryza sativa* L. | Rice |
| ECHOR | *Echinochlora crus-galli* 8P. BEAUV. var. *oryzicola* OHWI | Barnyardgrass |
| SCPJU | *Scirpus juncoides* ROXB | Bulrush |
| MOOVA | *Monochoria vaginalis* PRESL | Monochoria |
| CYPSE | *Cyperus serotinus* ROTTB | Flat-sedge |
| SAGPY | *Sagittaria pygmaea* MIQ | Arrow head |

TABLE 7

| Score | General Description | Rice | Weed |
|---|---|---|---|
| 0 | no effect | no damage | no preventive effect |
| 10 | week | week | a slight damage | a slight damage |
| 20 | | medium | that can be | but no preventive |
| 30 | | strong | recovered; no significant influence on the harvest | effect |
| 40 | medium | week | a visible damage | a significant preventive effect |
| 50 | | medium | that can be recovered but would reduce the harvest | |
| 60 | | strong | | |
| 70 | strong | week | a severe damage | a practically high |
| 80 | | medium | that can not | preventive effect, |
| 90 | | strong | be recovered, and extinction at a score of 80 or higher | and eradication at a score of 80 or higher |
| 100 | complete | | complete total destruction | complete eradication |

TABLE 8

| Comp. No. | amount (kg/ha) | ORYSA | ECHOR | SCPJU | MOOVA | CYPSE | SAGPY |
|---|---|---|---|---|---|---|---|
| 1 | 4.0000 | 90 | 100 | 100 | 100 | 100 | 100 |
|   | 1.0000 | 60 | 100 | 100 | 100 | 100 | 50 |
|   | 0.2500 | 10 | 100 | 10 | 90 | 40 | 50 |
|   | 0.0625 | 0 | 100 | 0 | 80 | 40 | 20 |
|   | 0.0156 | 0 | 60 | 0 | 40 | 10 | 0 |
| 2 | 1.0000 | 90 | 100 | 100 | 100 | — | 70 |
|   | 0.2500 | 40 | 100 | 70 | 90 | — | 60 |
|   | 0.0625 | 0 | 100 | 40 | 90 | — | 0 |
|   | 0.0156 | 0 | 100 | 20 | 90 | — | 0 |
|   | 0.0040 | 0 | 75 | 0 | 60 | — | 0 |
| 3 | 1.0000 | 80 | 100 | 100 | 100 | — | 70 |
|   | 0.2500 | 10 | 100 | 90 | 100 | — | 50 |
|   | 0.0625 | 0 | 100 | 70 | 80 | — | 20 |
|   | 0.0156 | 0 | 100 | 20 | 60 | — | 0 |
|   | 0.0040 | 0 | 60 | 0 | 20 | — | 0 |
| 4 | 1.0000 | 70 | 100 | 70 | 100 | 100 | 20 |
|   | 0.2500 | 10 | 100 | 70 | 100 | 100 | 0 |
|   | 0.0625 | 0 | 100 | 70 | 100 | 80 | 0 |
|   | 0.0156 | 0 | 100 | 50 | 100 | 0 | 0 |
|   | 0.0040 | 0 | 20 | 0 | 0 | 0 | 0 |
| 5 | 1.0000 | 20 | 100 | 100 | 100 | 100 | 60 |
|   | 0.2500 | 10 | 100 | 30 | 100 | 100 | 0 |
|   | 0.0625 | 0 | 100 | 0 | 100 | 0 | 0 |
|   | 0.0156 | 0 | 95 | 0 | 90 | 0 | 0 |
|   | 0.0040 | 0 | 50 | 0 | 10 | 0 | 0 |
| 6 | 1.0000 | 20 | 100 | 100 | 100 | 100 | 60 |
|   | 0.2500 | 0 | 100 | 0 | 90 | 100 | |
|   | 0.0625 | 0 | 95 | 0 | 50 | 0 | 0 |
|   | 0.0156 | 0 | 60 | 0 | 0 | 0 | 0 |
|   | 0.0040 | 0 | 0 | 0 | 0 | 0 | 0 |
| 7 | 1.0000 | 10 | 100 | 100 | 100 | — | 30 |
|   | 0.2500 | 0 | 100 | 100 | 100 | — | 30 |
|   | 0.0625 | 0 | 80 | 30 | 70 | — | 10 |
|   | 0.0156 | 0 | 60 | 0 | 40 | — | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0040 | 0 | 0 | 0 | 0 | — | 0 |
| 8 | 1.0000 | 0 | 100 | 20 | 90 | 30 | 70 |
| | 0.2500 | 0 | 100 | 0 | 90 | 30 | 0 |
| | 0.0625 | 0 | 95 | 0 | 0 | 10 | 0 |
| | 0.0156 | 0 | 30 | 0 | 0 | 0 | 0 |
| | 0.0040 | 0 | 0 | 0 | 0 | 0 | 0 |
| 9 | 4.0000 | 80 | 100 | 100 | 100 | 0 | 100 |
| | 1.0000 | 50 | 100 | 60 | 100 | 0 | 60 |
| | 0.2500 | 30 | 100 | 0 | 100 | 0 | 40 |
| | 0.0625 | 0 | 100 | 0 | 100 | 0 | 0 |
| | 0.0156 | 0 | 100 | 0 | 100 | 0 | 0 |
| 10 | 1.0000 | 20 | 100 | 100 | 100 | 100 | 0 |
| | 0.2500 | 10 | 100 | 40 | 70 | 100 | 0 |
| | 0.0625 | 0 | 100 | 0 | 30 | 10 | 0 |
| | 0.0156 | 0 | 50 | 0 | 0 | 0 | 0 |
| | 0.0040 | 0 | 0 | 0 | 0 | 0 | 0 |
| 11 | 4.0000 | 60 | 100 | 100 | 100 | 100 | 80 |
| | 1.0000 | 10 | 100 | 100 | 100 | 100 | 50 |
| | 0.2500 | 0 | 100 | 30 | 90 | 100 | 10 |
| | 0.0625 | 0 | 90 | 10 | 60 | 100 | 0 |
| | 0.0156 | 0 | 60 | 0 | 0 | 0 | 0 |
| 12 | 1.0000 | 0 | 100 | 100 | 100 | 100 | 50 |
| | 0.2500 | 0 | 100 | 10 | 90 | 100 | 0 |
| | 0.0625 | 0 | 100 | 0 | 60 | 10 | 0 |
| | 0.0156 | 0 | 60 | 0 | 0 | 0 | 0 |
| | 0.0040 | 0 | 0 | 0 | 0 | 0 | 0 |
| 13 | 4.0000 | 40 | 100 | 70 | 100 | 0 | 100 |
| | 1.0000 | 30 | 100 | 40 | 100 | 0 | 100 |
| | 0.2500 | 0 | 100 | 0 | 100 | 0 | 100 |
| | 0.0625 | 0 | 95 | 0 | 80 | 0 | 100 |
| | 0.0156 | 0 | 70 | 0 | 40 | 0 | 0 |
| 14 | 1.0000 | 50 | 100 | 100 | 100 | 100 | 70 |
| | 0.2500 | 10 | 100 | 40 | 90 | 100 | 20 |
| | 0.0625 | 0 | 100 | 20 | 70 | 50 | 0 |
| | 0.0156 | 0 | 80 | 0 | 20 | 0 | 0 |
| | 0.0040 | 0 | 50 | 0 | 0 | 0 | 0 |
| 15 | 1.0000 | 60 | 100 | 100 | 100 | 100 | 100 |
| | 0.2500 | 0 | 100 | 30 | 100 | 100 | 30 |
| | 0.0625 | 0 | 100 | 0 | 90 | 100 | 20 |
| | 0.0156 | 0 | 90 | 0 | 30 | 20 | 0 |
| | 0.0040 | 0 | 70 | 0 | 0 | 0 | |
| 16 | 1.0000 | 30 | 100 | 100 | 100 | 100 | 50 |
| | 0.2500 | 10 | 100 | 50 | 100 | 50 | |
| | 0.0625 | 0 | 100 | 50 | 100 | 0 | 0 |
| | 0.0156 | 0 | 40 | 0 | 0 | 0 | 0 |
| | 0.0040 | 0 | 0 | 0 | 0 | 0 | 0 |
| 17 | 1.0000 | 30 | 100 | 20 | 100 | 100 | 20 |
| | 0.2500 | 10 | 100 | 0 | 100 | 100 | 20 |
| | 0.0625 | 0 | 100 | 0 | 100 | 100 | 20 |
| | 0.0156 | 0 | 90 | 0 | 100 | 40 | 0 |
| | 0.0040 | 0 | 20 | 0 | 0 | 0 | 0 |
| 18 | 4.0000 | 0 | 100 | 30 | 90 | 50 | 20 |
| | 1.0000 | 0 | 100 | 70 | 90 | 0 | — |
| | 0.2500 | 0 | 70 | 40 | 80 | 0 | 0 |
| | 0.0625 | 0 | 10 | 0 | 0 | 0 | 0 |
| | 0.0156 | 0 | 0 | 0 | 0 | 0 | 0 |
| 19 | 4.0000 | 50 | 100 | 100 | 100 | — | 100 |
| | 1.0000 | 40 | 100 | 100 | 100 | — | 100 |
| | 0.2500 | 40 | 100 | 70 | 100 | — | 0 |
| | 0.0625 | 20 | 95 | — | 100 | — | 0 |
| | 0.0156 | 0 | 70 | 0 | 40 | — | 0 |
| 20 | 4.0000 | 60 | 100 | 100 | 100 | 100 | 70 |
| | 1.0000 | 30 | 100 | 100 | 100 | 100 | 50 |
| | 0.2500 | 10 | 100 | 10 | 90 | 30 | 0 |
| | 0.0625 | 0 | 100 | 0 | 80 | 20 | 0 |
| | 0.0156 | 0 | 60 | 0 | 30 | 0 | 0 |
| 21 | 1.0000 | 45 | 100 | 80 | 100 | 100 | 10 |
| | 0.2500 | 10 | 100 | 40 | 100 | 100 | 0 |
| | 0.0625 | 0 | 95 | 10 | 60 | 0 | 0 |
| | 0.0156 | 0 | 60 | 0 | 0 | 0 | 0 |
| | 0.0040 | 0 | 30 | 0 | 0 | 0 | 0 |
| 22 | 4.0000 | 20 | 100 | 50 | 100 | 100 | 0 |
| | 1.0000 | 0 | 100 | 30 | 100 | 100 | 0 |
| | 0.2500 | 0 | 100 | 30 | 90 | 20 | 0 |
| | 0.0625 | 0 | 100 | 30 | 60 | 0 | 0 |
| | 0.0156 | 0 | 60 | 0 | 40 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| 23 | 1.0000 | 30 | 100 | 0 | 90 | 60 | 70 |
|  | 0.2500 | 0 | 100 | 0 | 70 | 0 | 0 |
|  | 0.0625 | 0 | 95 | 0 | 50 | 0 | 0 |
|  | 0.0156 | 0 | 40 | 0 | 0 | 0 | 0 |
|  | 0.0040 | 0 | 0 | 0 | 0 | 0 | 0 |
| 24 | 1.0000 | 30 | 100 | 40 | 100 | 0 | 0 |
|  | 0.2500 | 10 | 100 | 20 | 70 | 0 | 0 |
|  | 0.0625 | 0 | 90 | 0 | 50 | 0 | 0 |
|  | 0.0156 | 0 | 30 | 0 | 0 | 0 | 0 |
|  | 0.0040 | 0 | 10 | 0 | 0 | 0 | 0 |
| 25 | 1.0000 | 10 | 100 | 40 | 100 | 100 | 50 |
|  | 0.2500 | 0 | 90 | 0 | 50 | 100 | 0 |
|  | 0.0625 | 0 | 80 | 0 | 0 | 100 | 0 |
|  | 0.0156 | 0 | 70 | 0 | 0 | 0 | 0 |
|  | 0.0040 | 0 | 0 | 0 | 0 | 0 | 0 |
| 26 | 1.0000 | 40 | 100 | 50 | 90 | 0 | 0 |
|  | 0.2500 | 10 | 100 | 40 | 90 | 0 | 0 |
|  | 0.0625 | 0 | 95 | 30 | 70 | 0 | 0 |
|  | 0.0156 | 0 | 70 | 20 | 50 | 0 | 0 |
|  | 0.0040 | 0 | 0 | 0 | 20 | 0 | 0 |
| 27 | 1.0000 | 20 | 100 | 20 | 100 | 100 | 10 |
|  | 0.2500 | 10 | 100 | 0 | 90 | 50 | 0 |
|  | 0.0625 | 0 | 80 | 0 | 30 | 30 | 0 |
|  | 0.0156 | 0 | 10 | 0 | 0 | 0 | 0 |
|  | 0.0040 | 0 | 0 | 0 | 0 | 0 | 0 |
| 28 | 1.0000 | 20 | 100 | 10 | 100 | 100 | 30 |
|  | 0.2500 | 0 | 100 | 0 | 100 | 0 | 0 |
|  | 0.0625 | 0 | 100 | 0 | 100 | 0 | 0 |
|  | 0.0156 | 0 | 50 | 0 | 0 | 0 | 0 |
|  | 0.0040 | 0 | 0 | 0 | 0 | 0 | 0 |
| 30 | 1.0000 | 60 | 100 | 100 | 100 | — | 100 |
|  | 0.2500 | 50 | 100 | 100 | 100 | — | 60 |
|  | 0.0625 | 40 | 100 | 30 | 90 | — | 50 |
|  | 0.0156 | 0 | 80 | 10 | 70 | — | 0 |
|  | 0.4000 | 0 | 50 | 0 | 20 | — | 0 |
| 31 | 1.0000 | 40 | 100 | 80 | 100 | — | 30 |
|  | 0.2500 | 20 | 100 | 50 | 90 | — | 0 |
|  | 0.0625 | 0 | 95 | 0 | 80 | — | 0 |
|  | 0.0156 | 0 | 70 | 0 | 50 | — | 0 |
|  | 0.0040 | 0 | 10 | 0 | 0 | — | 0 |
| 32 | 1.0000 | 40 | 100 | 100 | 100 | — | 40 |
|  | 0.2500 | 30 | 100 | 100 | 100 | — | 20 |
|  | 0.0625 | 0 | 90 | 20 | 80 | — | 0 |
|  | 0.0156 | 0 | 60 | 0 | 20 | — | 0 |
|  | 0.0040 | 0 | 20 | 0 | 0 | — | 0 |
| 33 | 1.0000 | 20 | 100 | 50 | 100 | — | 30 |
|  | 0.2500 | 0 | 100 | 30 | 80 | — | 0 |
|  | 0.0625 | 0 | 80 | 0 | 70 | — | 0 |
|  | 0.0156 | 0 | 40 | 0 | 20 | — | 0 |
|  | 0.0040 | 0 | 0 | 0 | 0 | — | 0 |
| 34 | 1.0000 | 20 | 100 | 100 | 100 | — | 20 |
|  | 0.2500 | 10 | 100 | 80 | 100 | — | 10 |
|  | 0.0625 | 0 | 90 | 10 | 70 | — | 10 |
|  | 0.0156 | 0 | 70 | 0 | 50 | — | 0 |
|  | 0.0040 | 0 | 0 | 0 | 0 | — | 0 |
| 35 | 1.0000 | 20 | 100 | 100 | 100 | — | 50 |
|  | 0.2500 | 0 | 100 | 50 | 90 | — | 0 |
|  | 0.0625 | 0 | 80 | 30 | 70 | — | 0 |
|  | 0.0156 | 0 | 50 | 0 | 50 | — | 0 |
|  | 0.0040 | 0 | 10 | 0 | 20 | — | 0 |
| 36 | 1.0000 | 40 | 100 | 100 | 100 | — | 60 |
|  | 0.2500 | 0 | 100 | 20 | 90 | — | 60 |
|  | 0.0625 | 0 | 90 | 10 | 80 | — | 20 |
|  | 0.0156 | 0 | 60 | 0 | 50 | — | 0 |
|  | 0.0040 | 0 | 20 | 0 | 20 | — | 0 |
| 37 | 1.0000 | 70 | 100 | 100 | 100 | — | 70 |
|  | 0.2500 | 20 | 100 | 100 | 100 | — | 50 |
|  | 0.0625 | 0 | 100 | 50 | 90 | — | 30 |
|  | 0.0156 | 0 | 80 | 40 | 80 | — | 30 |
|  | 0.0040 | 0 | 50 | 20 | 40 | — | 0 |
| 38 | 1.0000 | 20 | 100 | 70 | 100 | — | 30 |
|  | 0.2500 | 10 | 100 | 60 | 100 | — | 30 |
|  | 0.0625 | 0 | 80 | 30 | 80 | — | 0 |
|  | 0.0156 | 0 | 20 | 0 | 40 | — | 0 |
|  | 0.0040 | 0 | 0 | 0 | 0 | — | 0 |
| 39 | 1.0000 | 10 | 100 | 70 | 100 | — | 10 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.2506 | 0 | 100 | 10 | 100 | — | |
| | 0.0625 | 0 | 80 | 0 | 70 | — | 0 |
| | 0.0156 | 0 | 50 | 0 | 50 | — | 0 |
| | 0.0040 | 0 | 50 | 0 | 20 | — | 0 |
| 40 | 1.0000 | 0 | 80 | 30 | 100 | — | 10 |
| | 0.2500 | 0 | 70 | 30 | 100 | — | 0 |
| | 0.0625 | 0 | 30 | 0 | 30 | — | 0 |
| | 0.0156 | 0 | 0 | 0 | 30 | — | 0 |
| | 0.0040 | 0 | 0 | 0 | 0 | — | 0 |
| 42 | 1.0000 | 0 | 100 | 30 | 100 | 30 | 20 |
| | 0.2500 | 0 | 100 | 30 | 100 | 30 | 20 |
| | 0.0625 | 0 | 80 | 0 | 80 | 0 | 0 |
| | 0.0156 | 0 | 80 | 0 | 50 | 0 | 0 |
| | 0.0040 | 0 | 10 | 0 | 0 | 0 | 0 |
| 43 | 1.0000 | 0 | 100 | 0 | 90 | 100 | 0 |
| | 0.2500 | 0 | 100 | 0 | 80 | 30 | 0 |
| | 0.0625 | 0 | 95 | 0 | 40 | 10 | 0 |
| | 0.0156 | 0 | 70 | 0 | 20 | 0 | 0 |
| | 0.0040 | 0 | 0 | 0 | 0 | 0 | 0 |
| 44 | 4.0000 | 70 | 100 | 90 | 100 | 100 | 100 |
| | 1.0000 | 60 | 100 | 50 | 100 | 100 | 100 |
| | 0.2500 | 40 | 100 | 30 | 100 | 100 | 100 |
| | 0.0625 | 20 | 100 | 0 | 70 | 80 | 50 |
| | 0.0156 | 0 | 100 | 0 | 60 | 30 | 0 |
| 45 | 4.0000 | 50 | 100 | 70 | 100 | 100 | 100 |
| | 1.0000 | 40 | 100 | 40 | 100 | 100 | 100 |
| | 0.2500 | 30 | 100 | 0 | 90 | 100 | 100 |
| | 0.0625 | 20 | 100 | 0 | 60 | 50 | 30 |
| | 0.0156 | 0 | 100 | 0 | 60 | 0 | 0 |
| 46 | 4.0000 | 60 | 100 | 60 | 100 | 90 | 0 |
| | 1.0000 | 20 | 100 | 50 | 100 | 0 | 0 |
| | 0.2500 | 0 | 100 | 50 | 90 | 0 | 0 |
| | 0.0625 | 0 | 95 | 30 | 70 | 0 | 0 |
| | 0.0156 | 0 | 90 | 0 | 70 | 0 | 0 |
| 47 | 1.0000 | 10 | 100 | 30 | 90 | 90 | 50 |
| | 0.2500 | 0 | 95 | 10 | 70 | 90 | 30 |
| | 0.0625 | 0 | 80 | 0 | 30 | 0 | 0 |
| | 0.0156 | 0 | 0 | 0 | 0 | 0 | 0 |
| | 0.0040 | 0 | 0 | 0 | 0 | 0 | 0 |
| 48 | 4.0000 | 40 | 100 | 50 | 100 | 100 | 80 |
| | 1.0000 | 30 | 100 | 40 | 90 | 60 | 0 |
| | 0.2500 | 0 | 100 | 0 | 90 | 0 | 0 |
| | 0.0625 | 0 | 100 | 0 | 50 | 0 | 0 |
| | 0.0156 | 0 | 30 | 0 | 20 | 0 | 0 |
| 49 | 4.0000 | 90 | 100 | 100 | 100 | 0 | 50 |
| | 1.0000 | 40 | 100 | 80 | 100 | 0 | 30 |
| | 0.2500 | 0 | 100 | 70 | 100 | 0 | 0 |
| | 0.0625 | 0 | 100 | 40 | 100 | 0 | 0 |
| | 0.0156 | 0 | 95 | 20 | 50 | 0 | 0 |
| 50 | 1.0000 | 30 | 100 | 70 | 100 | 100 | 20 |
| | 0.2500 | 20 | 100 | 10 | 90 | 100 | 0 |
| | 0.0625 | 0 | 100 | 0 | 60 | 0 | 0 |
| | 0.0156 | 0 | 95 | 0 | 20 | 0 | 0 |
| | 0.0040 | 0 | 20 | 0 | 0 | 0 | 0 |
| 51 | 1.0000 | 20 | 100 | 30 | 100 | 100 | 0 |
| | 0.2500 | 0 | 100 | 10 | 50 | 100 | 0 |
| | 0.0625 | 0 | 100 | 0 | 20 | 0 | 0 |
| | 0.0156 | 0 | 20 | 0 | 0 | 0 | 0 |
| | 0.0040 | 0 | 0 | 0 | 0 | 0 | 0 |
| 52 | 4.0000 | 30 | 100 | 100 | 100 | — | 50 |
| | 1.0000 | 20 | 100 | 50 | 100 | — | 0 |
| | 0.2500 | 0 | 100 | 0 | 90 | 40 | 0 |
| | 0.0625 | 0 | 70 | 0 | 50 | 30 | 0 |
| | 0.0156 | 0 | 70 | 0 | 0 | 30 | 0 |
| 53 | 4.0000 | 20 | 100 | 30 | 100 | 100 | 30 |
| | 1.0000 | 10 | 100 | 0 | 90 | 70 | 0 |
| | 0.2500 | 0 | 100 | 0 | 80 | 50 | 0 |
| | 0.0625 | 0 | 100 | 0 | 80 | 0 | 0 |
| | 0.0156 | 0 | 40 | 0 | 30 | 0 | 0 |
| 54 | 4.0000 | 60 | 100 | 100 | 100 | — | 20 |
| | 1.0000 | 0 | 100 | 50 | 100 | — | 0 |
| | 0.2500 | 0 | 100 | 20 | 70 | — | 0 |
| | 0.0625 | 0 | 100 | 0 | 70 | — | 0 |
| | 0.0156 | 0 | 75 | 0 | 0 | — | 0 |
| 55 | 4.0000 | 40 | 100 | 100 | 100 | 100 | 90 |
| | 1.0000 | 10 | 100 | 0 | 100 | 100 | 40 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.2500 | 0 | 100 | 0 | 80 | 20 | 20 |
| | 0.0625 | 0 | 90 | 0 | 50 | 10 | 0 |
| | 0.0156 | 0 | 60 | 0 | 0 | 0 | 0 |
| 56 | 4.0000 | 50 | 100 | 100 | 100 | 100 | 70 |
| | 1.0000 | 10 | 100 | 10 | 100 | 100 | 0 |
| | 0.2500 | 0 | 100 | 10 | 90 | 50 | 0 |
| | 0.0625 | 0 | 100 | 10 | 70 | 0 | 0 |
| | 0.0156 | 0 | 70 | 0 | 20 | 0 | 0 |
| 57 | 4.0000 | 0 | 100 | 0 | 100 | 100 | 0 |
| | 1.0000 | 0 | 100 | 0 | 90 | 40 | 0 |
| | 0.2500 | 0 | 80 | 0 | 50 | 0 | 0 |
| | 0.0625 | 0 | 50 | 0 | 0 | 0 | 0 |
| | 0.0156 | 0 | 0 | 0 | 0 | 0 | 0 |
| 58 | 4.0000 | 0 | 100 | 0 | 80 | 100 | 100 |
| | 1.0000 | 0 | 100 | 0 | 70 | 100 | 100 |
| | 0.2500 | 0 | 95 | 0 | 20 | 0 | 0 |
| | 0.0625 | 0 | 60 | 0 | 0 | 0 | 0 |
| | 0.0156 | 0 | 0 | 0 | 0 | 0 | 0 |
| 59 | 1.0000 | 0 | 100 | 20 | 40 | 100 | 10 |
| | 0.2500 | 0 | 100 | 0 | 10 | 50 | 0 |
| | 0.0625 | 0 | 10 | 0 | 0 | 0 | 0 |
| | 0.0156 | 0 | 0 | 0 | 0 | 0 | 0 |
| | 0.0040 | 0 | 0 | 0 | 0 | 0 | 0 |
| 60 | 4.0000 | 40 | 100 | 0 | 100 | 50 | 60 |
| | 1.0000 | 10 | 100 | 0 | 100 | 50 | 20 |
| | 0.2500 | 0 | 100 | 0 | 70 | 30 | 0 |
| | 0.0625 | 0 | 90 | 0 | 30 | 0 | 0 |
| | 0.0156 | 0 | 80 | 0 | 0 | 0 | 0 |
| 61 | 4.0000 | 20 | 100 | 40 | 100 | 0 | 0 |
| | 1.0000 | 0 | 100 | 0 | 100 | 0 | 0 |
| | 0.2500 | 0 | 100 | 0 | 80 | 0 | 0 |
| | 0.0625 | 0 | 100 | 0 | 40 | 0 | 0 |
| | 0.0156 | 0 | 0 | 0 | 0 | 0 | 0 |
| 62 | 4.0000 | 30 | 100 | 100 | 100 | 100 | 80 |
| | 1.0000 | 10 | 100 | 0 | 90 | 60 | 0 |
| | 0.2500 | 0 | 100 | 0 | 70 | 30 | 0 |
| | 0.0625 | 0 | 80 | 0 | 10 | 0 | 0 |
| | 0.0156 | 0 | 60 | 0 | 0 | 0 | 0 |
| 63 | 4.0000 | 20 | 100 | 0 | 100 | 100 | 0 |
| | 1.0000 | 0 | 100 | 0 | 100 | 80 | 0 |
| | 0.2500 | 0 | 100 | 0 | 80 | 40 | 0 |
| | 0.0625 | 0 | 100 | 0 | 50 | 0 | 0 |
| | 0.0156 | 0 | 20 | 0 | 0 | 0 | 0 |
| 64 | 4.0000 | 50 | 100 | 0 | 100 | 100 | 30 |
| | 1.0000 | 20 | 100 | 0 | 100 | 100 | 0 |
| | 0.2500 | 0 | 100 | 0 | 70 | 100 | 0 |
| | 0.0625 | 0 | 70 | 0 | 50 | 0 | 0 |
| | 0.0156 | 0 | 30 | 0 | 30 | 0 | 0 |
| 65 | 4.0000 | 10 | 100 | 30 | 100 | 0 | 30 |
| | 1.0000 | 0 | 100 | 10 | 80 | 0 | 0 |
| | 0.2500 | 0 | 100 | 0 | 50 | 0 | 0 |
| | 0.0625 | 0 | 60 | 0 | 10 | 0 | 0 |
| | 0.0156 | 0 | 50 | 0 | 0 | 0 | 0 |
| 66 | 4.0000 | 0 | 100 | 30 | 100 | 40 | 0 |
| | 1.0000 | 0 | 100 | 20 | 90 | 40 | 0 |
| | 0.2500 | 0 | 100 | 0 | 70 | 0 | 0 |
| | 0.0625 | 0 | 95 | 0 | 40 | 0 | 0 |
| | 0.0156 | 0 | 0 | 0 | 0 | 0 | 0 |
| 67 | 4.0000 | 10 | 100 | 40 | 100 | 30 | 70 |
| | 1.0000 | 0 | 100 | 0 | 100 | 20 | 0 |
| | 0.2500 | 0 | 100 | 0 | 70 | 0 | 0 |
| | 0.0625 | 0 | 60 | 0 | 0 | 0 | 0 |
| | 0.0156 | 0 | 50 | 0 | 0 | 0 | 0 |
| 68 | 4.0000 | 0 | 100 | 40 | 100 | 80 | 20 |
| | 1.0000 | 0 | 100 | 20 | 90 | 0 | 0 |
| | 0.2500 | 0 | 100 | 0 | 70 | 0 | 0 |
| | 0.0625 | 0 | 60 | 0 | 30 | 0 | 0 |
| | 0.0156 | 0 | 20 | 0 | 0 | 0 | 0 |
| 69 | 4.0000 | 50 | 100 | 0 | 100 | 100 | 30 |
| | 1.0000 | 10 | 100 | 0 | 100 | 20 | 20 |
| | 0.2500 | 0 | 100 | 0 | 100 | 0 | 0 |
| | 0.0625 | 0 | 90 | 0 | 0 | 0 | 0 |
| | 0.0156 | 0 | 90 | 0 | 0 | 0 | 0 |
| 70 | 1.0000 | 20 | 100 | 100 | 100 | 100 | 100 |
| | 0.2500 | 10 | 100 | 20 | 70 | 100 | 0 |
| | 0.0625 | 0 | 70 | 0 | 10 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0156 | 0 | 20 | 0 | 0 | 0 | 0 |
| | 0.0040 | 0 | 0 | 0 | 0 | 0 | 0 |
| 71 | 4.0000 | 20 | 100 | 50 | 100 | 100 | 50 |
| | 1.0000 | 0 | 100 | 20 | 90 | 100 | 20 |
| | 0.2500 | 0 | 100 | 0 | 80 | 50 | 0 |
| | 0.0625 | 0 | 100 | 0 | 50 | 0 | 0 |
| | 0.0156 | 0 | 40 | 0 | 0 | 0 | 0 |
| 72 | 1.0000 | 0 | 100 | 30 | 60 | 0 | 70 |
| | 0.2500 | 0 | 95 | 0 | 50 | 0 | 20 |
| | 0.0625 | 0 | 70 | 0 | 0 | 0 | 0 |
| | 0.0156 | 0 | 0 | 0 | 0 | 0 | 0 |
| | 0.0040 | 0 | 0 | 0 | 0 | 0 | 0 |
| 73 | 1.0000 | 0 | 100 | 30 | 90 | 50 | 20 |
| | 0.2500 | 0 | 100 | 0 | 60 | 30 | 10 |
| | 0.0625 | 0 | 70 | 0 | 10 | 0 | 0 |
| | 0.0156 | 0 | 40 | 0 | 0 | 0 | 0 |
| | 0.0040 | 0 | 0 | 0 | 0 | 0 | 0 |
| 74 | 1.0000 | 20 | 100 | 0 | 100 | 100 | 70 |
| | 0.2500 | 0 | 100 | 0 | 40 | 50 | 40 |
| | 0.0625 | 0 | 95 | 0 | 20 | 0 | 0 |
| | 0.0156 | 0 | 60 | 0 | 0 | 0 | 0 |
| | 0.0040 | 0 | 0 | 0 | 0 | 0 | 0 |
| 75 | 1.0000 | 0 | 100 | 50 | 90 | 50 | 0 |
| | 0.2500 | 0 | 100 | 30 | 80 | 20 | 0 |
| | 0.0625 | 0 | 85 | 0 | 40 | 0 | 0 |
| | 0.0156 | 0 | 30 | 0 | 0 | 0 | 0 |
| | 0.0040 | 0 | 0 | 0 | 0 | 0 | 0 |
| 76 | 1.0000 | 0 | 100 | 20 | 90 | 100 | 0 |
| | 0.2500 | 0 | 100 | 0 | 70 | 0 | 0 |
| | 0.0625 | 0 | 95 | 0 | 40 | 0 | 0 |
| | 0.0156 | 0 | 70 | 0 | 0 | 0 | 0 |
| | 0.0040 | 0 | 0 | 0 | 0 | 0 | 0 |
| 77 | 4.0000 | 80 | 100 | 30 | 100 | 0 | 20 |
| | 1.0000 | 20 | 100 | 30 | 100 | 0 | 10 |
| | 0.2500 | 0 | 100 | 0 | 80 | 0 | 0 |
| | 0.0625 | 0 | 95 | 0 | 70 | 0 | 0 |
| | 0.0156 | 0 | 95 | 0 | 40 | 0 | 0 |
| 78 | 1.0000 | 10 | 100 | 100 | 100 | 100 | 60 |
| | 0.2500 | 0 | 100 | 30 | 80 | 20 | 0 |
| | 0.0625 | 0 | 100 | 0 | 70 | 20 | 0 |
| | 0.0156 | 0 | 80 | 0 | 20 | 0 | 0 |
| | 0.0040 | 0 | 0 | 0 | 0 | 0 | 0 |
| 79 | 1.0000 | 20 | 100 | 10 | 100 | 50 | 0 |
| | 0.2500 | 10 | 95 | 0 | 30 | 0 | 0 |
| | 0.0625 | 0 | 85 | 0 | 30 | 0 | 0 |
| | 0.0156 | 0 | 10 | 0 | 0 | 0 | 0 |
| | 0.0040 | 0 | 0 | 0 | 0 | 0 | 0 |
| 80 | 1.0000 | 20 | 100 | 0 | 100 | 100 | 0 |
| | 0.2500 | 0 | 100 | 0 | 0 | 40 | 0 |
| | 0.0625 | 0 | 100 | 0 | 0 | 0 | 0 |
| | 0.0156 | 0 | 10 | 0 | 0 | 0 | 0 |
| | 0.0040 | 0 | 0 | 0 | 0 | 0 | 0 |
| 81 | 1.0000 | 30 | 100 | 30 | 100 | 70 | 0 |
| | 0.2500 | 0 | 90 | 30 | 80 | 0 | 0 |
| | 0.0625 | 0 | 85 | 20 | 60 | 0 | 0 |
| | 0.0156 | 0 | 0 | 0 | 40 | 0 | 0 |
| | 0.0040 | 0 | 0 | 0 | 20 | 0 | 0 |
| 82 | 1.0000 | 0 | 100 | 20 | 50 | 0 | 0 |
| | 0.2500 | 0 | 100 | 0 | 50 | 0 | 0 |
| | 0.0625 | 0 | 40 | 0 | 0 | 0 | 0 |
| | 0.0156 | 0 | 40 | 0 | 0 | 0 | 0 |
| | 0.0040 | 0 | 0 | 0 | 0 | 0 | 0 |
| 83 | 1.0000 | 0 | 100 | 0 | 30 | 0 | 0 |
| | 0.2500 | 0 | 70 | 0 | 0 | 0 | 0 |
| | 0.0625 | 0 | 20 | 0 | 0 | 0 | 0 |
| | 0.0156 | 0 | 20 | 0 | 0 | 0 | 0 |
| | 0.0040 | 0 | 0 | 0 | 0 | 0 | 0 |
| 86 | 1.0000 | 0 | 100 | 0 | 0 | 0 | 0 |
| | 0.2500 | 0 | 20 | 0 | 0 | 0 | 0 |
| | 0.0625 | 0 | 0 | 0 | 0 | 0 | 0 |
| | 0.0156 | 0 | 0 | 0 | 0 | 0 | 0 |
| | 0.0040 | 0 | 0 | 0 | 0 | 0 | 0 |
| 87 | 1.0000 | 10 | 100 | 0 | 0 | 0 | 0 |
| | 0.2500 | 0 | 80 | 0 | 0 | 0 | 0 |
| | 0.0625 | 0 | 20 | 0 | 0 | 0 | 0 |
| | 0.0156 | 0 | 0 | 0 | 0 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
|  | 0.0040 | 0 | 0 | 0 | 0 | 0 | 0 |
| 88 | 1.0000 | 10 | 100 | 0 | 70 | 80 | 0 |
|  | 0.2500 | 0 | 100 | 0 | 0 | 0 | 0 |
|  | 0.0625 | 0 | 50 | 0 | 0 | 0 | 0 |
|  | 0.0156 | 0 | 0 | 0 | 0 | 0 | 0 |
|  | 0.0040 | 0 | 00 | 0 | 0 | 0 | 0 |
| 89 | 4.0000 | 10 | 100 | 10 | 90 | 0 | 0 |
|  | 1.0000 | 0 | 100 | 0 | 50 | 0 | 0 |
|  | 0.2500 | 0 | 100 | 0 | 50 | 0 | 0 |
|  | 0.0625 | 0 | 60 | 0 | 0 | 0 | 0 |
|  | 0.0156 | 0 | 0 | 0 | 0 | 0 | 0 |
| 90 | 1.0000 | 0 | 100 | 0 | 0 | 0 | 0 |
|  | 0.2500 | 0 | 20 | 0 | 0 | 0 | 0 |
|  | 0.0625 | 0 | 0 | 0 | 0 | 0 | 0 |
|  | 0.0156 | 0 | 0 | 0 | 0 | 0 | 0 |
|  | 0.0040 | 0 | 0 | 0 | 0 | 0 | 0 |
| 91 | 1.0000 | 20 | 90 | 0 | 0 | 0 | 0 |
|  | 0.2500 | 0 | 40 | 0 | 0 | 0 | 0 |
|  | 0.0625 | 0 | 10 | 0 | 0 | 0 | 0 |
|  | 0.0156 | 0 | 10 | 0 | 0 | 0 | 0 |
|  | 0.0040 | 0 | 0 | 0 | 0 | 0 | 0 |
| 93 | 1.0000 | 20 | 100 | 0 | 100 | 0 | 0 |
|  | 0.2500 | 10 | 100 | 0 | 80 | 0 | 0 |
|  | 0.0625 | 0 | 100 | 0 | 80 | 0 | 0 |
|  | 0.0156 | 0 | 80 | 0 | 20 | 0 | 0 |
|  | 0.0040 | 0 | 10 | 0 | 0 | 0 | 0 |
| 94 | 1.0000 | 20 | 100 | 0 | 100 | 0 | 40 |
|  | 0.2500 | 0 | 100 | 0 | 50 | 0 | 0 |
|  | 0.0625 | 0 | 80 | 0 | 0 | 0 | 0 |
|  | 0.0156 | 0 | 0 | 0 | 0 | 0 | 0 |
|  | 0.0040 | 0 | 0 | 0 | 0 | 0 | 0 |
| 95 | 1.0000 | 10 | 100 | 0 | 90 | 40 | 0 |
|  | 0.2500 | 0 | 100 | 0 | 70 | 30 | 0 |
|  | 0.0625 | 0 | 100 | 0 | 50 | 0 | 0 |
|  | 0.0156 | 0 | 0 | 0 | 30 | 0 | 0 |
|  | 0.0040 | 0 | 0 | 0 | 0 | 0 | 0 |
| 96 | 1.0000 | 0 | 100 | 10 | 100 | 50 | 20 |
|  | 0.2500 | 0 | 95 | 0 | 50 | 0 | 0 |
|  | 0.0625 | 0 | 30 | 0 | 40 | 0 | 0 |
|  | 0.0156 | 0 | 0 | 0 | 0 | 0 | 0 |
|  | 0.0040 | 0 | 0 | 0 | 0 | 0 | 0 |
| 97 | 1.0000 | 30 | 100 | 20 | 80 | 0 | 20 |
|  | 0.2500 | 20 | 100 | 0 | 30 | 0 | 0 |
|  | 0.0250 | 10 | 90 | 0 | 30 | 0 | 0 |
|  | 0.0156 | 0 | 80 | 0 | 30 | 0 | 0 |
|  | 0.0040 | 0 | 0 | 0 | 0 | 0 | 0 |
| 99 | 1.0000 | 0 | 100 | 0 | 90 | 0 | 0 |
|  | 0.2500 | 0 | 100 | 0 | 70 | 0 | 0 |
|  | 0.0625 | 0 | 85 | 0 | 50 | 0 | 0 |
|  | 0.0156 | 0 | 10 | 0 | 30 | 0 | 0 |
|  | 0.0040 | 0 | 0 | 0 | 0 | 0 | 0 |
| 100 | 1.0000 | 20 | 100 | 70 | 100 | 100 | 10 |
|  | 0.2500 | 10 | 100 | 0 | 40 | 90 | 0 |
|  | 0.0625 | 10 | 100 | 0 | 0 | 0 | 0 |
|  | 0.0156 | 10 | 80 | 0 | 0 | 0 | 0 |
|  | 0.0040 | 0 | 10 | 0 | 0 | 0 | 0 |
| 101 | 1.0000 | 20 | 100 | 0 | 90 | 100 | 20 |
|  | 0.2500 | 0 | 100 | 0 | 80 | 90 | 0 |
|  | 0.0625 | 0 | 95 | 0 | 20 | 0 | 0 |
|  | 0.0156 | 0 | 30 | 0 | 0 | 0 | 0 |
|  | 0.0040 | 0 | 0 | 0 | 0 | 0 | 0 |
| 102 | 1.0000 | 10 | 100 | 30 | 90 | 30 | 0 |
|  | 0.2500 | 0 | 100 | 10 | 60 | 0 | 0 |
|  | 0.0625 | 0 | 80 | 0 | 0 | 0 | 0 |
|  | 0.0156 | 0 | 70 | 0 | 0 | 0 | 0 |
|  | 0.0040 | 0 | 0 | 0 | 0 | 0 | 0 |
| 103 | 1.0000 | 0 | 100 | 10 | 70 | 0 | 10 |
|  | 0.2500 | 0 | 80 | 0 | 40 | 0 | 0 |
|  | 0.0625 | 0 | 10 | 0 | 0 | 0 | 0 |
|  | 0.0156 | 0 | 0 | 0 | 0 | 0 | 0 |
|  | 0.0040 | 0 | 0 | 0 | 0 | 0 | 0 |
| 100 | 4.0000 | 0 | 100 | 0 | 100 | 30 | 0 |
|  | 1.0000 | 0 | 100 | 0 | 100 | 0 | 0 |
|  | 0.2500 | 0 | 100 | 0 | 80 | 0 | 0 |
|  | 0.0625 | 0 | 90 | 0 | 0 | 0 | 0 |
|  | 0.0156 | 0 | 50 | 0 | 0 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| 107 | 4.0000 | 20 | 100 | 30 | 90 | 100 | 0 |
|  | 1.0000 | 0 | 100 | 30 | 80 | 30 | 0 |
|  | 0.2500 | 0 | 100 | 0 | 70 | 0 | 0 |
|  | 0.0625 | 0 | 80 | 0 | 50 | 0 | 0 |
|  | 0.0156 | 0 | 30 | 0 | 20 | 0 | 0 |
| 108 | 1.0000 | 0 | 100 | 30 | 90 | 80 | 0 |
|  | 0.2500 | 0 | 100 | 0 | 90 | 50 | 0 |
|  | 0.0625 | 0 | 95 | 0 | 70 | 0 | 0 |
|  | 0.1560 | 0 | 75 | 0 | 50 | 0 | 0 |
|  | 0.0040 | 0 | 0 | 0 | 0 | 0 | 0 |
| 109 | 4.0000 | 20 | 100 | 0 | 100 | 0 | 0 |
|  | 1.0000 | 0 | 100 | 0 | 100 | 0 | 0 |
|  | 0.2500 | 0 | 95 | 0 | 30 | 0 | 0 |
|  | 0.0625 | 0 | 90 | 0 | 20 | 0 | 0 |
|  | 0.0156 | 0 | 20 | 0 | 0 | 0 | 0 |
| 112 | 1.0000 | 0 | 100 | 50 | 100 | 100 | 0 |
|  | 0.2500 | 0 | 100 | 10 | 70 | 80 | 0 |
|  | 0.0625 | 0 | 100 | 0 | 40 | 40 | 0 |
|  | 0.0156 | 0 | 70 | 0 | 0 | 0 | 0 |
|  | 0.0040 | 0 | 0 | 0 | 0 | 0 | 0 |
| 113 | 1.0000 | 0 | 100 | 50 | 90 | 0 | 10 |
|  | 0.2500 | 0 | 70 | 20 | 70 | 0 | 0 |
|  | 0.0625 | 0 | 40 | 0 | 30 | 0 | 0 |
|  | 0.0156 | 0 | 0 | 0 | 0 | 0 | 0 |
|  | 0.0040 | 0 | 0 | 0 | 0 | 0 | 0 |
| 114 | 4.0000 | 30 | 100 | 0 | 100 | 90 | 0 |
|  | 1.0000 | 0 | 100 | 0 | 90 | 0 | 0 |
|  | 0.2500 | 0 | 100 | 0 | 70 | 0 | 0 |
|  | 0.0625 | 0 | 90 | 0 | 40 | 0 | 0 |
|  | 0.0156 | 0 | 20 | 0 | 0 | 0 | 0 |
| 115 | 1.0000 | 0 | 100 | 20 | 90 | 0 | 0 |
|  | 0.2500 | 0 | 95 | 0 | 60 | 0 | 0 |
|  | 0.0625 | 0 | 60 | 0 | 0 | 0 | 0 |
|  | 0.0156 | 0 | 0 | 0 | 0 | 0 | 0 |
|  | 0.0040 | 0 | 0 | 0 | 0 | 0 | 0 |
| 116 | 1.0000 | 0 | 100 | 60 | 100 | 30 | 20 |
|  | 0.2500 | 0 | 100 | 10 | 60 | 0 | 0 |
|  | 0.0625 | 0 | 85 | 0 | 40 | 0 | 0 |
|  | 0.0156 | 0 | 30 | 0 | 0 | 0 | 0 |
|  | 0.0040 | 0 | 0 | 0 | 0 | 0 | 0 |
| 117 | 1.0000 | 0 | 100 | 10 | 100 | 0 | 0 |
|  | 0.2500 | 0 | 100 | 0 | 90 | 0 | 0 |
|  | 0.0625 | 0 | 50 | 0 | 0 | 0 | 0 |
|  | 0.0156 | 0 | 30 | 0 | 0 | 0 | 0 |
|  | 0.0040 | 0 | 0 | 0 | 0 | 0 | 0 |
| 118 | 4.0000 | 0 | 100 | 0 | 80 | 100 | 0 |
|  | 1.0000 | 0 | 100 | 0 | 40 | 100 | 0 |
|  | 0.2500 | 0 | 80 | 0 | 10 | 100 | 0 |
|  | 0.0625 | 0 | 50 | 0 | 0 | 40 | 0 |
|  | 0.0156 | 0 | 0 | 0 | 0 | 0 | 0 |
| 120 | 4.0000 | 10 | 100 | 20 | 60 | 0 | 0 |
|  | 1.0000 | 0 | 100 | 0 | 0 | 0 | 0 |
|  | 0.2500 | 0 | 80 | 0 | 0 | 0 | 0 |
|  | 0.0625 | 0 | 60 | 0 | 0 | 0 | 0 |
|  | 0.0156 | 0 | 50 | 0 | 0 | 0 | 0 |
| 122 | 4.0000 | 0 | 100 | 100 | 100 | 100 | 50 |
|  | 1.0000 | 0 | 100 | 40 | 95 | 100 | 30 |
|  | 0.2500 | 0 | 100 | 0 | 90 | 100 | 30 |
|  | 0.0625 | 0 | 95 | 0 | 70 | 100 | 30 |
|  | 0.0156 | 0 | 95 | 0 | 30 | 50 | 30 |
| 123 | 4.0000 | 30 | 100 | 40 | 100 | 100 | 60 |
|  | 1.0000 | 20 | 100 | 0 | 100 | 60 | 0 |
|  | 0.2500 | 0 | 100 | 0 | 100 | 0 | 0 |
|  | 0.0625 | 0 | 100 | 0 | 80 | 0 | 0 |
|  | 0.0156 | 0 | 90 | 0 | 40 | 0 | 0 |
| 124 | 4.0000 | 40 | 100 | 40 | 100 | 50 | 40 |
|  | 1.0000 | 30 | 100 | 40 | 100 | 0 | 0 |
|  | 0.2500 | 30 | 100 | 30 | 100 | 0 | 0 |
|  | 0.0625 | 0 | 80 | 0 | 50 | 0 | 0 |
|  | 0.0156 | 0 | 60 | 0 | 20 | 0 | 0 |
| 125 | 4.0000 | 10 | 100 | 50 | 100 | 100 | 100 |
|  | 1.0000 | 0 | 100 | 40 | 90 | 100 | 100 |
|  | 0.2500 | 0 | 100 | 0 | 80 | 100 | 0 |
|  | 0.0625 | 0 | 60 | 0 | 50 | 0 | 0 |
|  | 0.0156 | 0 | 20 | 0 | 20 | 0 | 0 |
| 126 | 1.0000 | 0 | 100 | 40 | 100 | 0 | 20 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.2500 | 0 | 100 | 20 | 70 | 0 | 10 |
| | 0.0625 | 0 | 95 | 20 | 60 | 0 | 0 |
| | 0.0156 | 0 | 70 | 0 | 30 | 0 | 0 |
| | 0.0040 | 0 | 0 | 0 | 0 | 0 | 0 |
| 127 | 4.0000 | 30 | 100 | 10 | 100 | 0 | 80 |
| | 1.0000 | 0 | 100 | 0 | 90 | 0 | 0 |
| | 0.2500 | 0 | 95 | 0 | 50 | 0 | 0 |
| | 0.0625 | 0 | 95 | 0 | 50 | 0 | 0 |
| | 0.0156 | 0 | 50 | 0 | 0 | 0 | 0 |
| 128 | 4.0000 | 0 | 100 | 50 | 100 | — | — |
| | 1.0000 | 0 | 100 | 20 | 100 | 0 | — |
| | 0.2500 | 0 | 95 | 0 | 70 | 0 | — |
| | 0.0625 | 0 | 95 | 0 | 30 | 0 | — |
| | 0.0156 | 0 | 70 | 0 | 0 | 0 | — |
| 129 | 1.0000 | 0 | 100 | 10 | 30 | 0 | 0 |
| | 0.2500 | 0 | 30 | 0 | 0 | 0 | 0 |
| | 0.0625 | 0 | 0 | 0 | 0 | 0 | 0 |
| | 0.0156 | 0 | 0 | 0 | 0 | 0 | 0 |
| | 0.0040 | 0 | 0 | 0 | 0 | 0 | 0 |
| 138 | 1.0000 | 10 | 100 | 0 | 0 | 0 | 0 |
| | 0.2500 | 0 | 90 | 0 | 0 | 0 | 0 |
| | 0.0625 | 0 | 50 | 0 | 0 | 0 | 0 |
| | 0.0156 | 0 | 0 | 0 | 0 | 0 | 0 |
| | 0.0040 | 0 | 0 | 0 | 0 | 0 | 0 |
| 142 | 4.0000 | 0 | 100 | 0 | 100 | 30 | 80 |
| | 1.0000 | 0 | 100 | 0 | 90 | 30 | 30 |
| | 0.2500 | 0 | 90 | 0 | 40 | 20 | 0 |
| | 0.0625 | 0 | 70 | 0 | 20 | 0 | 0 |
| | 0.0156 | 0 | 50 | 0 | 0 | 0 | 0 |
| 143 | 4.0000 | 0 | 100 | 0 | 100 | 60 | 60 |
| | 1.0000 | 0 | 100 | 0 | 90 | 0 | 30 |
| | 0.2500 | 0 | 100 | 0 | 70 | 0 | 30 |
| | 0.0625 | 0 | 100 | 0 | 50 | 0 | 20 |
| | 0.0156 | 0 | 0 | 0 | 40 | 0 | 0 |
| 144 | 4.0000 | 30 | 100 | 0 | 100 | 0 | 0 |
| | 1.0000 | 0 | 100 | 0 | 100 | 0 | 0 |
| | 0.2500 | 0 | 100 | 0 | 30 | 0 | 0 |
| | 0.0625 | 0 | 95 | 0 | 0 | 0 | 0 |
| | 0.0156 | 0 | 30 | 0 | 0 | 0 | 0 |
| 145 | 1.0000 | 0 | 90 | 0 | 70 | 50 | 20 |
| | 0.2500 | 0 | 80 | 0 | 40 | 0 | 0 |
| | 0.0625 | 0 | 30 | 0 | 0 | 0 | 0 |
| | 0.0156 | 0 | 0 | 0 | 0 | 0 | 0 |
| | 0.0040 | 0 | 0 | 0 | 0 | 0 | 0 |
| 146 | 1.0000 | 0 | 100 | 0 | 70 | 40 | 0 |
| | 0.2500 | 0 | 100 | 0 | 0 | 0 | 0 |
| | 0.0625 | 0 | 30 | 0 | 0 | 0 | 0 |
| | 0.0156 | 0 | 30 | 0 | 0 | 0 | 0 |
| | 0.0040 | 0 | 0 | 0 | 0 | 0 | 0 |
| 147 | 1.0000 | 0 | 100 | 0 | 0 | 20 | 30 |
| | 0.2500 | 0 | 30 | 0 | 0 | 0 | 0 |
| | 0.0625 | 0 | 20 | 0 | 0 | 0 | 0 |
| | 0.0156 | 0 | 0 | 0 | 0 | 0 | 0 |
| | 0.0040 | 0 | 0 | 0 | 0 | 0 | 0 |
| 148 | 1.0000 | 0 | 100 | 0 | 10 | 0 | 20 |
| | 0.2500 | 0 | 50 | 0 | 0 | 0 | 0 |
| | 0.0625 | 0 | 0 | 0 | 0 | 0 | 0 |
| | 0.0156 | 0 | 0 | 0 | 0 | 0 | 0 |
| | 0.0040 | 0 | 0 | 0 | 0 | 0 | 0 |
| 151 | 1.0000 | 0 | 100 | 30 | 0 | 30 | 0 |
| | 0.2500 | 0 | 95 | 0 | 0 | 0 | 0 |
| | 0.0625 | 0 | 20 | 0 | 0 | 0 | 0 |
| | 0.0156 | 0 | 20 | 0 | 0 | 0 | 0 |
| | 0.0040 | 0 | 20 | 0 | 0 | 0 | 0 |
| 152 | 1.0000 | 0 | 100 | 0 | 70 | 0 | 0 |
| | 0.2500 | 0 | 100 | 0 | 70 | 0 | 0 |
| | 0.0625 | 0 | 50 | 0 | 0 | 0 | 0 |
| | 0.0156 | 0 | 0 | 0 | 0 | 0 | 0 |
| | 0.0040 | 0 | 0 | 0 | 0 | 0 | 0 |
| 153 | 1.0000 | 0 | 100 | 0 | 30 | 20 | 10 |
| | 0.2500 | 0 | 70 | 0 | 0 | 0 | 0 |
| | 0.0625 | 0 | 0 | 0 | 0 | 0 | 0 |
| | 0.0156 | 0 | 0 | 0 | 0 | 0 | 0 |
| | 0.0040 | 0 | 0 | 0 | 0 | 0 | 0 |
| 156 | 1.0000 | 0 | 100 | 0 | 60 | 0 | 0 |
| | 0.2500 | 0 | 70 | 0 | 30 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0625 | 0 | 50 | 0 | 0 | 0 | 0 |
| | 0.0156 | 0 | 0 | 0 | 0 | 0 | 0 |
| | 0.0040 | 0 | 0 | 0 | 0 | 0 | 0 |
| 162 | 4.0000 | 80 | 100 | 100 | 100 | 100 | |
| | 1.0000 | 20 | 100 | 100 | 100 | 100 | |
| | 0.2500 | 0 | 100 | 100 | 100 | 100 | |
| | 0.0625 | 0 | 100 | 100 | 80 | 0 | |
| | 0.0157 | | | | | | |
| 163 | 4.0000 | 60 | 100 | 70 | 100 | | |
| | 1.0000 | 40 | 100 | 100 | 100 | | |
| | 0.2500 | 40 | 100 | 100 | 100 | | |
| | 0.0625 | 10 | 100 | 0 | 70 | | |
| | 0.0157 | 0 | 95 | 0 | 0 | | |
| 164 | 4.0000 | 60 | 100 | 100 | 100 | | |
| | 1.0000 | 50 | 100 | 30 | 100 | | |
| | 0.2500 | 20 | 100 | 0 | 100 | | |
| | 0.0625 | 10 | 100 | 0 | 50 | | |
| | 0.0157 | 10 | 70 | 0 | 20 | | |
| 165 | 4.0000 | 100 | 100 | 100 | 100 | | |
| | 1.0000 | 60 | 100 | 90 | 100 | | |
| | 0.2500 | 40 | 100 | 50 | 100 | | |
| | 0.0625 | 20 | 100 | 50 | 100 | | |
| | 0.0157 | 0 | 100 | 0 | 30 | | |
| 166 | 4.0000 | 40 | 100 | 20 | 100 | | |
| | 1.0000 | 30 | 100 | 0 | 100 | | |
| | 0.2500 | 20 | 100 | 0 | 70 | | |
| | 0.0625 | 0 | 80 | 0 | 50 | | |
| | 0.0157 | 0 | 80 | 0 | 0 | | |
| 167 | 4.0000 | 50 | 100 | 100 | 100 | | |
| | 1.0000 | 50 | 100 | 0 | 100 | | |
| | 0.2500 | 40 | 100 | 0 | 100 | | |
| | 0.0625 | 30 | 100 | 0 | 80 | | |
| | 0.0157 | 20 | 100 | 0 | 60 | | |
| 168 | 4.0000 | 60 | 100 | 100 | 100 | 100 | 30 |
| | 1.0000 | 20 | 100 | 100 | 100 | 100 | 30 |
| | 0.2500 | 0 | 100 | 90 | 90 | 70 | 0 |
| | 0.0625 | 0 | 90 | 80 | 90 | 20 | 0 |
| | 0.0157 | 0 | 70 | 0 | 50 | 0 | 0 |
| 169 | 4.0000 | 40 | 100 | 100 | 100 | 100 | |
| | 1.0000 | 0 | 100 | 90 | 95 | 100 | |
| | 0.2500 | 0 | 100 | 0 | 90 | 100 | |
| | 0.0625 | 0 | 99 | 0 | 50 | 100 | |
| | 0.0157 | 0 | 80 | 0 | 30 | 100 | |
| 170 | 4.0000 | 10 | 100 | 0 | 100 | 100 | |
| | 1.0000 | 0 | 100 | 0 | 90 | 100 | |
| | 0.2500 | 0 | 100 | 0 | 90 | 70 | |
| | 0.0625 | 0 | 100 | 0 | 60 | 0 | |
| | 0.0157 | 0 | 60 | 0 | 0 | 0 | |
| 171 | 4.0000 | 10 | 100 | 100 | 100 | 100 | |
| | 1.0000 | 0 | 100 | 100 | 100 | 100 | |
| | 0.2500 | 0 | 100 | 70 | 70 | 40 | |
| | 0.0625 | 0 | 100 | 50 | 30 | 0 | |
| | 0.0157 | 0 | 75 | 0 | 0 | 0 | |
| 172 | 4.0000 | 50 | 100 | 100 | 100 | 100 | 50 |
| | 1.0000 | 20 | 100 | 60 | 100 | 100 | 30 |
| | 0.2500 | 10 | 100 | 40 | 90 | 50 | 20 |
| | 0.0625 | 0 | 100 | 30 | 80 | 50 | 0 |
| | 0.0157 | 0 | 100 | 30 | 60 | 0 | 0 |
| 173 | 4.0000 | 30 | 100 | 70 | 100 | 100 | |
| | 1.0000 | 0 | 100 | 0 | 100 | 100 | |
| | 0.2500 | 0 | 100 | 0 | 70 | 0 | |
| | 0.0625 | 0 | 100 | 0 | 60 | 0 | |
| | 0.0157 | 0 | 40 | 0 | 0 | 0 | |
| 174 | 4.0000 | 0 | 100 | 10 | 100 | 100 | |
| | 1.0000 | 0 | 100 | 0 | 100 | 100 | |
| | 0.2500 | 0 | 100 | 0 | 70 | 100 | |
| | 0.0625 | 0 | 0 | 0 | 20 | 0 | |
| | 0.0157 | 0 | 0 | 0 | 0 | 0 | |
| 175 | 4.0000 | 40 | 90 | 10 | 100 | 100 | 20 |
| | 1.0000 | 30 | 90 | 0 | 70 | 0 | 10 |
| | 0.2500 | 30 | 50 | 0 | 20 | 0 | 0 |
| | 0.0625 | 10 | 10 | 0 | 0 | 0 | 0 |
| | 0.0157 | 10 | 0 | 0 | 0 | 0 | 0 |
| 176 | 4.0000 | 50 | 100 | 30 | 100 | | |
| | 1.0000 | 30 | 100 | 0 | 100 | | |
| | 0.2500 | 20 | 100 | 0 | 100 | | |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0625 | 20 | 100 | 0 | 60 | | |
| | 0.0157 | 0 | 100 | 0 | 30 | | |
| 177 | 4.0000 | 30 | 100 | 80 | 100 | 100 | |
| | 1.0000 | 10 | 100 | 80 | 100 | 100 | |
| | 0.2500 | 10 | 100 | 60 | 100 | 100 | |
| | 0.0625 | 0 | 100 | 30 | 70 | 0 | |
| | 0.0157 | 0 | 60 | 30 | 0 | 0 | |
| 178 | 4.0000 | 30 | 100 | 50 | 100 | 100 | |
| | 1.0000 | 0 | 100 | 50 | 100 | 100 | |
| | 0.2500 | 0 | 100 | 30 | 90 | 100 | |
| | 0.0625 | 0 | 95 | 30 | 0 | 0 | |
| | 0.0157 | 0 | 30 | 0 | 0 | 0 | |
| 179 | 4.0000 | 0 | 100 | 30 | 100 | 100 | |
| | 1.0000 | 0 | 100 | 30 | 80 | 100 | |
| | 0.2500 | 0 | 60 | 0 | 20 | 100 | |
| | 0.0625 | 0 | 10 | 0 | 0 | 0 | |
| | 0.0157 | 0 | 0 | 0 | 0 | 0 | |
| 180 | 4.0000 | 20 | 100 | 30 | 100 | 100 | |
| | 1.0000 | 0 | 100 | 20 | 100 | 100 | |
| | 0.2500 | 0 | 90 | 20 | 50 | 100 | |
| | 0.0625 | 0 | 20 | 0 | 0 | 100 | |
| | 0.0157 | 0 | 0 | 0 | 0 | 0 | |
| 181 | 4.0000 | 10 | 100 | 0 | 100 | 100 | 0 |
| | 1.0000 | 0 | 100 | 0 | 100 | 100 | 0 |
| | 0.2500 | 0 | 98 | 0 | 90 | 90 | 0 |
| | 0.0625 | 0 | 80 | 0 | 80 | 0 | 0 |
| | 0.0157 | 0 | 60 | 0 | 40 | 0 | 0 |
| 183 | 4.0000 | 30 | 100 | 20 | 100 | 70 | |
| | 1.0000 | 0 | 100 | 20 | 100 | | |
| | 0.2500 | 0 | 100 | 10 | 100 | | |
| | 0.0625 | 0 | 30 | 0 | 0 | 0 | |
| | 0.0157 | 0 | 0 | 0 | 0 | 0 | |
| 185 | 4.0000 | 10 | 100 | 10 | 100 | | |
| | 1.0000 | 0 | 100 | 0 | 100 | | |
| | 0.2500 | 0 | 100 | 0 | 100 | | |
| | 0.625 | 0 | 90 | 0 | 0 | | |
| | 0.0157 | 0 | 0 | 0 | 0 | | |
| 186 | 4.0000 | 10 | 100 | 0 | 95 | | |
| | 1.0000 | 0 | 100 | 0 | 30 | | |
| | 0.2500 | 0 | 100 | 0 | 0 | | |
| | 0.0625 | 0 | 100 | 0 | 0 | | |
| | 0.0157 | 0 | 10 | 0 | 0 | | |
| 187 | 4.0000 | 30 | 100 | 20 | 90 | | |
| | 1.0000 | 20 | 100 | 0 | 60 | | |
| | 0.2500 | 10 | 100 | 0 | 0 | | |
| | 0.0625 | 0 | 80 | 0 | 0 | | |
| | 0.0157 | 0 | 0 | 0 | 0 | | |
| 189 | 4.0000 | 80 | 100 | 100 | 100 | | |
| | 1.0000 | 40 | 100 | 100 | 100 | | |
| | 0.2500 | 0 | 100 | 100 | 100 | | |
| | 0.0625 | 0 | 100 | 0 | 100 | | |
| | 0.0157 | 0 | 100 | 0 | 40 | | |
| 190 | 4.0000 | 50 | 100 | 100 | 100 | 100 | |
| | 1.0000 | 20 | 100 | 100 | 100 | 100 | |
| | 0.2500 | 0 | 100 | 60 | 100 | 100 | |
| | 0.0625 | 0 | 100 | 0 | 90 | 100 | |
| | 0.0157 | 0 | 100 | 0 | 90 | 0 | |
| 191 | 4.0000 | 40 | 100 | 70 | 100 | 100 | |
| | 1.0000 | 0 | 100 | 50 | 95 | 100 | |
| | 0.2500 | 0 | 100 | 30 | 80 | 100 | |
| | 0.0625 | 0 | 100 | 0 | 80 | 100 | |
| | 0.0157 | 0 | 85 | 0 | 0 | 0 | |
| 192 | 4.0000 | 10 | 100 | 60 | 100 | 100 | |
| | 1.0000 | 0 | 100 | 50 | 100 | 100 | |
| | 0.2500 | 0 | 100 | 30 | 100 | 0 | |
| | 0.0625 | 0 | 80 | 20 | 20 | 0 | |
| | 0.0157 | 0 | 30 | 0 | 0 | 0 | |
| 193 | 4.0000 | 20 | 100 | 10 | 100 | | |
| | 1.0000 | 20 | 100 | 0 | 100 | | |
| | 0.2500 | 0 | 100 | 0 | 100 | | |
| | 0.0625 | 0 | 95 | 0 | 30 | | |
| | 0.0157 | 0 | 10 | 0 | 0 | | |
| 194 | 4.0000 | 20 | 100 | 0 | 100 | | |
| | 1.0000 | 10 | 100 | 0 | 100 | | |
| | 0.2500 | 10 | 70 | 0 | 20 | | |
| | 0.0625 | 0 | 30 | 0 | 0 | | |

TABLE 8-continued

| Comp. No. | amount (kg/ha) | ORYSA | ECHOR | SCPJU | MOOVA | CYPSE | SAGPY |
|---|---|---|---|---|---|---|---|
|  | 0.0157 | 0 | 0 | 0 | 0 |  |  |
| 195 | 4.0000 | 40 | 100 | 100 | 100 | 100 |  |
|  | 1.0000 | 20 | 100 | 60 | 100 | 100 |  |
|  | 0.2500 | 20 | 100 | 0 | 70 | 100 |  |
|  | 0.625 | 0 | 95 | 0 | 0 | 50 |  |
|  | 0.0157 | 0 | 30 | 0 | 0 | 0 |  |
| 196 | 4.0000 | 40 | 100 | 100 | 100 | 100 |  |
|  | 1.0000 | 30 | 100 | 100 | 100 | 100 |  |
|  | 0.2500 | 20 | 100 | 20 | 100 | 100 |  |
|  | 0.0625 | 0 | 100 | 10 | 40 | 100 |  |
|  | 0.0157 | 0 | 60 | 0 | 20 | 0 |  |
| 197 | 4.0000 | 50 | 100 | 50 | 100 |  |  |
|  | 1.0000 | 30 | 100 | 30 | 100 |  |  |
|  | 0.2500 | 30 | 100 | 20 | 100 |  |  |
|  | 0.0625 | 20 | 100 | 0 | 70 |  |  |
|  | 0.0157 | 0 | 100 | 0 | 50 |  |  |
| 198 | 4.0000 | 0 | 100 | 40 | 100 | 100 |  |
|  | 1.0000 | 0 | 100 | 40 | 100 | 100 |  |
|  | 0.2500 | 0 | 100 | 40 | 100 | 0 |  |
|  | 0.0625 | 0 | 60 | 0 | 10 | 0 |  |
|  | 0.0157 | 0 | 30 | 0 | 0 | 0 |  |
| 199 | 4.0000 | 20 | 100 | 100 | 100 | 100 | 40 |
|  | 1.0000 | 0 | 100 | 50 | 100 | 100 | 0 |
|  | 0.2500 | 0 | 100 | 50 | 100 | 100 | 0 |
|  | 0.0625 | 0 | 95 | 30 | 80 | 20 | 0 |
|  | 0.0157 | 0 | 60 | 30 | 30 | 0 | 0 |
| 200 | 4.0000 | 0 | 100 | 0 | 100 | 100 | 60 |
|  | 1.0000 | 0 | 100 | 0 | 100 | 100 | 0 |
|  | 0.2500 | 0 | 100 | 0 | 90 | 50 | 0 |
|  | 0.0625 | 0 | 70 | 0 | 50 | 0 | 0 |
|  | 0.0157 | 0 | 50 | 0 | 40 | 0 | 0 |
| 201 | 4.0000 | 0 | 100 | 30 | 100 | 100 | 0 |
|  | 1.0000 | 0 | 100 | 0 | 100 | 100 | 0 |
|  | 0.2500 | 0 | 80 | 0 | 80 | 40 | 0 |
|  | 0.0625 | 0 | 70 | 0 | 60 | 40 | 0 |
|  | 0.0157 | 0 | 60 | 0 | 40 | 0 | 0 |
| 202 | 4.0000 | 20 | 100 | 100 | 100 | 100 |  |
|  | 1.0000 | 0 | 100 | 0 | 100 | 100 |  |
|  | 0.2500 | 0 | 80 | 0 | 60 | 100 |  |
|  | 0.0625 | 0 | 60 | 0 | 0 | 0 |  |
|  | 0.0157 | 0 | 0 | 0 | 0 | 0 |  |
| 203 | 4.0000 | 30 | 100 | 0 | 100 | 100 | 20 |
|  | 1.0000 | 20 | 100 | 0 | 95 | 50 | 0 |
|  | 0.2500 | 10 | 75 | 0 | 50 | 0 | 0 |
|  | 0.0625 | 10 | 30 | 0 | 30 | 0 | 0 |
|  | 0.0157 | 0 | 20 | 0 | 0 | 0 | 0 |
| 204 | 4.0000 | 20 | 100 | 40 | 100 | 100 | 20 |
|  | 1.0000 | 0 | 100 | 40 | 90 | 100 | 10 |
|  | 0.2500 | 0 | 100 | 30 | 90 | 100 | 10 |
|  | 0.0625 | 0 | 85 | 30 | 70 | 30 | 0 |
|  | 0.0157 | 0 | 40 | 0 | 0 | 0 | 0 |
| 205 | 4.0000 | 30 | 100 | 50 | 100 | 100 | 20 |
|  | 1.0000 | 30 | 100 | 0 | 95 | 100 | 0 |
|  | 0.2500 | 30 | 100 | 0 | 95 | 50 | 0 |
|  | 0.0625 | 20 | 80 | 0 | 80 | 0 | 0 |
|  | 0.0157 | 10 | 40 | 0 | 20 | 0 | 0 |
| 206 | 4.0000 | 20 | 100 | 40 | 100 | 100 | 30 |
|  | 1.0000 | 0 | 100 | 30 | 90 | 100 | 0 |
|  | 0.2500 | 0 | 100 | 10 | 90 | 70 | 0 |
|  | 0.0625 | 0 | 100 | 10 | 80 | 0 | 0 |
|  | 0.0157 | 0 | 50 | 0 | 0 | 0 | 0 |
| 207 | 4.0000 | 0 | 100 | 20 | 100 | 100 | 30 |
|  | 1.0000 | 0 | 100 | 10 | 100 | 100 | 0 |
|  | 0.2500 | 0 | 100 | 0 | 90 | 100 | 0 |
|  | 0.0625 | 0 | 80 | 0 | 90 | 0 | 0 |
|  | 0.0157 | 0 | 60 | 0 | 50 | 0 | 0 |
| 208 | 4.0000 | 10 | 100 | 20 | 100 | 100 | 20 |
|  | 1.0000 | 0 | 100 | 20 | 90 | 30 | 0 |
|  | 0.2500 | 0 | 70 | 10 | 80 | 0 | 0 |
|  | 0.0625 | 0 | 60 | 0 | 20 | 0 | 0 |
|  | 0.0157 | 0 | 0 | 0 | 0 | 0 | 0 |
| 209 | 4.0000 | 0 | 100 | 10 | 100 | 50 | 0 |
|  | 1.0000 | 0 | 100 | 10 | 100 | 50 | 0 |
|  | 0.2500 | 0 | 70 | 0 | 70 | 50 | 0 |
|  | 0.0625 | 0 | 50 | 0 | 40 | 0 | 0 |
|  | 0.0157 | 0 | 50 | 0 | 20 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| 210 | 4.0000 | 20 | 100 | 100 | 100 | | |
| | 1.0000 | 20 | 100 | 100 | 100 | | |
| | 0.2500 | 10 | 80 | 100 | 95 | | |
| | 0.0625 | 0 | 0 | 0 | 30 | | |
| | 0.0157 | 0 | 0 | 0 | 30 | | |
| 211 | 4.0000 | 0 | 90 | 0 | 0 | 0 | 0 |
| | 1.0000 | 0 | 80 | 0 | 0 | 0 | 0 |
| | 0.2500 | 0 | 70 | 0 | 0 | 0 | 0 |
| | 0.0625 | 0 | 0 | 0 | 0 | 0 | 0 |
| | 0.0157 | 0 | 0 | 0 | 0 | 0 | 0 |
| 212 | 4.0000 | 40 | 100 | 40 | 100 | 100 | 0 |
| | 1.0000 | 20 | 100 | 40 | 90 | 100 | 0 |
| | 0.2500 | 10 | 100 | 30 | 70 | 70 | 0 |
| | 0.0625 | 0 | 95 | 20 | 20 | 70 | 0 |
| | 0.0157 | 0 | 80 | 0 | 0 | 0 | 0 |
| 213 | 4.0000 | 0 | 100 | 30 | 80 | 30 | 0 |
| | 1.0000 | 0 | 100 | 20 | 70 | 0 | 0 |
| | 0.2500 | 0 | 90 | 10 | 0 | 0 | 0 |
| | 0.0625 | 0 | 60 | 0 | 0 | 0 | 0 |
| | 0.0157 | 0 | 0 | 0 | 0 | 0 | 0 |
| 214 | 4.0000 | 0 | 100 | 10 | 100 | 0 | 0 |
| | 1.0000 | 0 | 100 | 0 | 90 | 0 | 0 |
| | 0.2500 | 0 | 95 | 0 | 40 | 0 | 0 |
| | 0.0625 | 0 | 70 | 0 | 0 | 0 | 0 |
| | 0.0157 | 0 | 0 | 0 | 0 | 0 | 0 |
| 216 | 4.0000 | 0 | 100 | 40 | 50 | 0 | 0 |
| | 1.0000 | 0 | 100 | 20 | 0 | 0 | 0 |
| | 0.2500 | 0 | 60 | 10 | 0 | 0 | 0 |
| | 0.0625 | 0 | 30 | 0 | 0 | 0 | 0 |
| | 0.0157 | 0 | 20 | 0 | 0 | 0 | 0 |
| 218 | 4.0000 | 10 | 100 | 40 | 100 | 0 | 0 |
| | 1.0000 | 0 | 100 | 20 | 80 | 0 | 0 |
| | 0.2500 | 0 | 100 | 10 | 70 | 0 | 0 |
| | 0.0625 | 0 | 90 | 0 | 30 | 0 | 0 |
| | 0.0157 | 0 | 30 | 0 | 0 | 0 | 0 |
| 219 | 4.0000 | 0 | 100 | 0 | 10 | 0 | 0 |
| | 1.0000 | 0 | 80 | 0 | 0 | 0 | 0 |
| | 0.2500 | 0 | 0 | 0 | 0 | 0 | 0 |
| | 0.0625 | 0 | 0 | 0 | 0 | 0 | 0 |
| | 0.0157 | 0 | 0 | 0 | 0 | 0 | 0 |
| 220 | 4.0000 | 0 | 100 | 80 | 100 | 100 | 60 |
| | 1.0000 | 0 | 95 | 0 | 0 | 90 | 0 |
| | 0.2500 | 0 | 60 | 0 | 0 | 0 | 0 |
| | 0.0625 | 0 | 0 | 0 | 0 | 0 | 0 |
| | 0.0157 | 0 | 0 | 0 | 0 | 0 | 0 |
| 221 | 1.0000 | 80 | 100 | 100 | 100 | 100 | 90 |
| | 0.2500 | 0 | 100 | 100 | 90 | 100 | 80 |
| | 0.0625 | 0 | 100 | 60 | 90 | 100 | 0 |
| | 0.0156 | 0 | 95 | 20 | 60 | 0 | 0 |
| | 0.0040 | 0 | 20 | 0 | 0 | 0 | 0 |
| 222 | 1.0000 | 80 | 100 | 100 | 100 | — | 70 |
| | 0.2500 | 70 | 100 | 100 | 100 | — | 60 |
| | 0.0625 | 20 | 100 | 40 | 90 | — | 30 |
| | 0.0156 | 0 | 70 | 10 | 80 | — | 0 |
| | 0.0040 | 0 | 30 | 0 | 40 | — | 0 |
| 223 | 4.0000 | 100 | 100 | 100 | 100 | 100 | 0 |
| | 1.0000 | 60 | 100 | 100 | 100 | 100 | 0 |
| | 0.2500 | 20 | 100 | 100 | 100 | 0 | 0 |
| | 0.0625 | 0 | 100 | 50 | 80 | 0 | 0 |
| | 0.0156 | 0 | 30 | 0 | 30 | 0 | 0 |
| 224 | 1.0000 | 0 | 100 | 100 | 90 | — | 50 |
| | 0.2500 | 0 | 100 | 60 | 90 | — | 10 |
| | 0.0625 | 0 | 95 | 10 | 80 | — | 0 |
| | 0.0156 | 0 | 40 | 0 | 50 | — | 0 |
| | 0.0640 | 0 | 0 | 0 | 0 | — | 0 |
| 225 | 1.0000 | 30 | 100 | 100 | 90 | — | 50 |
| | 0.2500 | 30 | 100 | 100 | 90 | 80 | 20 |
| | 0.0625 | 0 | 80 | 20 | 80 | 80 | 0 |
| | 0.0156 | 0 | 60 | 0 | 50 | 70 | 0 |
| | 0.0040 | 0 | 0 | 0 | 20 | 0 | 0 |
| 226 | 1.0000 | 70 | 100 | 100 | 90 | — | 60 |
| | 0.2500 | 40 | 100 | 100 | 80 | 90 | 30 |
| | 0.0625 | 0 | 85 | 30 | 80 | 40 | 0 |
| | 0.0156 | 0 | 50 | 10 | 50 | 0 | 0 |
| | 0.0040 | 0 | 0 | 0 | 20 | 0 | 0 |
| 227 | 4.0000 | 100 | 100 | 100 | 100 | 0 | 100 |

TABLE 8-continued

| Comp. No. | amount (kg/ha) | ORYSA | ECHOR | SCPJU | MOOVA | CYPSE | SAGPY |
|---|---|---|---|---|---|---|---|
| | 1.0000 | 50 | 100 | 100 | 100 | 0 | 100 |
| | 0.2500 | 30 | 100 | 100 | 90 | 0 | 100 |
| | 0.0625 | 0 | 100 | 100 | 90 | 0 | 40 |
| | 0.0156 | 0 | 90 | 40 | 70 | 0 | 0 |
| 228 | 1.0000 | 40 | 100 | 100 | 100 | 100 | 60 |
| | 0.2500 | 10 | 100 | 70 | 90 | 100 | 40 |
| | 0.0625 | 0 | 90 | 0 | 50 | 0 | 10 |
| | 0.0156 | 0 | 30 | 0 | 0 | 0 | 0 |
| | 0.0040 | 0 | 0 | 0 | 0 | 0 | 0 |
| 229 | 1.0000 | 65 | 100 | 100 | 100 | — | 70 |
| | 0.2500 | 0 | 100 | 90 | 90 | — | 50 |
| | 0.0625 | 0 | 80 | 30 | 70 | — | 20 |
| | 0.0156 | 0 | 30 | 0 | 40 | 0 | 0 |
| | 0.0040 | 0 | 0 | 0 | 20 | 0 | 0 |
| 230 | 4.0000 | 80 | 100 | 100 | 100 | 100 | 0 |
| | 1.0000 | 60 | 100 | 100 | 100 | 100 | 0 |
| | 0.2500 | 20 | 100 | 40 | 90 | 100 | 0 |
| | 0.0625 | 20 | 100 | 0 | 80 | 20 | 0 |
| | 0.0156 | 20 | 90 | 0 | 50 | 0 | 0 |
| 231 | 4.0000 | 90 | 100 | 100 | 100 | 100 | 100 |
| | 1.0000 | 90 | 100 | 100 | 100 | 100 | 100 |
| | 0.2500 | 70 | 100 | 100 | 100 | 100 | 60 |
| | 0.6250 | 0 | 100 | 100 | 100 | 100 | 30 |
| | 0.0156 | 0 | 70 | 40 | 60 | 0 | 9 |
| 232 | 1.0000 | 65 | 100 | 100 | 100 | — | 50 |
| | 0.2500 | 30 | 100 | 100 | 90 | — | 50 |
| | 0.0625 | 0 | 100 | 100 | 90 | — | 0 |
| | 0.0156 | 0 | 90 | 50 | 80 | 50 | 0 |
| | 0.0040 | 0 | 70 | 10 | 50 | 0 | 0 |
| 233 | 1.0000 | 65 | 100 | 100 | 90 | — | 80 |
| | 0.2500 | 20 | 100 | 50 | 90 | 60 | 50 |
| | 0.0625 | 0 | 95 | 10 | 70 | — | 0 |
| | 0.0156 | 0 | 80 | 0 | 70 | 0 | 0 |
| | 0.0040 | 0 | 0 | 0 | 20 | 0 | 0 |
| 234 | 1.0000 | 60 | 100 | 100 | 100 | 100 | 70 |
| | 0.2500 | 20 | 100 | 100 | 100 | 100 | 50 |
| | 0.0625 | 0 | 100 | 60 | 100 | 100 | 20 |
| | 0.0156 | 0 | 80 | 10 | 30 | 0 | 0 |
| | 0.0040 | 0 | 30 | 0 | 0 | 0 | 0 |
| 235 | 1.0000 | 0 | 100 | 30 | 100 | 100 | 50 |
| | 0.2500 | 0 | 100 | 0 | 90 | 20 | 20 |
| | 0.0625 | 0 | 95 | 0 | 80 | 0 | 0 |
| | 0.0156 | 0 | 30 | 0 | 10 | 0 | 0 |
| | 0.0040 | 0 | 0 | 0 | 0 | 0 | 0 |
| 236 | 4.0000 | 60 | 100 | 100 | 100 | 100 | 100 |
| | 1.0000 | 50 | 100 | 100 | 100 | 100 | 100 |
| | 0.2500 | 30 | 100 | 60 | 100 | 0 | 100 |
| | 0.0625 | 10 | 80 | 40 | 60 | 0 | 0 |
| | 0.0156 | 0 | 60 | 0 | 40 | 0 | 0 |
| 237 | 1.0000 | 60 | 100 | 100 | 100 | 100 | 70 |
| | 0.2500 | 10 | 100 | 100 | 100 | 100 | 50 |
| | 0.0625 | 0 | 100 | 40 | 100 | 100 | 30 |
| | 0.0156 | 0 | 95 | 0 | 80 | 0 | 0 |
| | 0.0040 | 0 | 60 | 0 | 20 | 0 | 0 |
| 238 | 1.0000 | 50 | 100 | 100 | 100 | 100 | 100 |
| | 0.2500 | 20 | 100 | 80 | 100 | 90 | 60 |
| | 0.0625 | 0 | 100 | 30 | 60 | 0 | 0 |
| | 0.0156 | 0 | 60 | 0 | 20 | 0 | 0 |
| | 0.0040 | 0 | 0 | 0 | 0 | 0 | 0 |
| 239 | 4.0000 | 100 | 100 | 100 | 100 | 100 | 50 |
| | 1.0000 | 50 | 100 | 100 | 100 | 100 | 30 |
| | 0.2500 | 20 | 100 | 30 | 100 | 100 | 0 |
| | 0.0625 | 0 | 90 | 20 | 60 | 20 | 0 |
| | 0.0156 | 0 | 20 | 0 | 30 | 0 | 0 |
| 240 | 1.0000 | 10 | 100 | 60 | 100 | 100 | 60 |
| | 0.2500 | 0 | 100 | 30 | 90 | 0 | 0 |
| | 0.0625 | 0 | 90 | 0 | 70 | 0 | 0 |
| | 0.0156 | 0 | 60 | 0 | 0 | 0 | 0 |
| | 0.0040 | 0 | 0 | 0 | 0 | 0 | 0 |
| 241 | 1.0000 | 10 | 100 | 40 | 90 | 100 | 60 |
| | 0.2500 | 0 | 95 | 10 | 90 | 10 | 10 |
| | 0.0625 | 0 | 90 | 0 | 90 | 0 | 0 |
| | 0.0156 | 0 | 60 | 0 | 10 | 0 | 0 |
| | 0.0040 | 0 | 0 | 0 | 0 | 0 | 0 |
| 242 | 1.0000 | 20 | 100 | 60 | 100 | 100 | 60 |
| | 0.2500 | 10 | 100 | 0 | 100 | 80 | 40 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0625 | 0 | 80 | 0 | 40 | 0 | 10 |
| | 0.0156 | 0 | 50 | 0 | 10 | 0 | 0 |
| | 0.0040 | 0 | 0 | 0 | 0 | 0 | 0 |
| 243 | 1.0000 | 40 | 100 | 100 | 90 | 100 | 50 |
| | 0.2500 | 10 | 100 | 90 | 90 | 100 | 0 |
| | 0.0625 | 0 | 100 | 10 | 90 | 0 | 0 |
| | 0.0156 | 0 | 90 | 0 | 30 | 0 | 0 |
| | 0.0040 | 0 | 0 | 0 | 0 | 0 | 0 |
| 244 | 1.0000 | 20 | 100 | 60 | 100 | 70 | 90 |
| | 0.2500 | 0 | 100 | 40 | 50 | 50 | 0 |
| | 0.0525 | 0 | 100 | 0 | 30 | 40 | 0 |
| | 0.0156 | 0 | 50 | 0 | 0 | 0 | 0 |
| | 0.0040 | 0 | 0 | 0 | 0 | 0 | 0 |
| 245 | 1.0000 | 20 | 100 | 100 | 90 | 100 | 0 |
| | 0.2500 | 0 | 100 | 100 | 90 | 100 | 0 |
| | 0.0625 | 0 | 95 | 30 | 70 | 80 | 0 |
| | 0.0156 | 0 | 60 | 0 | 0 | 0 | 0 |
| | 0.0040 | 0 | 0 | 0 | 0 | 0 | 0 |
| 246 | 1.0000 | 50 | 100 | 100 | 100 | — | 60 |
| | 0.2500 | 30 | 100 | 50 | 90 | — | 60 |
| | 0.0625 | 10 | 95 | 0 | 80 | 80 | 30 |
| | 0.0156 | 0 | 40 | 0 | 40 | — | 0 |
| | 0.0040 | 0 | 10 | 0 | 20 | 0 | 0 |
| 247 | 1.0000 | 50 | 100 | 100 | 100 | 100 | 80 |
| | 0.2500 | 0 | 100 | 70 | 90 | 100 | 40 |
| | 0.0625 | 0 | 100 | 40 | 70 | 0 | 10 |
| | 0.0156 | 0 | 80 | 10 | 40 | 0 | 0 |
| | 0.0040 | 0 | 60 | 0 | 10 | 0 | 0 |
| 248 | 1.0000 | 70 | 100 | 100 | 100 | 100 | 90 |
| | 0.2500 | 10 | 100 | 100 | 90 | 90 | 40 |
| | 0.0625 | 0 | 100 | 50 | 90 | 80 | 20 |
| | 0.0156 | 0 | 95 | 20 | 80 | 0 | 0 |
| | 0.0040 | 0 | 80 | 0 | 10 | 0 | 0 |
| 249 | 1.0000 | 20 | 100 | 100 | 100 | 100 | 40 |
| | 0.2500 | 10 | 100 | 50 | 100 | 30 | 30 |
| | 0.0625 | 0 | 100 | 50 | 100 | 0 | 30 |
| | 0.0156 | 0 | 70 | 50 | 50 | 0 | 30 |
| | 0.0040 | 0 | 50 | 50 | 50 | 0 | 0 |
| 250 | 1.0000 | 10 | 100 | 100 | 100 | 100 | 40 |
| | 0.2500 | 0 | 100 | 100 | 100 | 100 | 40 |
| | 0.0625 | 0 | 80 | 50 | 80 | 100 | 20 |
| | 0.0156 | 0 | 50 | 30 | 50 | 0 | 10 |
| | 0.0040 | 0 | 0 | 0 | 10 | 0 | 0 |
| 251 | 1.0000 | 10 | 100 | 70 | 90 | 100 | 20 |
| | 0.2500 | 0 | 90 | 50 | 90 | 100 | 60 |
| | 0.0625 | 0 | 60 | 0 | 20 | 0 | 0 |
| | 0.0560 | 0 | 60 | 0 | 0 | 0 | 0 |
| | 0.0040 | 0 | 0 | 0 | 0 | 0 | 0 |
| 252 | 1.0000 | 20 | 100 | 100 | 100 | — | 20 |
| | 0.2500 | 20 | 90 | 70 | 90 | 0 | 0 |
| | 0.0625 | 10 | 80 | 20 | 80 | 0 | 0 |
| | 0.0156 | 0 | 60 | 0 | 80 | 0 | 0 |
| | 0.0040 | 0 | 0 | 0 | 30 | 0 | 0 |
| 253 | 4.0000 | 70 | 100 | 100 | 100 | 100 | 100 |
| | 1.0000 | 40 | 100 | 100 | 100 | 100 | 90 |
| | 0.2500 | 0 | 100 | 30 | 80 | 100 | 50 |
| | 0.0625 | 0 | 100 | 0 | 70 | 30 | 0 |
| | 0.0156 | 0 | 60 | 0 | 40 | 0 | 0 |
| 254 | 4.0000 | 50 | 100 | 100 | 100 | 100 | 100 |
| | 1.0000 | 40 | 100 | 80 | 100 | 100 | 100 |
| | 0.2500 | 20 | 100 | 50 | 90 | 0 | 0 |
| | 0.0625 | 0 | 95 | 0 | 40 | 0 | 0 |
| | 0.0156 | 0 | 50 | 0 | 0 | 0 | 0 |
| 255 | 1.0000 | 20 | 100 | 50 | 100 | 100 | 60 |
| | 0.2500 | 10 | 100 | 20 | 90 | 100 | 0 |
| | 0.0625 | 0 | 90 | 0 | 70 | 0 | 0 |
| | 0.0156 | 0 | 40 | 0 | 30 | 0 | 0 |
| | 0.0040 | 0 | 40 | 0 | 0 | 0 | 0 |
| 256 | 4.0000 | 60 | 100 | 100 | 100 | 100 | 0 |
| | 1.0000 | 0 | 100 | 50 | 100 | 100 | 0 |
| | 0.2500 | 0 | 100 | 0 | 60 | 0 | 0 |
| | 0.0625 | 0 | 80 | 0 | 20 | 0 | 0 |
| | 0.0156 | 0 | 0 | 0 | 0 | 0 | 0 |
| 257 | 1.0000 | 0 | 100 | 40 | 100 | 100 | 0 |
| | 0.2500 | 0 | 100 | 20 | 90 | 100 | 0 |
| | 0.0625 | 0 | 95 | 0 | 40 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0156 | 0 | 40 | 0 | 10 | 0 | 0 |
| | 0.0040 | 0 | 0 | 0 | 0 | 0 | 0 |
| 258 | 1.0000 | 10 | 95 | 10 | 90 | 0 | 20 |
| | 0.2500 | 0 | 80 | 0 | 40 | 0 | 10 |
| | 0.0625 | 0 | 70 | 0 | 10 | 0 | 0 |
| | 0.0156 | 0 | 0 | 0 | 0 | 0 | 0 |
| | 0.0040 | 0 | 0 | 0 | 0 | 0 | 0 |
| 259 | 4.0000 | 70 | 100 | 100 | 100 | 100 | 90 |
| | 1.0000 | 50 | 100 | 100 | 100 | 100 | 60 |
| | 0.2500 | 20 | 90 | 40 | 70 | 0 | 0 |
| | 0.0625 | 0 | 80 | 0 | 30 | 0 | 0 |
| | 0.0156 | 0 | 80 | 0 | 0 | 0 | 0 |
| 260 | 4.0000 | 90 | 100 | 100 | 100 | 100 | 100 |
| | 1.0000 | 80 | 100 | 100 | 100 | 100 | 80 |
| | 0.2500 | 50 | 100 | 90 | 100 | 100 | 50 |
| | 0.0625 | 20 | 100 | 40 | 70 | 40 | 0 |
| | 0.0056 | 0 | 60 | 0 | 0 | 0 | 0 |
| 261 | 4.0000 | 100 | 100 | 100 | 100 | 100 | 90 |
| | 1.0000 | 90 | 100 | 100 | 100 | 100 | 0 |
| | 0.2500 | 20 | 90 | 90 | 60 | 100 | 0 |
| | 0.0625 | 0 | 70 | 30 | 20 | 100 | 0 |
| | 0.0156 | 0 | 0 | 0 | 0 | 0 | 0 |
| 262 | 2.0000 | 0 | 100 | 0 | 100 | 50 | 50 |
| | 0.5000 | 0 | 100 | 0 | 100 | 20 | 0 |
| | 0.1250 | 0 | 100 | 0 | 90 | 0 | 0 |
| | 0.0310 | 0 | 60 | 0 | 30 | 0 | 0 |
| | 0:0080 | 0 | 20 | 0 | 0 | 0 | 0 |
| 263 | 4.0000 | 0 | 100 | 20 | 100 | 100 | 50 |
| | 1.0000 | 0 | 100 | 0 | 100 | 100 | 0 |
| | 0.2500 | 0 | 100 | 0 | 100 | 100 | 0 |
| | 0.0625 | 0 | 95 | 0 | 100 | 50 | 0 |
| | 0.0156 | 0 | 80 | 0 | 30 | 0 | 0 |
| 264 | 4.0000 | 90 | 100 | 100 | 100 | 100 | 100 |
| | 1.0000 | 80 | 100 | 100 | 100 | 100 | 90 |
| | 0.2500 | 60 | 100 | 100 | 90 | 50 | 80 |
| | 0.0625 | 10 | 100 | 100 | 90 | 30 | 30 |
| | 0.0156 | 0 | 70 | 20 | 70 | 0 | 0 |
| 265 | 1.0000 | 50 | 100 | 100 | 100 | — | 80 |
| | 0.2500 | 10 | 100 | 60 | 90 | — | 0 |
| | 0.0625 | 0 | 95 | 10 | 90 | — | 0 |
| | 0.0156 | 0 | 80 | 0 | 70 | — | 0 |
| | 0.0040 | 0 | 20 | 0 | 60 | — | 0 |
| 266 | 1.0000 | 100 | 100 | 100 | 100 | — | 90 |
| | 0.2500 | 0 | 100 | 90 | 90 | — | 60 |
| | 0.0625 | 0 | 100 | 20 | 90 | 90 | 20 |
| | 0.0156 | 0 | 70 | 10 | 80 | 0 | 0 |
| | 0.0040 | 0 | 30 | 0 | 60 | 0 | 0 |
| 267 | 1.0000 | 10 | 100 | 50 | 90 | — | 80 |
| | 0.2500 | 0 | 100 | 40 | 80 | — | 0 |
| | 0.0625 | 0 | 95 | 30 | 80 | 70 | 0 |
| | 0.0156 | 0 | 60 | 0 | 50 | 0 | 0 |
| | 0.0040 | 0 | 0 | 0 | 0 | 0 | 0 |
| 268 | 1.0000 | 40 | 100 | 100 | 90 | — | 60 |
| | 0.2500 | 0 | 100 | 90 | 90 | — | 40 |
| | 0.0625 | 0 | 95 | 10 | 80 | 60 | 30 |
| | 0.0156 | 0 | 65 | 0 | 70 | 0 | 0 |
| | 0.0040 | 0 | 20 | 0 | 50 | 0 | 0 |
| 269 | 1.0000 | 70 | 100 | 90 | 100 | — | 80 |
| | 0.2500 | 10 | 100 | 30 | 80 | — | 50 |
| | 0.0625 | 0 | 95 | 0 | 80 | — | 10 |
| | 0.0156 | 0 | 70 | 0 | 80 | 0 | 0 |
| | 0.0040 | 0 | 0 | 0 | 40 | 0 | 0 |
| 270 | 1.0000 | 90 | 100 | 100 | 100 | — | 80 |
| | 0.2500 | 50 | 100 | 30 | 90 | — | 50 |
| | 0.0265 | 30 | 100 | 20 | 80 | — | 10 |
| | 0.0156 | 10 | 70 | 10 | 80 | 0 | 0 |
| | 0.0040 | 0 | 20 | 10 | 60 | 0 | 0 |
| 271 | 1.0000 | 10 | 100 | 90 | 90 | — | 80 |
| | 0.2500 | 0 | 100 | 50 | 80 | — | 0 |
| | 0.0625 | 0 | 90 | 10 | 70 | 60 | 0 |
| | 0.0156 | 0 | 70 | 0 | 60 | — | 0 |
| | 0.0040 | 0 | 0 | 0 | 50 | 0 | 0 |
| 272 | 1.0000 | 50 | 100 | 100 | 100 | 100 | 60 |
| | 0.2500 | 0 | 100 | 30 | 80 | 20 | 0 |
| | 0.0625 | 0 | 100 | 0 | 70 | 20 | 0 |
| | 0.0156 | 0 | 70 | 0 | 20 | 0 | 0 |

TABLE 8-continued

| Comp. No. | amount (kg/ha) | ORYSA | ECHOR | SCPJU | MOOVA | CYPSE | SAGPY |
|---|---|---|---|---|---|---|---|
| | 0.0040 | 0 | 0 | 0 | 0 | 0 | 0 |
| 273 | 1.0000 | 50 | 100 | 100 | 100 | — | 90 |
| | 0.2500 | 20 | 100 | 100 | 90 | — | 70 |
| | 0.0625 | 0 | 100 | 30 | 90 | 60 | 20 |
| | 0.0056 | 0 | 70 | 20 | 80 | 30 | 0 |
| | 0.0040 | 0 | 30 | 0 | 30 | 30 | 0 |
| 274 | 1.0000 | 60 | 100 | 100 | 100 | — | 100 |
| | 0.2500 | 0 | 100 | 100 | 100 | — | 90 |
| | 0.0625 | 0 | 100 | 30 | 90 | — | 40 |
| | 0.0156 | 0 | 80 | 30 | 80 | 80 | 0 |
| | 0.0040 | 0 | 60 | 0 | 50 | 0 | 0 |
| 275 | 1.0000 | 20 | 100 | 100 | 100 | — | 70 |
| | 0.2500 | 0 | 100 | 50 | 90 | — | 50 |
| | 0.0625 | 0 | 90 | 10 | 80 | 50 | 10 |
| | 0.0156 | 0 | 70 | 0 | 50 | 0 | 0 |
| | 0.0040 | 0 | 0 | 0 | 30 | 0 | 0 |
| 276 | 1.0000 | 20 | 100 | 706 | 100 | — | 70 |
| | 0.2500 | 0 | 100 | 30 | 90 | — | 20 |
| | 0.0625 | 0 | 95 | 20 | 80 | — | 0 |
| | 0.0156 | 0 | 75 | 0 | 50 | — | 0 |
| | 0.0040 | 0 | 20 | 0 | 40 | 0 | 0 |
| 277 | 1.0000 | 20 | 100 | 10 | 100 | 0 | 50 |
| | 02500 | 0 | 95 | 0 | 90 | 0 | 10 |
| | 0.0625 | 0 | 30 | 0 | 70 | 0 | 0 |
| | 0.0156 | 0 | 30 | 0 | 50 | 0 | 0 |
| | 0.0040 | 0 | 0 | 0 | 0 | 0 | 0 |
| 278 | 1.0000 | 0 | 100 | 90 | 90 | 50 | 50 |
| | 0.2500 | 0 | 80 | 70 | 90 | — | 0 |
| | 0.0625 | 0 | 75 | 10 | 70 | — | 0 |
| | 0.0156 | 0 | 50 | 0 | 50 | 0 | 0 |
| | 0.0040 | 0 | 10 | 0 | 20 | 0 | 0 |
| 279 | 4.0000 | 90 | 100 | 100 | 100 | 100 | 100 |
| | 1.0000 | 80 | 100 | 100 | 100 | 100 | 70 |
| | 0.2500 | 10 | 100 | 90 | 80 | 100 | 50 |
| | 0.0625 | 0 | 90 | 70 | 70 | 40 | 30 |
| | 0.0156 | 0 | 60 | 0 | 30 | 0 | 0 |
| 280 | 4.0000 | 100 | 100 | 100 | 100 | 100 | 60 |
| | 1.0000 | 40 | 100 | 100 | 90 | 100 | 50 |
| | 0.2500 | 10 | 100 | 100 | 90 | 100 | 0 |
| | 0.0625 | 0 | 90 | 30 | 30 | 0 | 0 |
| | 0.0056 | 0 | 20 | 0 | 0 | 0 | 0 |
| 281 | 4.0000 | 40 | 100 | 100 | 100 | 70 | 0 |
| | 1.0000 | 20 | 100 | 100 | 100 | 0 | 0 |
| | 0.2500 | 0 | 90 | 0 | 40 | 0 | 0 |
| | 0.0625 | 0 | 70 | 0 | 0 | 0 | 0 |
| | 0.0156 | 0 | 20 | 0 | 0 | 0 | 0 |
| 282 | 4.0000 | 0 | 100 | 40 | 90 | 0 | 0 |
| | 1.0000 | 0 | 100 | 0 | 50 | 0 | 0 |
| | 0.2500 | 0 | 60 | 0 | 0 | 0 | 0 |
| | 0.0625 | 0 | 40 | 0 | 0 | 0 | 0 |
| | 0.0156 | 0 | 0 | 0 | 0 | 0 | 0 |
| 283 | 4.0000 | 70 | 100 | 100 | 100 | 100 | 0 |
| | 1.0000 | 30 | 100 | 100 | 100 | 100 | 0 |
| | 0.2500 | 0 | 100 | 50 | 100 | 100 | 0 |
| | 0.0625 | 0 | 90 | 0 | 90 | 100 | 0 |
| | 0.0156 | 0 | 90 | 0 | 20 | 10 | 0 |
| 284 | 4.0000 | 80 | 100 | 100 | 100 | 100 | 0 |
| | 1.0000 | 40 | 100 | 100 | 100 | 100 | 0 |
| | 0.2500 | 0 | 100 | 0 | 100 | 100 | 0 |
| | 0.0625 | 0 | 80 | 0 | 80 | 100 | 0 |
| | 0.0156 | 0 | 80 | 0 | 0 | 0 | 0 |
| 285 | 4.0000 | 80 | 100 | 100 | 100 | 100 | 100 |
| | 1.0000 | 50 | 100 | 100 | 100 | 100 | 100 |
| | 0.2500 | 40 | 100 | 90 | 90 | 100 | 100 |
| | 0.0625 | 30 | 100 | 60 | 80 | 60 | 60 |
| | 0.0156 | 0 | 60 | 0 | 50 | 0 | 0 |
| 286 | 4.0000 | 80 | 100 | 100 | 100 | 100 | 0 |
| | 1.0000 | 40 | 100 | 40 | 100 | 100 | 0 |
| | 0.2500 | 20 | 100 | 30 | 90 | 90 | 0 |
| | 0.0625 | 0 | 80 | 20 | 80 | 20 | 0 |
| | 0.0156 | 0 | 60 | 0 | 50 | 10 | 0 |
| 287 | 4.0000 | 60 | 100 | 100 | 100 | 100 | 100 |
| | 1.0000 | 40 | 100 | 80 | 100 | 100 | 100 |
| | 0.2500 | 30 | 100 | 40 | 100 | 50 | 100 |
| | 0.0625 | 0 | 80 | 30 | 100 | 30 | 100 |
| | 0.0156 | 0 | 80 | 0 | 60 | 30 | 50 |

TABLE 8-continued

| Comp. No. | amount (kg/ha) | ORYSA | ECHOR | SCPJU | MOOVA | CYPSE | SAGPY |
|---|---|---|---|---|---|---|---|
| 288 | 4.0000 | 50 | 100 | 40 | 90 | 50 | 0 |
|  | 1.0000 | 0 | 100 | 0 | 40 | 0 | 0 |
|  | 0.2500 | 0 | 90 | 0 | 0 | 0 | 0 |
|  | 0..0625 | 0 | 50 | 0 | 0 | 0 | 0 |
|  | 0.0156 | 0 | 10 | 0 | 0 | 0 | 0 |
| 289 | 4.0000 | 0 | 80 | 0 | 40 | 100 | 60 |
|  | 1.0000 |  |  |  |  |  |  |
|  | 0.2500 |  |  |  |  |  |  |
|  | 0.0625 |  |  |  |  |  |  |
|  | 0.0156 |  |  |  |  |  |  |
| 290 | 4.0000 | 100 | 100 | 100 | 100 | 100 | 80 |
|  | 1.0000 | 40 | 100 | 100 | 100 | 100 | 80 |
|  | 0.2500 | 10 | 100 | 100 | 100 | 100 | 50 |
|  | 0.0625 | 0 | 100 | 50 | 70 | 40 | 0 |
|  | 0.0155 | 0 | 70 | 0 | 20 | 0 | 0 |
| 291 | 4.0000 | 100 | 100 | 100 | 100 | 100 | 0 |
|  | 1.0000 | 40 | 100 | 100 | 100 | 100 | 0 |
|  | 0.2500 | 10 | 100 | 0 | 100 | 100 | 0 |
|  | 0.0625 | 0 | 100 | 0 | 80 | 100 | 0 |
|  | 0.0156 | 0 | 80 | 0 | 0 | 0 | 0 |
| 292 | 4.0000 | 60 | 100 | 100 | 100 | 100 | 0 |
|  | 1.0000 | 30 | 100 | 100 | 100 | 100 | 0 |
|  | 0.2500 | 0 | 100 | 0 | 50 | 0 | 0 |
|  | 0.0625 | 0 | 95 | 0 | 0 | 0 | 0 |
|  | 0.0156 | 0 | 20 | 0 | 0 | 0 | 0 |
| 293 | 4.0000 | 70 | 100 | 100 | 100 | 100 | 90 |
|  | 1.0000 | 0 | 100 | 100 | 100 | 30 | 90 |
|  | 0.2500 | 0 | 100 | 100 | 100 | 30 | 0 |
|  | 0.0625 | 0 | 100 | 0 | 80 | 20 | 0 |
|  | 0.0156 | 0 | 50 | 0 | 20 | 0 | 0 |
| 294 | 4.0000 | 50 | 100 | 90 | 100 | 100 | 40 |
|  | 1.0000 | 20 | 100 | 60 | 100 | 20 | — |
|  | 0.2500 | 0 | 100 | 30 | 80 | 0 | — |
|  | 0.0625 | 0 | 80 | 0 | 80 | 0 | 0 |
|  | 0.0156 | 0 | 0 | 0 | 70 | 0 | 0 |

As can be seen from Table 8, the compounds of the present invention have high herbicidal activity against a wide spectrum of weeds and are very selective, e.g., they do not harm rice plants.

While the invention has been described with respect to the specific embodiments, it should be recognized that various modifications and changes may be made by those skilled in the art to the invention which also fall within the scope of the invention as defined by the appended claims.

What is. claimed is:

1. A compound of formula (I):

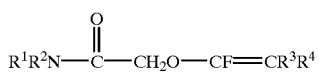

(I)

wherein:
R$^1$ is a phenyl group optionally having one or more substituents selected from the group consisting of C$_{1-6}$ alkyl, halogen-substituted C$_{1-6}$ alkyl, C$_{1-6}$ alkoxy and halogen;
R$^2$ is a C$_{1-6}$ alkyl group; or
R$^1$ and R$^2$ together with the nitrogen atom to which they are bound form a 5-, 6- or 7-membered nitrogen heterocycle optionally having one or more ring oxygen atoms, double bonds and C$_{1-6}$ alkyl substituents;
R$^3$ is a phenyl or thiophen-2-yl group optionally having one or more substituents selected from the group consisting of C$_{1-6}$ alkyl, halogen-substituted C$_{1-6}$ alkyl, C$_{1-6}$ alkoxy, methylenedioxy and halogen; and R$^4$ is a perfluoro C$_{1-6}$ alkyl group.

2. The compound of claim 1, which is the E isomer of formula (I-a):

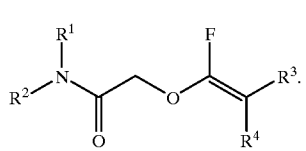

(I-a)

3. The compound of claim 1, which is the Z isomer of formula (I-b):

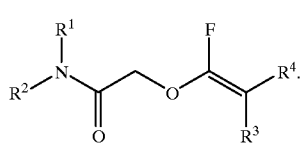

(I-b)

4. The compound of claim 1, wherein R$^1$ is phenyl group optionally having a halogen, methyl or methoxy substituent; R$^2$ is a methyl or i-propyl group; R$^3$ is a phenyl group optionally having a halogen or methoxy substituent; and R$^4$ is CF$_3$ or CF$_2$CF$_3$.

5. The compound of claim 1, wherein R$^1$ and R$^2$ together with the nitrogen atom to which they are bound form a piperidino, hexamethyleneimino, morphorino or 1,2,3,6-tetrahydropyridino ring optionally having one or two C$_{1-2}$ alkyl substituents, $R^3$ is a phenyl group optionally substituted with a halogen or methoxy group and $R^4$ is $CF_3$.

6. A process for the preparation of the compound of claim 1 which comprises reacting a compound of formula (II) with a compound of formula (III) in the presence of a base:

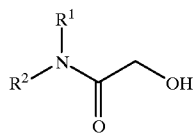
(II)

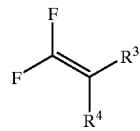
(III)

wherein $R^1$, $R^2$, $R^3$ and $R^4$ have the same meanings as defined in claim 1.

7. A herbicidal composition comprising a herbicidally effective amount of the compound of claim 1 as an active ingredient and an inert carrier.

* * * * *